US008652831B2

(12) United States Patent
Boecker

(10) Patent No.: US 8,652,831 B2
(45) Date of Patent: Feb. 18, 2014

(54) METHOD AND APPARATUS FOR ANALYTE MEASUREMENT TEST TIME

(75) Inventor: Dirk Boecker, Palo Alto, CA (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1615 days.

(21) Appl. No.: 12/055,973

(22) Filed: Mar. 26, 2008

(65) Prior Publication Data
US 2008/0210574 A1 Sep. 4, 2008

Related U.S. Application Data

(63) Continuation-in-part of application No. 11/813,014, filed as application No. PCT/US2005/047480 on Dec. 30, 2005, now abandoned, application No. 12/055,973, which is a continuation-in-part of application No. 10/540,912, filed on Mar. 27, 2006, now abandoned.

(60) Provisional application No. 60/640,879, filed on Dec. 30, 2004.

(51) Int. Cl.
*C12M 1/34* (2006.01)
*C12M 3/00* (2006.01)
*G01N 35/00* (2006.01)

(52) U.S. Cl.
USPC ........................................ 435/287.1; 436/44

(58) Field of Classification Search
USPC ............. 600/583, 584; 606/181–183; 436/44, 436/165; 422/56–58, 61, 63, 66, 67, 68.1, 422/104; 435/287.1
See application file for complete search history.

(56) References Cited

U.S. PATENT DOCUMENTS

| | | | |
|---|---|---|---|
| 2,061 A | 4/1841 | Osdel | 606/182 |
| 55,620 A | 6/1866 | Capewell | 606/181 |

(Continued)

FOREIGN PATENT DOCUMENTS

| | | |
|---|---|---|
| DE | 200 09 475 | 9/2000 |
| DE | 10053974 | 12/2000 |

(Continued)

OTHER PUBLICATIONS

Machine translation of DE 10053974 pp. 1-4, provided by epo.org.

(Continued)

*Primary Examiner* — Brian Szmal
(74) *Attorney, Agent, or Firm* — Paul Davis; Mintz Levin

(57) ABSTRACT

A disposable biosensor test strip is provided that includes a plurality of penetrating members. Each penetrating member is associated with a capillary chamber that has a depth suitable for capillary flow of blood and holds a volume of less than about 1.0 µl of the blood sample. A working electrode and a counter or reference electrode are disposed within the capillary chamber. A reagent is proximal to or in contact with at least the working electrode. The reagent includes an enzyme and a mediator. The reagent reacts with glucose to produce an electroactive reaction product. A blood sample, containing glucose, is applied into the capillary chamber. The capillary chamber directs capillary flow of the blood sample into contact with the reagent to cause the blood sample to at least partially solubilize or hydrate the reagent. The blood sample is detected in the capillary chamber. The electroactive reaction product is electro-oxidized or electro-reduced at the working electrode. Within 10 seconds after detecting, a determination is made of glucose concentration and a readout of the measurement is provided. The glucose determination is made by correlating the electro-oxidized or electro-reduced electroactive reaction product to the concentration of glucose in the blood sample.

21 Claims, 10 Drawing Sheets

(56) References Cited

U.S. PATENT DOCUMENTS

| | | | | |
|---|---|---|---|---|
| 1,135,465 | A | 4/1915 | Pollock | 606/181 |
| 1,733,847 | A | 10/1929 | Wilmot | 292/332 |
| 2,258,857 | A | 10/1941 | McCann | 601/81 |
| 2,628,319 | A | 2/1953 | Vang | 310/15 |
| 2,714,890 | A | 8/1955 | Alfred | 606/169 |
| 2,763,935 | A | 9/1956 | Whaley | 33/511 |
| 2,801,633 | A | 8/1957 | Ehrlich | 606/181 |
| 2,880,876 | A | 4/1959 | Dujardin | 210/523 |
| 3,046,987 | A | 7/1962 | Ehrlich | 128/314 |
| 3,030,959 | A | 9/1962 | Grunert | 128/329 |
| 3,063,451 | A | 11/1962 | Kowalk | 600/576 |
| 3,086,288 | A | 4/1963 | Balamuth | 30/277.4 |
| 3,090,384 | A | 5/1963 | Baldwin et al. | 604/272 |
| 3,208,452 | A | 9/1965 | Stern | 606/182 |
| 3,358,689 | A | 12/1967 | Higgins | 128/329 |
| 3,412,729 | A | 11/1968 | Smith, Jr. | 128/2.05 |
| 3,424,154 | A | 1/1969 | Kinsley | 604/70 |
| 3,448,307 | A | 6/1969 | Rudolph | 310/23 |
| 3,494,358 | A | 2/1970 | Grossenbacher | 128/218 |
| 3,607,097 | A | 9/1971 | Auphan et al. | 422/66 |
| 3,620,209 | A | 11/1971 | Kravitz | 601/79 |
| 3,626,929 | A | 12/1971 | Sanz | 128/2 R |
| 3,628,026 | A | 12/1971 | Cronin | 250/214.1 |
| 3,665,672 | A | 5/1972 | Speelman | 53/435 |
| 3,673,475 | A | 6/1972 | Britton | 318/122 |
| 3,712,292 | A | 1/1973 | Zentmeyer, Jr. | 128/2 G |
| 3,712,293 | A | 1/1973 | Mielke, Jr. | 128/2 |
| 3,734,812 | A | 5/1973 | Yazawa | 428/107 |
| 3,742,954 | A | 7/1973 | Strickland | 128/302 |
| 3,780,960 | A | 12/1973 | Tokuno | 242/555.2 |
| 3,832,776 | A | 9/1974 | Sawyer | 30/272 |
| 3,836,148 | A | 9/1974 | Manning | 273/368 |
| 3,851,543 | A | 12/1974 | Krom | 74/493 |
| 3,853,010 | A | 12/1974 | Christen | 73/864.24 |
| 3,924,818 | A | 12/1975 | Pfeifle | 242/364.7 |
| 3,938,526 | A | 2/1976 | Anderson | 128/303.1 |
| 3,953,172 | A | 4/1976 | Shapiro | 23/230 |
| 3,971,365 | A | 7/1976 | Smith | 128/2.17 |
| 4,057,394 | A | 11/1977 | Genshaw | 23/230 |
| 4,077,406 | A | 3/1978 | Sandhage | 604/61 |
| 4,109,655 | A | 8/1978 | Chacornac | 128/253 |
| 4,139,011 | A | 2/1979 | Benoit | 606/182 |
| 4,154,228 | A | 5/1979 | Feldstein | 606/169 |
| 4,168,130 | A | 9/1979 | Barth | 404/99 |
| 4,184,486 | A | 1/1980 | Papa | 600/373 |
| 4,190,420 | A | 2/1980 | Covington | 422/63 |
| 4,191,193 | A | 3/1980 | Seo | 600/488 |
| 4,193,690 | A | 3/1980 | Levenson | 356/301 |
| 4,203,446 | A | 5/1980 | Hofert | 606/182 |
| 4,207,870 | A | 6/1980 | Eldridge | 128/766 |
| 4,223,674 | A | 9/1980 | Fluent | 604/504 |
| 4,224,125 | A | 9/1980 | Nakamura | 204/195 B |
| 4,224,949 | A | 9/1980 | Scott | 128/734 |
| 4,230,118 | A | 10/1980 | Holman et al. | 128/314 |
| 4,240,439 | A | 12/1980 | Abe | 600/412 |
| 4,254,083 | A | 3/1981 | Columbus | 422/55 |
| 4,258,001 | A | 3/1981 | Pierce | 422/56 |
| 4,259,653 | A | 3/1981 | McGonigal | 310/15 |
| 4,299,230 | A | 11/1981 | Kubota | 600/300 |
| 4,301,412 | A | 11/1981 | Hill | 324/442 |
| 4,321,397 | A | 3/1982 | Nix | 548/366 |
| 4,338,174 | A | 7/1982 | Tamura | 204/195 |
| 4,340,669 | A | 7/1982 | Bauer | 435/14 |
| 4,350,762 | A | 9/1982 | De Luca | 435/10 |
| 4,353,984 | A | 10/1982 | Yamada | 435/14 |
| 4,356,826 | A | 11/1982 | Kubota | 600/300 |
| 4,360,016 | A | 11/1982 | Sarrine | 128/763 |
| 4,388,922 | A | 6/1983 | Telang | 604/319 |
| 4,391,905 | A | 7/1983 | Bauer | 435/14 |
| 4,391,906 | A | 7/1983 | Bauer | 435/14 |
| 4,392,933 | A | 7/1983 | Nakamura | 204/403.14 |
| 4,394,512 | A | 7/1983 | Batz | 548/365 |
| 4,397,556 | A | 8/1983 | Muller | 356/301 |
| 4,407,008 | A | 9/1983 | Schmidt | 356/301 |
| 4,411,266 | A | 10/1983 | Cosman | 128/303.18 |
| 4,414,975 | A | 11/1983 | Ryder | 128/314 |
| 4,418,037 | A | 11/1983 | Katsuyama | 422/56 |
| 4,420,564 | A | 12/1983 | Tsuji | 435/288 |
| 4,425,039 | A | 1/1984 | Grant | 356/35.5 |
| 4,426,451 | A | 1/1984 | Columbus | 436/518 |
| 4,426,884 | A | 1/1984 | Polchaninoff | 73/172 |
| 4,440,301 | A | 4/1984 | Intengan | 206/456 |
| 4,442,836 | A | 4/1984 | Meinecke | 128/314 |
| 4,442,972 | A | 4/1984 | Sahay | 236/1 EA |
| 4,449,529 | A | 5/1984 | Burns | 606/182 |
| 4,462,405 | A | 7/1984 | Ehrlich | 606/182 |
| 4,469,110 | A | 9/1984 | Slama | 128/770 |
| 4,490,139 | A | 12/1984 | Huizenga et al. | 604/57 |
| 4,517,978 | A | 5/1985 | Levin | 128/314 |
| 4,518,384 | A | 5/1985 | Tarello | 604/61 |
| 4,523,994 | A | 6/1985 | Shono | 549/352 |
| 4,535,769 | A | 8/1985 | Burns | 128/314 |
| 4,535,773 | A | 8/1985 | Yoon | 606/185 |
| 4,537,197 | A | 8/1985 | Hulka | 128/633 |
| 4,539,988 | A | 9/1985 | Shirley | 128/314 |
| 4,545,382 | A | 10/1985 | Higgins | 128/635 |
| 4,553,541 | A | 11/1985 | Burns | 128/314 |
| 4,561,445 | A | 12/1985 | Berke | 128/642 |
| 4,577,630 | A | 3/1986 | Nitzsche | 128/314 |
| 4,580,564 | A | 4/1986 | Andersen | 502/8 |
| 4,580,565 | A | 4/1986 | Cornell | 128/314 |
| 4,586,819 | A | 5/1986 | Tochigi | 356/301 |
| 4,586,926 | A | 5/1986 | Osborne | 604/272 |
| 4,590,411 | A | 5/1986 | Kelly | 318/687 |
| 4,595,479 | A | 6/1986 | Kimura | 204/294 |
| 4,600,014 | A | 7/1986 | Beraha | 128/754 |
| 4,603,209 | A | 7/1986 | Tsien | 549/352 |
| 4,608,997 | A | 9/1986 | Conway | 128/763 |
| 4,615,340 | A | 10/1986 | Cronenberg | 128/635 |
| 4,616,649 | A | 10/1986 | Burns | 128/314 |
| 4,619,754 | A | 10/1986 | Niki | 204/290 |
| 4,622,974 | A | 11/1986 | Coleman | 128/634 |
| 4,624,253 | A | 11/1986 | Burns | 128/314 |
| 4,627,445 | A | 12/1986 | Garcia | 600/583 |
| 4,637,393 | A | 1/1987 | Ray | 128/305 |
| 4,637,403 | A | 1/1987 | Garcia | 600/583 |
| 4,643,189 | A | 2/1987 | Mintz | 128/314 |
| 4,648,408 | A | 3/1987 | Hutcheson | 128/770 |
| 4,648,714 | A | 3/1987 | Benner | 356/301 |
| 4,653,511 | A | 3/1987 | Goch | 128/763 |
| 4,653,513 | A | 3/1987 | Dombrowski | 600/578 |
| 4,655,225 | A | 4/1987 | Dahne | 600/316 |
| 4,661,768 | A | 4/1987 | Carusillo | 324/678 |
| 4,666,438 | A | 5/1987 | Raulerson | 604/272 |
| 4,676,244 | A | 6/1987 | Enstrom | 128/314 |
| 4,677,979 | A | 7/1987 | Burns | 128/314 |
| 4,678,277 | A | 7/1987 | Delhaye | 356/301 |
| 4,682,892 | A | 7/1987 | Chawla | 356/353 |
| 4,702,594 | A | 10/1987 | Grant | 356/35.5 |
| 4,711,245 | A | 12/1987 | Higgins | 128/635 |
| 4,712,460 | A | 12/1987 | Allen | 83/208 |
| 4,712,548 | A | 12/1987 | Enstrom | 128/314 |
| 4,714,462 | A | 12/1987 | DiDomenico | 604/67 |
| 4,715,374 | A | 12/1987 | Maggio | 128/314 |
| 4,731,330 | A | 3/1988 | Hill | 436/16 |
| 4,731,726 | A | 3/1988 | Allen, III | 600/300 |
| 4,734,360 | A | 3/1988 | Phillips | 435/25 |
| 4,735,203 | A | 4/1988 | Ryder | 128/314 |
| 4,737,458 | A | 4/1988 | Batz | 435/28 |
| 4,750,489 | A | 6/1988 | Berkman | 606/166 |
| 4,753,776 | A | 6/1988 | Hillman | 422/101 |
| 4,756,884 | A | 7/1988 | Hillman | 422/73 |
| 4,757,022 | A | 7/1988 | Shults et al. | 435/291 |
| 4,758,323 | A | 7/1988 | Davis | 204/403 |
| 4,774,192 | A | 9/1988 | Terminiello | 436/530 |
| 4,784,486 | A | 11/1988 | Van Wagenen | 356/301 |
| 4,787,398 | A | 11/1988 | Garcia | 600/583 |
| 4,790,979 | A | 12/1988 | Terminiello | 422/56 |
| 4,794,926 | A | 1/1989 | Munsch et al. | 606/183 |
| 4,797,283 | A | 1/1989 | Allen | 424/443 |
| 4,814,142 | A | 3/1989 | Gleisner | 422/56 |
| 4,814,661 | A | 3/1989 | Ratzlaff | 310/328 |
| 4,817,603 | A | 4/1989 | Turner | 606/182 |
| 4,818,493 | A | 4/1989 | Coville | 422/102 |

(56) References Cited

U.S. PATENT DOCUMENTS

| | | | |
|---|---|---|---|
| 4,820,010 A | 4/1989 | Sciefres | 385/43 |
| 4,820,399 A | 4/1989 | Senda | 204/403 |
| 4,823,806 A | 4/1989 | Bajada | 600/557 |
| 4,824,639 A | 4/1989 | Hildenbrand | 422/56 |
| RE32,922 E | 5/1989 | Levin | 128/314 |
| 4,825,711 A | 5/1989 | Jensen | 73/865.8 |
| 4,827,763 A | 5/1989 | Bourland | 73/172 |
| 4,829,011 A | 5/1989 | Gibbons | 436/512 |
| 4,830,959 A | 5/1989 | McNeil | 435/53 |
| 4,836,904 A | 6/1989 | Armstrong | 204/294 |
| 4,840,893 A | 6/1989 | Hill | 435/6 |
| 4,844,095 A | 7/1989 | Chiodo | 128/314 |
| 4,845,392 A | 7/1989 | Mumbower | 310/14 |
| 4,850,973 A | 7/1989 | Jordan | 604/157 |
| 4,857,274 A | 8/1989 | Simon | 422/72 |
| 4,868,129 A | 9/1989 | Gibbons | 436/179 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,877,026 A | 10/1989 | de Laforcade | 128/305 |
| 4,882,013 A | 11/1989 | Turner | 204/1 |
| 4,883,055 A | 11/1989 | Merrick | 128/633 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,895,156 A | 1/1990 | Schulze | 600/342 |
| 4,897,173 A | 1/1990 | Nankai | 204/403 |
| 4,900,424 A | 2/1990 | Birch | 204/409 |
| 4,900,666 A | 2/1990 | Phillips | 435/25 |
| 4,911,794 A | 3/1990 | Parce | 204/1 T |
| 4,920,977 A | 5/1990 | Haynes | 128/770 |
| 4,924,879 A | 5/1990 | O'brien | 600/583 |
| 4,935,346 A | 6/1990 | Phillips et al. | 435/14 |
| 4,938,218 A | 7/1990 | Goodman | 128/633 |
| 4,940,468 A | 7/1990 | Petillo | 606/170 |
| 4,944,304 A | 7/1990 | Nishina | 128/667 |
| 4,945,045 A | 7/1990 | Forrest | 435/25 |
| 4,946,795 A | 8/1990 | Gibbons | 436/179 |
| 4,948,727 A | 8/1990 | Cass | 435/18 |
| 4,948,961 A | 8/1990 | Hillman | 250/252.1 |
| 4,952,373 A | 8/1990 | Sugarman | 422/99 |
| 4,952,515 A | 8/1990 | Gleisner | 436/169 |
| 4,953,552 A | 9/1990 | DeMarzo | 128/635 |
| 4,953,976 A | 9/1990 | Adler-Golden | 356/301 |
| 4,963,498 A | 10/1990 | Hillman | 436/69 |
| 4,966,581 A | 10/1990 | Landau | 604/72 |
| 4,966,646 A | 10/1990 | Zdeblick | 156/633 |
| 4,966,671 A | 10/1990 | Nylander | 204/153.14 |
| 4,975,581 A | 12/1990 | Robinson | 250/339 |
| 4,976,724 A | 12/1990 | Nieto | 606/182 |
| 4,977,910 A | 12/1990 | Miyahara | 134/7 |
| 4,983,178 A | 1/1991 | Schnell | 606/181 |
| 4,984,085 A | 1/1991 | Landowski | 358/213 |
| 4,990,154 A | 2/1991 | Brown | 606/182 |
| 4,995,402 A | 2/1991 | Smith | 600/584 |
| 4,999,582 A | 3/1991 | Parks | 324/438 |
| 5,001,054 A | 3/1991 | Wagner | 435/14 |
| 5,001,873 A | 3/1991 | Rufin | 451/39 |
| 5,004,923 A | 4/1991 | Hillman | 250/341 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413.02 |
| 5,026,388 A | 6/1991 | Ingalz | 606/182 |
| D318,331 S | 7/1991 | Phillips | D24/169 |
| 5,028,142 A | 7/1991 | Ostoich et al. | 366/273 |
| 5,029,583 A | 7/1991 | Meserol | 600/316 |
| 5,035,704 A | 7/1991 | Lambert | 606/182 |
| 5,039,617 A | 8/1991 | McDonald | 436/69 |
| 5,043,143 A | 8/1991 | Shaw | 422/65 |
| 5,046,496 A | 9/1991 | Betts | 600/352 |
| 5,047,044 A | 9/1991 | Smith | 606/182 |
| 5,049,373 A | 9/1991 | Ballou | 549/352 |
| 5,049,487 A | 9/1991 | Phillips | 435/4 |
| 5,054,487 A | 10/1991 | Clarke | 128/633 |
| 5,054,499 A | 10/1991 | Swierczek | 128/770 |
| 5,057,082 A | 10/1991 | Burchette, Jr. | 604/164 |
| 5,057,277 A | 10/1991 | Mauze | 422/56 |
| 5,059,394 A | 10/1991 | Phillips | 422/68.1 |
| 5,059,789 A | 10/1991 | Salcudean | 250/206.1 |
| 5,060,174 A | 10/1991 | Gross | 702/139 |
| 5,062,898 A | 11/1991 | McDermott | 134/7 |
| 5,064,411 A | 11/1991 | Gordon, III | 604/48 |
| 5,070,874 A | 12/1991 | Barnes | 128/633 |
| 5,070,886 A | 12/1991 | Mitchen | 128/771 |
| 5,073,500 A | 12/1991 | Saito et al. | 436/53 |
| 5,074,872 A | 12/1991 | Brown | 606/182 |
| 5,077,017 A | 12/1991 | Gorin | 422/100 |
| 5,077,199 A | 12/1991 | Basagni | 435/14 |
| 5,080,865 A | 1/1992 | Leiner | 422/68.1 |
| 5,086,229 A | 2/1992 | Rosenthal | 250/341 |
| 5,089,112 A | 2/1992 | Skotheim | 204/403 |
| 5,092,842 A | 3/1992 | Bechtold | 604/135 |
| 5,094,943 A | 3/1992 | Siedel | 435/25 |
| 5,096,669 A | 3/1992 | Lauks | 204/403.02 |
| 5,097,810 A | 3/1992 | Fishman | 600/556 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,382 A | 4/1992 | Brinkerhoff et al. | 604/164.12 |
| 5,104,619 A | 4/1992 | Castro | 422/56 |
| 5,104,813 A | 4/1992 | Besemer | 436/179 |
| 5,107,764 A | 4/1992 | Gasparrini | 101/425 |
| 5,108,564 A | 4/1992 | Szuminsky | 204/153.12 |
| 5,108,889 A | 4/1992 | Smith | 435/4 |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter et al. | 204/403 |
| 5,128,015 A | 7/1992 | Szuminsky | 204/403 |
| 5,128,171 A | 7/1992 | Gleisner | 427/2 |
| 5,132,801 A | 7/1992 | Yamano | 358/213 |
| 5,133,730 A | 7/1992 | Biro | 606/182 |
| 5,135,719 A | 8/1992 | Hillman | 422/101 |
| 5,139,685 A | 8/1992 | Castro | 210/767 |
| 5,140,161 A | 8/1992 | Hillman | 250/341 |
| 5,141,868 A | 8/1992 | Shanks | 435/288 |
| 5,144,139 A | 9/1992 | Hillman | 250/341 |
| 5,145,565 A | 9/1992 | Kater | 600/341 |
| 5,146,091 A | 9/1992 | Knudson | 250/341.6 |
| 5,152,296 A | 10/1992 | Simons | 128/670 |
| 5,152,775 A | 10/1992 | Ruppert | 606/182 |
| 5,153,671 A | 10/1992 | Miles | 356/301 |
| 5,156,611 A | 10/1992 | Haynes | 606/181 |
| 5,162,525 A | 11/1992 | Masilamani | 549/352 |
| 5,163,442 A | 11/1992 | Ono | 128/760 |
| 5,164,598 A | 11/1992 | Hillman | 250/341 |
| 5,167,619 A | 12/1992 | Wuchinich | 604/22 |
| 5,170,364 A | 12/1992 | Gross | 702/139 |
| 5,174,726 A | 12/1992 | Findlay | 417/205 |
| D332,490 S | 1/1993 | Brown | D24/146 |
| 5,178,142 A | 1/1993 | Harjunmaa | 128/633 |
| 5,179,005 A | 1/1993 | Phillips | 435/14 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,185,256 A | 2/1993 | Nankai | 435/174 |
| 5,187,100 A | 2/1993 | Matzinger | 436/16 |
| 5,188,118 A | 2/1993 | Terwilliger | 600/566 |
| 5,189,751 A | 3/1993 | Giuliani | 15/22.1 |
| 5,192,415 A | 3/1993 | Yoshioka | 204/403 |
| 5,194,391 A | 3/1993 | Mauze | 436/166 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,208,163 A | 5/1993 | Charlton et al. | 436/63 |
| 5,209,028 A | 5/1993 | McDermott | 51/426 |
| 5,211,652 A | 5/1993 | Derbyshire | 606/182 |
| 5,212,879 A | 5/1993 | Biro | 29/437 |
| 5,215,587 A | 6/1993 | McConnellogue | 118/699 |
| 5,216,597 A | 6/1993 | Beckers | 364/413.02 |
| 5,217,476 A | 6/1993 | Wishinsky | 606/167 |

(56) References Cited

U.S. PATENT DOCUMENTS

| | | | | |
|---|---|---|---|---|
| 5,217,480 A | 6/1993 | Haber | | 606/182 |
| 5,218,966 A | 6/1993 | Yamasawa | | 600/499 |
| 5,222,504 A | 6/1993 | Solomon | | 600/557 |
| 5,228,972 A | 7/1993 | Osaka | | 204/415 |
| 5,229,282 A | 7/1993 | Yoshioka | | 435/177 |
| 5,230,866 A | 7/1993 | Shartle | | 422/103 |
| 5,231,993 A | 8/1993 | Haber | | 128/770 |
| 5,241,969 A | 9/1993 | Carson | | 600/566 |
| 5,247,932 A | 9/1993 | Chung | | 128/633 |
| 5,249,583 A | 10/1993 | Mallaby | | 600/567 |
| 5,250,066 A | 10/1993 | Lambert | | 606/181 |
| 5,251,126 A | 10/1993 | Kahn | | 364/413.11 |
| 5,253,656 A | 10/1993 | Rincoe | | 128/782 |
| 5,256,998 A | 10/1993 | Becker | | 335/229 |
| 5,264,103 A | 11/1993 | Yoshioka | | 204/403 |
| 5,264,105 A | 11/1993 | Gregg | | 204/403 |
| 5,264,106 A | 11/1993 | McAleer | | 204/403 |
| 5,266,179 A | 11/1993 | Nankai | | 204/401 |
| 5,266,359 A | 11/1993 | Spielvogel | | 427/388.4 |
| D342,573 S | 12/1993 | Cerola | | D24/147 |
| 5,267,974 A | 12/1993 | Lambert | | 604/195 |
| 5,272,087 A | 12/1993 | El Murr | | 435/291 |
| 5,277,181 A | 1/1994 | Mendelson | | 128/633 |
| 5,279,294 A | 1/1994 | Anderson | | 600/322 |
| 5,279,791 A | 1/1994 | Aldrich | | 422/58 |
| 5,282,822 A | 2/1994 | Macors | | 606/182 |
| 5,286,362 A | 2/1994 | Hoenes | | 204/403 |
| 5,286,364 A | 2/1994 | Yacynych | | 204/418 |
| 5,288,636 A | 2/1994 | Pollmann | | 435/288 |
| 5,294,261 A | 3/1994 | McDermott | | 134/7 |
| 5,296,378 A | 3/1994 | Sakata | | 436/63 |
| 5,300,779 A | 4/1994 | Hillman | | 250/341 |
| 5,304,192 A | 4/1994 | Crouse | | 606/181 |
| 5,304,193 A | 4/1994 | Zhadanov | | 606/182 |
| 5,304,347 A | 4/1994 | Mann | | 422/67 |
| 5,304,468 A | 4/1994 | Phillips | | 435/14 |
| 5,306,623 A | 4/1994 | Kiser | | 435/14 |
| 5,307,263 A | 4/1994 | Brown | | 600/301 |
| 5,312,590 A | 5/1994 | Gunasingham | | 422/56 |
| 5,314,441 A | 5/1994 | Cusack | | 606/182 |
| 5,314,442 A | 5/1994 | Morita | | 606/182 |
| 5,315,793 A | 5/1994 | Peterson | | 451/2 |
| 5,316,012 A | 5/1994 | Siegal | | 128/744 |
| 5,318,583 A | 6/1994 | Rabenau | | 606/182 |
| 5,318,584 A | 6/1994 | Lange | | 606/182 |
| 5,320,607 A | 6/1994 | Ishibashi | | 604/115 |
| 5,320,808 A | 6/1994 | Holen | | 422/64 |
| 5,324,302 A | 6/1994 | Crouse | | 606/181 |
| 5,324,303 A | 6/1994 | Strong | | 606/181 |
| 5,330,634 A | 7/1994 | Wong | | 205/777.5 |
| 5,332,479 A | 7/1994 | Uenoyama | | 204/153.12 |
| 5,341,206 A | 8/1994 | Pittaro | | 356/301 |
| 5,342,382 A | 8/1994 | Brinkerhoff | | 606/184 |
| 5,344,703 A | 9/1994 | Kovar | | 428/312.6 |
| 5,350,392 A | 9/1994 | Purcell | | 606/182 |
| 5,352,351 A | 10/1994 | White | | 204/406 |
| 5,354,287 A | 10/1994 | Wacks | | 604/232 |
| 5,354,447 A | 10/1994 | Uenoyama | | 204/403 |
| 5,356,420 A | 10/1994 | Czernecki | | 606/182 |
| 5,360,410 A | 11/1994 | Wacks | | 604/232 |
| 5,365,699 A | 11/1994 | Armstrong | | 451/7 |
| 5,366,469 A | 11/1994 | Steg | | 606/182 |
| 5,366,470 A | 11/1994 | Ramel | | 606/183 |
| 5,366,609 A | 11/1994 | White | | 204/403 |
| 5,368,047 A | 11/1994 | Suzuki | | 600/578 |
| 5,370,509 A | 12/1994 | Golding | | 417/423.1 |
| 5,371,687 A | 12/1994 | Holmes | | 364/514 |
| 5,372,135 A | 12/1994 | Mendelson | | 600/322 |
| 5,375,397 A | 12/1994 | Ferrand | | 54/66 |
| 5,378,628 A | 1/1995 | Gratzel | | 435/288 |
| 5,382,346 A | 1/1995 | Uenoyama | | 204/403 |
| 5,383,885 A | 1/1995 | Bland | | 606/182 |
| 5,389,534 A | 2/1995 | Gentzkow | | 435/180 |
| 5,390,450 A | 2/1995 | Goenka | | 451/39 |
| 5,393,903 A | 2/1995 | Gratzel | | 556/137 |
| 5,395,339 A | 3/1995 | Talonn | | 604/111 |
| 5,395,387 A | 3/1995 | Burns | | 606/181 |
| 5,397,334 A | 3/1995 | Schenk | | 606/182 |
| 5,401,376 A | 3/1995 | Foos | | 204/415 |
| 5,402,798 A | 4/1995 | Swierczek | | 128/770 |
| 5,405,283 A | 4/1995 | Goenka | | 451/39 |
| 5,405,510 A | 4/1995 | Betts | | 205/782 |
| 5,405,511 A | 4/1995 | White | | 204/153.1 |
| 5,407,545 A | 4/1995 | Hirose | | 204/153.12 |
| 5,407,554 A | 4/1995 | Saurer | | 204/403 |
| 5,407,818 A | 4/1995 | Genetzkow | | 435/180 |
| 5,409,583 A | 4/1995 | Yoshioka | | 204/153.12 |
| 5,409,664 A | 4/1995 | Allen | | 422/56 |
| 5,410,059 A | 4/1995 | Fraser | | 546/10 |
| 5,410,474 A | 4/1995 | Fox | | 600/300 |
| 5,415,169 A | 5/1995 | Siczek | | 600/427 |
| 5,418,142 A | 5/1995 | Kiser | | 435/14 |
| 5,423,847 A | 6/1995 | Strong et al. | | 606/182 |
| 5,424,545 A | 6/1995 | Block | | 350/343 |
| 5,426,032 A | 6/1995 | Phillips | | 435/14 |
| 5,436,161 A | 7/1995 | Bergstrom | | 435/291 |
| 5,437,999 A | 8/1995 | Diebold | | 435/288 |
| 5,438,271 A | 8/1995 | White | | 324/444 |
| 5,443,701 A | 8/1995 | Willner | | 204/153 |
| 5,445,920 A | 8/1995 | Saito | | 430/311 |
| D362,719 S | 9/1995 | Kaplan | | D24/147 |
| 5,453,360 A | 9/1995 | Yu | | 435/28 |
| 5,454,828 A | 10/1995 | Schraga | | 606/181 |
| 5,456,875 A | 10/1995 | Lambert | | 264/328.1 |
| 5,459,325 A | 10/1995 | Hueton | | 250/458.1 |
| 5,460,182 A | 10/1995 | Goodman | | 600/342 |
| 5,462,533 A | 10/1995 | Daugherty | | 604/164 |
| 5,464,418 A | 11/1995 | Schraga | | 606/182 |
| 5,465,722 A | 11/1995 | Fort | | 600/447 |
| 5,471,102 A | 11/1995 | Becker | | 310/50 |
| 5,472,427 A | 12/1995 | Rammler | | 604/164.01 |
| 5,474,084 A | 12/1995 | Cunniff | | 600/557 |
| 5,476,474 A | 12/1995 | Davis | | 606/182 |
| 5,480,387 A | 1/1996 | Gabriel | | 604/134 |
| 5,487,748 A | 1/1996 | Marshall | | 606/182 |
| D367,109 S | 2/1996 | Ryner | | D24/224 |
| 5,490,505 A | 2/1996 | Diab | | 600/323 |
| 5,496,274 A | 3/1996 | Graves | | 604/86 |
| 5,496,453 A | 3/1996 | Uenoyama | | 205/777.5 |
| 5,498,542 A | 3/1996 | Corey | | 435/283.1 |
| 5,501,836 A | 3/1996 | Myerson | | 42/57 |
| 5,501,893 A | 3/1996 | Laermer | | 428/161 |
| 5,507,288 A | 4/1996 | Bocker | | 128/633 |
| 5,507,629 A | 4/1996 | Jarvik | | 417/423.3 |
| 5,508,171 A | 4/1996 | Walling | | 205/777.5 |
| 5,509,410 A | 4/1996 | Hill | | 128/637 |
| 5,510,266 A | 4/1996 | Bonner et al. | | 436/43 |
| 5,512,159 A | 4/1996 | Yoshioka | | 204/403 |
| 5,514,152 A | 5/1996 | Smith | | 606/182 |
| 5,515,170 A | 5/1996 | Matzinger | | 356/423 |
| 5,518,006 A | 5/1996 | Mawhirt | | 128/770 |
| D371,198 S | 6/1996 | Savage | | D24/169 |
| 5,524,636 A | 6/1996 | Sarvazyan | | 128/774 |
| 5,525,511 A | 6/1996 | D'Costa | | 435/287.9 |
| 5,525,518 A | 6/1996 | Lundsgaard | | 436/68 |
| 5,526,120 A | 6/1996 | Jina | | 356/446 |
| 5,527,333 A | 6/1996 | Nikkels | | 606/182 |
| 5,527,334 A | 6/1996 | Kanner | | 606/182 |
| 5,529,074 A | 6/1996 | Greenfield | | 600/557 |
| 5,540,676 A | 7/1996 | Freiberg | | 606/3 |
| 5,540,709 A | 7/1996 | Ramel | | 606/183 |
| 5,543,326 A | 8/1996 | Heller | | 435/287.9 |
| 5,545,174 A | 8/1996 | Schenk | | 606/182 |
| 5,545,291 A | 8/1996 | Smith | | 438/107 |
| 5,547,702 A | 8/1996 | Gleisner | | 427/2.13 |
| D373,419 S | 9/1996 | Muramatsu | | D24/165 |
| 5,554,153 A | 9/1996 | Costello | | 606/9 |
| 5,554,166 A | 9/1996 | Lange | | 606/182 |
| 5,558,834 A | 9/1996 | Chu | | 422/55 |
| 5,562,384 A | 10/1996 | Alvite | | 414/226.01 |
| 5,562,696 A | 10/1996 | Nobles | | 606/185 |
| 5,563,031 A | 10/1996 | Yu | | 435/4 |
| 5,563,042 A | 10/1996 | Phillips | | 435/14 |
| 5,569,286 A | 10/1996 | Peckham | | 606/181 |

(56) References Cited

U.S. PATENT DOCUMENTS

| | | | |
|---|---|---|---|
| 5,569,287 A | 10/1996 | Tezuka | 606/182 |
| 5,571,132 A | 11/1996 | Mawhirt | 606/182 |
| 5,575,284 A | 11/1996 | Athan | 600/323 |
| 5,575,403 A | 11/1996 | Charlton | 221/31 |
| 5,575,895 A | 11/1996 | Ikeda | 204/403 |
| 5,582,697 A | 12/1996 | Ikeda | 204/403 |
| 5,584,846 A | 12/1996 | Mawhirt | 606/181 |
| 5,591,139 A | 1/1997 | Lin | 604/264 |
| 5,593,852 A | 1/1997 | Heller | 435/14 |
| 5,599,501 A | 2/1997 | Carey | 422/64 |
| 5,605,837 A | 2/1997 | Karimi | 436/14 |
| D378,612 S | 3/1997 | Clark | D24/169 |
| 5,608,006 A | 3/1997 | Myerson | 525/54.1 |
| 5,609,749 A | 3/1997 | Yamauchi | 205/777.5 |
| 5,611,809 A | 3/1997 | Marshall | 606/181 |
| 5,611,810 A | 3/1997 | Arnold | 606/185 |
| 5,613,978 A | 3/1997 | Harding | 606/181 |
| 5,616,135 A | 4/1997 | Thorne | 604/192 |
| 5,617,851 A | 4/1997 | Lipkovker | 600/573 |
| 5,618,297 A | 4/1997 | Hart | 606/185 |
| 5,620,579 A | 4/1997 | Genshaw et al. | 204/402 |
| 5,620,863 A | 4/1997 | Tomasco | 435/14 |
| 5,624,458 A | 4/1997 | Lipscher | 606/181 |
| 5,624,459 A | 4/1997 | Kortenbach | 606/185 |
| 5,624,537 A | 4/1997 | Turner | 204/403 |
| D379,516 S | 5/1997 | Rutter | D24/146 |
| 5,628,764 A | 5/1997 | Schraga | 606/182 |
| 5,628,765 A | 5/1997 | Morita | 606/182 |
| 5,628,890 A | 5/1997 | Carter | 204/403 |
| 5,628,961 A | 5/1997 | Davis | 422/63 |
| 5,630,828 A | 5/1997 | Mawhirt | 606/187 |
| 5,630,986 A | 5/1997 | Charlton | 422/64 |
| 5,632,410 A | 5/1997 | Moulton | 221/79 |
| 5,640,954 A | 6/1997 | Pfeiffer | 128/635 |
| D381,591 S | 7/1997 | Rice | D10/81 |
| 5,643,306 A | 7/1997 | Schraga | 606/182 |
| 5,643,308 A | 7/1997 | Markman | 606/187 |
| 5,645,555 A | 7/1997 | Davis | 606/182 |
| 5,647,851 A | 7/1997 | Pokras | 604/131 |
| 5,650,062 A | 7/1997 | Ikeda | 205/778 |
| 5,653,863 A | 8/1997 | Genshaw | 205/777.5 |
| 5,657,760 A | 8/1997 | Ying | 128/660.03 |
| 5,658,444 A | 8/1997 | Black | 204/415 |
| 5,660,791 A | 8/1997 | Brenneman | 422/58 |
| D383,550 S | 9/1997 | Larson | D24/225 |
| 5,662,127 A | 9/1997 | De Vaughn | 128/765 |
| 5,662,672 A | 9/1997 | Pambianchi | 606/181 |
| 5,666,966 A | 9/1997 | Horie | 128/760 |
| 5,676,143 A | 10/1997 | Simonsen | 128/633 |
| 5,678,306 A | 10/1997 | Bozeman | 29/888.025 |
| 5,680,858 A | 10/1997 | Hansen et al. | 128/635 |
| 5,680,872 A | 10/1997 | Sesekura | 128/760 |
| 5,682,233 A | 10/1997 | Brinda | 356/246 |
| 5,682,884 A | 11/1997 | Hill | 128/637 |
| 5,683,562 A | 11/1997 | Schaffar | 204/403 |
| 5,691,898 A | 11/1997 | Rosenberg | 700/85 |
| 5,692,514 A | 12/1997 | Bowman | 600/504 |
| 5,695,947 A | 12/1997 | Guo | 435/11 |
| 5,700,695 A | 12/1997 | Yassinzadeh | 436/180 |
| 5,705,045 A | 1/1998 | Park | 204/403 |
| 5,707,384 A | 1/1998 | Kim | 606/181 |
| 5,708,247 A | 1/1998 | McAleer | 204/403 |
| 5,709,668 A | 1/1998 | Wacks | 604/232 |
| 5,709,699 A | 1/1998 | Warner | 606/181 |
| 5,710,011 A | 1/1998 | Forrow | 435/25 |
| 5,714,123 A | 2/1998 | Sohrab | 422/99 |
| 5,714,390 A | 2/1998 | Hallowitz | 436/526 |
| 5,719,034 A | 2/1998 | Kiser | 435/14 |
| 5,720,862 A | 2/1998 | Hamamoto | 204/403 |
| 5,720,924 A | 2/1998 | Eikmeier | 422/102 |
| D392,391 S | 3/1998 | Douglas | D24/225 |
| D392,740 S | 3/1998 | Yung | D24/169 |
| 5,723,284 A | 3/1998 | Ye | 435/4 |
| 5,727,548 A | 3/1998 | Hill | 128/637 |
| 5,729,905 A | 3/1998 | Mathiasmeier | 33/3 R |
| 5,730,753 A | 3/1998 | Morita | 606/181 |
| 5,733,085 A | 3/1998 | Shida | 411/442 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,735,868 A | 4/1998 | Lee | 606/189 |
| 5,736,103 A | 4/1998 | Pugh | 422/68.1 |
| 5,738,244 A | 4/1998 | Charlton | 221/26 |
| 5,741,228 A | 4/1998 | Lambrecht | 604/93 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,746,761 A | 5/1998 | Turchin | 606/181 |
| 5,746,898 A | 5/1998 | Preidel | 204/403 |
| 5,753,429 A | 5/1998 | Pugh | 435/4 |
| 5,753,452 A | 5/1998 | Smith | 435/14 |
| 5,755,228 A | 5/1998 | Wilson | 600/459 |
| 5,755,733 A | 5/1998 | Morita | 606/182 |
| 5,758,643 A | 6/1998 | Wong | 600/309 |
| 5,759,364 A | 6/1998 | Charlton | 204/403 |
| 5,762,770 A | 6/1998 | Pritchard | 204/403 |
| 5,770,086 A | 6/1998 | Indriksons | 210/643 |
| 5,770,369 A | 6/1998 | Meade | 435/6 |
| 5,772,586 A | 6/1998 | Heinonen | 600/300 |
| 5,772,677 A | 6/1998 | Mawhirt | 606/181 |
| 5,773,270 A | 6/1998 | D'Orazio | 435/177 |
| 5,776,157 A | 7/1998 | Thorne | 606/182 |
| 5,776,719 A | 7/1998 | Douglas | 435/28 |
| 5,779,365 A | 7/1998 | Takaki | 374/161 |
| 5,780,304 A | 7/1998 | Matzinger | 436/169 |
| 5,782,770 A | 7/1998 | Mooradian | 600/476 |
| 5,782,852 A | 7/1998 | Foggia | 606/182 |
| 5,788,651 A | 8/1998 | Weilandt | 600/567 |
| 5,788,652 A | 8/1998 | Rahn | 600/577 |
| 5,789,255 A | 8/1998 | Yu | 536/95 |
| 5,794,219 A | 8/1998 | Brown | 705/37 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin | 422/73 |
| 5,801,057 A | 9/1998 | Smart | 436/68 |
| 5,807,375 A | 9/1998 | Gross | 604/890.1 |
| 5,810,199 A | 9/1998 | Charlton | 221/31 |
| D399,566 S | 10/1998 | Sohrab | D24/169 |
| 5,820,551 A | 10/1998 | Hill | 600/347 |
| 5,822,715 A | 10/1998 | Worthington | 702/19 |
| 5,823,973 A | 10/1998 | Racchini | 600/573 |
| 5,824,491 A | 10/1998 | Priest | 435/28 |
| 5,827,181 A | 10/1998 | Dias | 600/322 |
| 5,828,943 A | 10/1998 | Brown | 434/258 |
| 5,829,589 A | 11/1998 | Nguyen | 206/366 |
| 5,830,219 A | 11/1998 | Bird et al. | 606/130 |
| 5,832,448 A | 11/1998 | Brown | 705/2 |
| 5,840,020 A | 11/1998 | Heinonen | 600/309 |
| 5,840,171 A | 11/1998 | Birch | 205/335 |
| 5,843,691 A | 12/1998 | Douglas | 435/14 |
| 5,843,692 A | 12/1998 | Phillips | 435/14 |
| 5,846,216 A | 12/1998 | Gonzales | 604/2 |
| 5,846,486 A | 12/1998 | Pugh | 422/56 |
| 5,846,490 A | 12/1998 | Yokota | 422/66 |
| 5,849,174 A | 12/1998 | Sanghera | 205/775 |
| 5,853,373 A | 12/1998 | Griffith | 600/554 |
| 5,854,074 A | 12/1998 | Charlton | 436/46 |
| D403,975 S | 1/1999 | Douglas et al. | D10/81 |
| 5,855,377 A | 1/1999 | Murphy | 279/50 |
| 5,855,801 A | 1/1999 | Lin | 216/2 |
| 5,856,174 A | 1/1999 | Lipshutz | 435/286.5 |
| 5,856,195 A | 1/1999 | Charlton | 436/50 |
| 5,857,967 A | 1/1999 | Frid | 600/301 |
| 5,857,983 A | 1/1999 | Douglas | 600/538 |
| 5,858,804 A | 1/1999 | Zanzucchi | 506/9 |
| 5,860,922 A | 1/1999 | Gordon | 600/431 |
| 5,863,800 A | 1/1999 | Eikmeier | 436/48 |
| 5,866,353 A | 2/1999 | Berneth | 435/26 |
| 5,868,135 A | 2/1999 | Kaufman | 128/630 |
| 5,868,772 A | 2/1999 | LeVaughn | 606/181 |

(56) References Cited

U.S. PATENT DOCUMENTS

| | | | |
|---|---|---|---|
| 5,869,972 A | 2/1999 | Birch | 324/439 |
| 5,871,494 A | 2/1999 | Simons | 606/181 |
| 5,872,713 A | 2/1999 | Douglas | 702/85 |
| 5,873,887 A | 2/1999 | King | 606/182 |
| 5,876,351 A | 3/1999 | Rohde | 600/523 |
| 5,876,957 A | 3/1999 | Douglas | 435/28 |
| 5,879,163 A | 3/1999 | Brown | 434/236 |
| 5,879,310 A | 3/1999 | Sopp | 600/578 |
| 5,879,311 A | 3/1999 | Duchon | 600/583 |
| 5,879,373 A | 3/1999 | Roeper | 606/344 |
| 5,880,829 A | 3/1999 | Kauhaniemi | 356/246 |
| 5,882,494 A | 3/1999 | Van Antwerp | 204/403 |
| 5,885,211 A | 3/1999 | Eppstein | 600/309 |
| 5,886,056 A | 3/1999 | Hershkowitz | 518/703 |
| 5,887,133 A | 3/1999 | Brown | 395/200.3 |
| 5,890,128 A | 3/1999 | Diaz | 705/2 |
| RE36,191 E | 4/1999 | Solomon | 395/308 |
| 5,891,053 A | 4/1999 | Sesekura | 600/583 |
| 5,892,569 A | 4/1999 | Van de Velde | 351/221 |
| 5,893,848 A | 4/1999 | Negus | 606/41 |
| 5,893,870 A | 4/1999 | Talen | 606/201 |
| 5,897,493 A | 4/1999 | Brown | 600/300 |
| 5,897,569 A | 4/1999 | Kellogg | 606/169 |
| 5,899,855 A | 5/1999 | Brown | 600/301 |
| 5,899,915 A | 5/1999 | Saadat | 606/170 |
| 5,900,130 A | 5/1999 | Benvegnu | 204/453 |
| 5,902,731 A | 5/1999 | Ouyang | 435/26 |
| 5,906,921 A | 5/1999 | Ikeda | 435/25 |
| D411,619 S | 6/1999 | Duchon | D24/146 |
| 5,908,416 A | 6/1999 | Costello | 606/9 |
| 5,911,937 A | 6/1999 | Hekal | 264/255 |
| 5,912,134 A | 6/1999 | Shartle | 435/7.24 |
| 5,913,310 A | 6/1999 | Brown | 128/897 |
| 5,916,156 A | 6/1999 | Hildenbrand | 600/347 |
| 5,916,229 A | 6/1999 | Evans | 606/171 |
| 5,916,230 A | 6/1999 | Brenneman | 606/172 |
| 5,918,603 A | 7/1999 | Brown | 128/897 |
| 5,919,711 A | 7/1999 | Boyd | 436/178 |
| 5,921,963 A | 7/1999 | Erez | 604/192 |
| 5,922,188 A | 7/1999 | Ikeda | 204/777.5 |
| 5,922,530 A | 7/1999 | Yu | 435/4 |
| 5,922,591 A | 7/1999 | Anderson | 435/287.2 |
| RE36,268 E | 8/1999 | Szuminsky | 205/777.5 |
| 5,931,794 A | 8/1999 | Pitesky | 600/556 |
| 5,933,136 A | 8/1999 | Brown | 345/327 |
| 5,935,075 A | 8/1999 | Casscells et al. | 600/474 |
| 5,938,635 A | 8/1999 | Kuhle | 604/506 |
| 5,938,679 A | 8/1999 | Freeman | 606/181 |
| 5,940,153 A | 8/1999 | Castaneda | 349/58 |
| 5,942,102 A | 8/1999 | Hodges | 205/775 |
| 5,942,189 A | 8/1999 | Wolfbeis | 422/82.08 |
| 5,947,957 A | 9/1999 | Morris | 606/13 |
| 5,951,300 A | 9/1999 | Brown | 434/236 |
| 5,951,492 A | 9/1999 | Douglas | 600/583 |
| 5,951,493 A | 9/1999 | Douglas et al. | 600/583 |
| 5,951,582 A | 9/1999 | Thorne | 606/182 |
| 5,951,836 A | 9/1999 | McAleer | 204/403 |
| 5,954,738 A | 9/1999 | LeVaughn | 606/181 |
| 5,956,501 A | 9/1999 | Brown | 395/500.32 |
| 5,957,846 A | 9/1999 | Chiang | 600/447 |
| 5,958,199 A | 9/1999 | Miyamoto | 204/403 |
| 5,959,098 A | 9/1999 | Goldberg | 536/25.3 |
| 5,960,403 A | 9/1999 | Brown | 705/2 |
| 5,961,451 A | 10/1999 | Reber | 600/322 |
| 5,964,718 A | 10/1999 | Duchon | 600/583 |
| 5,965,380 A | 10/1999 | Heller | 435/14 |
| 5,968,063 A | 10/1999 | Chu | 606/185 |
| 5,968,760 A | 10/1999 | Phillips | 435/14 |
| 5,968,836 A | 10/1999 | Matzinger | 436/169 |
| 5,971,941 A | 10/1999 | Simons | 606/573 |
| 5,972,199 A | 10/1999 | Heller | 205/777.5 |
| 5,972,294 A | 10/1999 | Smith | 422/58 |
| 5,972,715 A | 10/1999 | Celentano | 436/164 |
| 5,974,124 A | 10/1999 | Schlueter | 379/106.2 |
| 5,976,085 A | 11/1999 | Kimball | 600/309 |
| 5,983,193 A | 11/1999 | Heinonen | 705/2 |
| 5,985,116 A | 11/1999 | Ikeda | 204/403 |
| 5,985,559 A | 11/1999 | Brown | 435/6 |
| 5,986,754 A | 11/1999 | Harding | 356/246 |
| 5,993,400 A | 11/1999 | Rincoe | 600/595 |
| 5,993,434 A | 11/1999 | Dev | 604/501 |
| D417,504 S | 12/1999 | Love | D24/169 |
| 5,997,476 A | 12/1999 | Brown | 600/300 |
| 5,997,561 A | 12/1999 | Boecker | 606/182 |
| 5,997,817 A | 12/1999 | Crismore | 422/58 |
| 5,997,818 A | 12/1999 | Hacker | 422/681 |
| 6,001,067 A | 12/1999 | Shults | 600/584 |
| 6,007,497 A | 12/1999 | Huitema | 600/567 |
| D418,602 S | 1/2000 | Prokop | D24/169 |
| 6,014,577 A | 1/2000 | Henning | 600/345 |
| 6,015,392 A | 1/2000 | Douglas | 600/583 |
| 6,018,289 A | 1/2000 | Sekura | 340/309.4 |
| 6,020,110 A | 2/2000 | Williams | 430/315 |
| 6,022,324 A | 2/2000 | Skinner | 600/566 |
| 6,022,366 A | 2/2000 | Schraga | 606/181 |
| 6,022,748 A | 2/2000 | Charych | 436/527 |
| 6,023,629 A | 2/2000 | Tamada | 600/347 |
| 6,023,686 A | 2/2000 | Brown | 705/37 |
| 6,027,459 A | 2/2000 | Shain | 600/573 |
| 6,030,399 A | 2/2000 | Ignotz | 606/167 |
| 6,030,827 A | 2/2000 | Davis | 435/287 |
| 6,030,967 A | 2/2000 | Marui | 514/215 |
| 6,032,059 A | 2/2000 | Henning | 600/345 |
| 6,032,119 A | 2/2000 | Brown | 705/2 |
| 6,033,421 A | 3/2000 | Theiss | 606/186 |
| 6,033,866 A | 3/2000 | Guo | 435/14 |
| 6,036,924 A | 3/2000 | Simons | 422/100 |
| 6,037,178 A | 3/2000 | Leiner | 436/50 |
| 6,041,253 A | 3/2000 | Kost | 604/20 |
| 6,045,567 A | 4/2000 | Taylor | 606/181 |
| 6,046,055 A | 4/2000 | Wolfbeis | 436/172 |
| 6,048,352 A | 4/2000 | Douglas | 606/181 |
| D424,696 S | 5/2000 | Ray | D24/169 |
| 6,056,701 A | 5/2000 | Duchon | 600/583 |
| 6,059,815 A | 5/2000 | Lee | 606/209 |
| 6,060,327 A | 5/2000 | Keen | 436/518 |
| 6,061,128 A | 5/2000 | Zweig | 356/243.4 |
| 6,063,039 A | 5/2000 | Cunningham | 600/573 |
| 6,066,103 A | 5/2000 | Duchon | 600/583 |
| 6,066,243 A | 5/2000 | Anderson | 422/82.01 |
| 6,066,296 A | 5/2000 | Brady | 422/63 |
| 6,067,463 A | 5/2000 | Jeng | 600/336 |
| 6,068,615 A | 5/2000 | Brown | 604/207 |
| D426,638 S | 6/2000 | Ray | D24/169 |
| 6,070,761 A | 6/2000 | Bloom | 222/81 |
| 6,071,249 A | 6/2000 | Cunningham | 600/578 |
| 6,071,250 A | 6/2000 | Douglas | 600/583 |
| 6,071,251 A | 6/2000 | Cunningham | 600/584 |
| 6,071,294 A | 6/2000 | Simons | 606/181 |
| 6,071,391 A | 6/2000 | Gotoh | 204/403 |
| 6,074,360 A | 6/2000 | Haar et al. | 604/57 |
| 6,077,408 A | 6/2000 | Miyamoto | 204/403 |
| 6,080,106 A | 6/2000 | Lloyd | 600/300 |
| 6,080,172 A | 6/2000 | Fujiwara | 606/166 |
| D428,150 S | 7/2000 | Ruf | D24/146 |
| 6,083,196 A | 7/2000 | Trautman | 604/46 |
| 6,083,710 A | 7/2000 | Heller | 435/14 |
| 6,084,660 A | 7/2000 | Shartle | 356/39 |
| 6,085,576 A | 7/2000 | Sunshine | 73/29.01 |
| 6,086,544 A | 7/2000 | Hibner | 600/568 |
| 6,086,545 A | 7/2000 | Roe | 600/570 |
| 6,086,562 A | 7/2000 | Jacobsen | 604/156 |
| 6,090,078 A | 7/2000 | Erskine | 604/198 |
| 6,091,975 A | 7/2000 | Daddona | 600/345 |
| 6,093,146 A | 7/2000 | Filangeri | 600/300 |
| 6,093,156 A | 7/2000 | Cunningham et al. | 600/573 |
| D428,993 S | 8/2000 | Lubs | D24/165 |
| 6,099,484 A | 8/2000 | Douglas | 600/583 |
| 6,099,802 A | 8/2000 | Pugh | 422/58 |
| 6,100,107 A | 8/2000 | Lei | 438/50 |
| 6,101,478 A | 8/2000 | Brown | 705/2 |
| 6,102,933 A | 8/2000 | Lee | 606/209 |
| 6,103,033 A | 8/2000 | Say | 156/73.1 |
| 6,103,509 A | 8/2000 | Sode | 435/190 |

(56) References Cited

U.S. PATENT DOCUMENTS

| | | | | |
|---|---|---|---|---|
| 6,104,940 A | 8/2000 | Watanabe | | 600/345 |
| 6,106,751 A | 8/2000 | Talbot | | 264/81 |
| 6,107,083 A | 8/2000 | Collins | | 435/288 |
| 6,113,578 A | 9/2000 | Brown | | 604/207 |
| 6,117,115 A | 9/2000 | Hill et al. | | 606/189 |
| 6,117,630 A | 9/2000 | Reber | | 435/4 |
| 6,118,126 A | 9/2000 | Zanzucchi | | 250/458.1 |
| 6,119,033 A | 9/2000 | Spigelman | | 600/426 |
| 6,120,462 A | 9/2000 | Hibner | | 600/566 |
| 6,120,676 A | 9/2000 | Heller | | 205/777.5 |
| 6,121,009 A | 9/2000 | Heller | | 435/14 |
| 6,122,536 A | 9/2000 | Sun | | 600/341 |
| 6,126,804 A | 10/2000 | Andresen | | 204/601 |
| 6,126,899 A | 10/2000 | Woudenberg | | 422/50 |
| 6,129,823 A | 10/2000 | Hughes | | 204/403.01 |
| 6,132,449 A | 10/2000 | Lum | | 606/181 |
| 6,133,837 A | 10/2000 | Riley | | 340/573.1 |
| 6,134,461 A | 10/2000 | Say | | 600/345 |
| 6,136,013 A | 10/2000 | Marshall | | 606/167 |
| 6,139,562 A | 10/2000 | Mauze | | 606/171 |
| 6,143,164 A | 11/2000 | Heller | | 600/583 |
| 6,144,837 A | 11/2000 | Quy | | 434/307 R |
| 6,144,976 A | 11/2000 | Silva et al. | | 708/100 |
| 6,149,203 A | 11/2000 | Hanlon | | 283/72 |
| 6,151,586 A | 11/2000 | Brown | | 705/14 |
| 6,152,875 A | 11/2000 | Hakamata | | 600/319 |
| 6,152,942 A | 11/2000 | Brenneman | | 606/181 |
| 6,153,069 A | 11/2000 | Pottgen | | 204/403 |
| RE36,991 E | 12/2000 | Yamamoto | | 204/403 |
| 6,155,267 A | 12/2000 | Nelson | | 128/899 |
| 6,155,992 A | 12/2000 | Henning et al. | | 600/583 |
| 6,156,051 A | 12/2000 | Schraga | | 606/181 |
| 6,157,442 A | 12/2000 | Raskas | | 356/39 |
| 6,159,147 A | 12/2000 | Lichter | | 600/300 |
| 6,159,424 A | 12/2000 | Kauhaniemi | | 422/63 |
| 6,161,095 A | 12/2000 | Brown | | 705/2 |
| 6,162,397 A | 12/2000 | Jurik | | 422/56 |
| 6,162,611 A | 12/2000 | Heller | | 435/14 |
| 6,167,362 A | 12/2000 | Brown | | 703/11 |
| 6,167,386 A | 12/2000 | Brown | | 705/37 |
| 6,168,563 B1 | 1/2001 | Brown | | 600/301 |
| 6,168,957 B1 | 1/2001 | Matzinger | | 436/518 |
| 6,171,325 B1 | 1/2001 | Mauze et al. | | 606/171 |
| 6,172,743 B1 | 1/2001 | Kley et al. | | 356/39 |
| 6,175,752 B1 | 1/2001 | Say | | 600/345 |
| 6,176,847 B1 | 1/2001 | Humphreys | | 604/246 |
| 6,176,865 B1 | 1/2001 | Mauze | | 606/171 |
| 6,177,000 B1 | 1/2001 | Peterson | | 205/777.5 |
| 6,177,931 B1 | 1/2001 | Alexander | | 725/52 |
| 6,183,489 B1 | 2/2001 | Douglas | | 606/181 |
| 6,186,145 B1 | 2/2001 | Brown | | 128/897 |
| 6,190,612 B1 | 2/2001 | Berger | | 422/82.07 |
| 6,191,852 B1 | 2/2001 | Paffhausen | | 356/244 |
| 6,192,891 B1 | 2/2001 | Gravel | | 128/920 |
| 6,193,673 B1 | 2/2001 | Viola | | 600/568 |
| 6,193,873 B1 | 2/2001 | Ohara | | 205/792 |
| 6,194,900 B1 | 2/2001 | Freeman | | 324/321 |
| 6,197,040 B1 | 3/2001 | LeVaughn | | 606/182 |
| 6,197,257 B1 | 3/2001 | Raskas | | 422/82.05 |
| 6,200,773 B1 | 3/2001 | Ouyang | | 435/26 |
| 6,203,504 B1 | 3/2001 | Latterell | | 600/576 |
| 6,206,841 B1 | 3/2001 | Cunningham et al. | | 600/584 |
| 6,210,133 B1 | 4/2001 | Aboul-Hosn | | 417/423.1 |
| 6,210,272 B1 | 4/2001 | Brown | | 463/1 |
| 6,210,369 B1 | 4/2001 | Wilmot | | 604/157 |
| 6,210,420 B1 | 4/2001 | Mauze | | 606/182 |
| 6,210,421 B1 | 4/2001 | Bocker | | 606/182 |
| 6,212,417 B1 | 4/2001 | Ikeda | | 204/403.14 |
| 6,214,626 B1 | 4/2001 | Meller | | 436/165 |
| 6,214,804 B1 | 4/2001 | Felgner | | 514/44 |
| 6,218,571 B1 | 4/2001 | Zheng | | 562/61 |
| 6,219,574 B1 | 4/2001 | Cormier | | 604/20 |
| 6,221,023 B1 | 4/2001 | Matsuba | | 600/486 |
| 6,221,238 B1 | 4/2001 | Grundig | | 205/777.5 |
| 6,224,617 B1 | 5/2001 | Saadat et al. | | 606/170 |
| 6,225,078 B1 | 5/2001 | Ikeda | | 435/25 |
| 6,228,100 B1 | 5/2001 | Schraga | | 606/183 |
| 6,230,051 B1 | 5/2001 | Cormier | | 604/20 |
| 6,230,501 B1 | 5/2001 | Bailey | | 62/51.1 |
| 6,231,531 B1 | 5/2001 | Lum | | 601/46 |
| 6,233,471 B1 | 5/2001 | Berner | | 600/345 |
| 6,233,539 B1 | 5/2001 | Brown | | 703/11 |
| 6,234,772 B1 | 5/2001 | Wampler | | 417/423.12 |
| 6,240,393 B1 | 5/2001 | Brown | | 705/1 |
| D444,235 S | 6/2001 | Roberts | | D24/169 |
| 6,241,862 B1 | 6/2001 | McAleer | | 204/403 |
| 6,242,207 B1 | 6/2001 | Douglas | | 435/25 |
| 6,245,060 B1 | 6/2001 | Loomis | | 606/9 |
| 6,245,215 B1 | 6/2001 | Douglas | | 205/775 |
| 6,246,992 B1 | 6/2001 | Brown | | 705/2 |
| 6,248,065 B1 | 6/2001 | Brown | | 600/300 |
| 6,251,083 B1 | 6/2001 | Yum | | 600/584 |
| 6,251,121 B1 | 6/2001 | Saadat | | 606/180 |
| 6,251,260 B1 | 6/2001 | Heller | | 205/777.5 |
| 6,251,344 B1 | 6/2001 | Goldstein | | 422/123 |
| D444,557 S | 7/2001 | Levaughn | | D24/146 |
| 6,254,831 B1 | 7/2001 | Barnard | | 422/82.08 |
| 6,256,533 B1 | 7/2001 | Vuzhakov | | 604/21 |
| 6,258,111 B1 | 7/2001 | Ross | | 606/171 |
| 6,258,229 B1 | 7/2001 | Winarta | | 204/403 |
| 6,258,254 B1 | 7/2001 | Miyamoto | | 205/777.5 |
| 6,261,241 B1 | 7/2001 | Burbank | | 600/564 |
| 6,261,245 B1 | 7/2001 | Kawai | | 600/576 |
| 6,261,519 B1 | 7/2001 | Harding | | 422/58 |
| 6,264,635 B1 | 7/2001 | Wampler | | 604/151 |
| 6,268,161 B1 | 7/2001 | Han | | 435/14 |
| 6,268,162 B1 | 7/2001 | Phillips | | 435/14 |
| 6,269,314 B1 | 7/2001 | Iitawaki | | 702/23 |
| 6,270,455 B1 | 8/2001 | Brown | | 600/300 |
| 6,270,637 B1 | 8/2001 | Crismore | | 204/403 |
| 6,272,359 B1 | 8/2001 | Kivela | | 455/567 |
| 6,272,364 B1 | 8/2001 | Kurnik | | 600/345 |
| 6,275,717 B1 | 8/2001 | Gross | | 600/345 |
| 6,280,254 B1 | 8/2001 | Wu | | 439/630 |
| 6,281,006 B1 | 8/2001 | Heller | | 435/287.9 |
| 6,283,926 B1 | 9/2001 | Cunningham et al. | | 600/573 |
| 6,283,982 B1 | 9/2001 | Levaughn | | 606/172 |
| 6,284,478 B1 | 9/2001 | Heller | | 435/14 |
| 6,285,448 B1 | 9/2001 | Kuenstner | | 356/39 |
| 6,285,454 B1 | 9/2001 | Douglas | | 356/446 |
| 6,289,254 B1 | 9/2001 | Shimizu | | 700/96 |
| 6,290,683 B1 | 9/2001 | Erez | | 604/273 |
| 6,294,897 B1 | 9/2001 | Champlin | | 320/153 |
| 6,295,506 B1 | 9/2001 | Heinonen | | 702/104 |
| 6,299,578 B1 | 10/2001 | Kurnik | | 600/309 |
| 6,299,596 B1 | 10/2001 | Ding | | 604/96.01 |
| 6,299,757 B1 | 10/2001 | Feldman | | 205/775 |
| 6,302,844 B1 | 10/2001 | Walker | | 600/300 |
| 6,302,855 B1 | 10/2001 | Lav | | 600/584 |
| 6,305,804 B1 | 10/2001 | Rice | | 351/221 |
| 6,306,104 B1 | 10/2001 | Cunningham | | 600/573 |
| 6,306,152 B1 | 10/2001 | Verdonk | | 606/182 |
| 6,306,347 B1 | 10/2001 | Mason | | 422/58 |
| 6,309,351 B1 | 10/2001 | Kurnik | | 600/309 |
| 6,309,535 B1 | 10/2001 | Williams | | 205/777.5 |
| 6,312,612 B1 | 11/2001 | Sherman | | 216/2 |
| 6,315,738 B1 | 11/2001 | Nishikawa | | 600/583 |
| 6,318,970 B1 | 11/2001 | Backhouse | | 417/92 |
| 6,319,210 B1 | 11/2001 | Douglas | | 600/583 |
| 6,322,574 B1 | 11/2001 | Lloyd | | 606/181 |
| 6,322,808 B1 | 11/2001 | Trautman | | 424/448 |
| 6,322,963 B1 | 11/2001 | Bauer | | 435/4 |
| 6,329,161 B1 | 12/2001 | Heller | | 435/14 |
| 6,330,426 B2 | 12/2001 | Brown | | 434/307 R |
| 6,331,163 B1 | 12/2001 | Kaplan | | 600/486 |
| 6,332,871 B1 | 12/2001 | Douglas | | 600/583 |
| 6,334,363 B1 | 1/2002 | Testud | | 73/862 |
| 6,334,778 B1 | 1/2002 | Brown | | 434/258 |
| 6,334,856 B1 | 1/2002 | Allen | | 604/191 |
| 6,335,203 B1 | 1/2002 | Patel | | 436/169 |
| 6,335,376 B1 | 1/2002 | Allen, III et al. | | 604/191 |
| 6,336,900 B1 | 1/2002 | Alleckson | | 600/485 |
| 6,338,790 B1 | 1/2002 | Feldman | | 205/777.5 |
| 6,346,120 B1 | 2/2002 | Yamazaki | | 623/3.13 |

(56) References Cited

U.S. PATENT DOCUMENTS

| | | |
|---|---|---|
| 6,349,229 B1 | 2/2002 | Watanabe .................... 600/345 |
| 6,350,273 B1 | 2/2002 | Minagawa .................... 606/186 |
| 6,350,451 B1 | 2/2002 | Horn ........................ 424/184.1 |
| 6,352,514 B1 | 3/2002 | Douglas ...................... 600/583 |
| 6,352,523 B1 | 3/2002 | Brown ........................ 604/207 |
| 6,353,753 B1 | 3/2002 | Flock ......................... 600/473 |
| 6,364,889 B1 | 4/2002 | Kheiri et al. ................. 606/181 |
| 6,364,890 B1 | 4/2002 | Lum ........................... 606/181 |
| 6,368,273 B1 | 4/2002 | Brown ........................ 600/300 |
| 6,375,469 B1 | 4/2002 | Brown ........................ 434/236 |
| 6,375,626 B1 | 4/2002 | Allen et al. .................. 600/584 |
| 6,375,627 B1 | 4/2002 | Mauze ........................ 600/584 |
| 6,379,301 B1 | 4/2002 | Worthington ................ 600/309 |
| 6,379,317 B1 | 4/2002 | Kintzig ....................... 600/573 |
| 6,379,324 B1 | 4/2002 | Gartstein ...................... 604/22 |
| 6,379,969 B1 | 4/2002 | Mauze ......................... 436/68 |
| 6,381,577 B1 | 4/2002 | Brown ........................... 705/2 |
| D456,910 S | 5/2002 | Clark ........................ D24/225 |
| 6,387,709 B1 | 5/2002 | Mason ........................ 436/164 |
| 6,391,005 B1 | 5/2002 | Lum ........................... 604/117 |
| 6,395,227 B1 | 5/2002 | Kiser .......................... 422/56 |
| 6,398,522 B2 | 6/2002 | Skill ......................... 417/410.3 |
| 6,398,562 B1 | 6/2002 | Butler .......................... 439/91 |
| 6,399,394 B1 | 6/2002 | Dahm ......................... 436/180 |
| 6,402,701 B1 | 6/2002 | Kaplan ....................... 600/567 |
| 6,402,704 B1 | 6/2002 | Mcmorrow ................. 600/576 |
| 6,409,740 B1 | 6/2002 | Kuhr .......................... 606/182 |
| 6,413,410 B1 | 7/2002 | Hodges ....................... 205/775 |
| 6,413,411 B1 | 7/2002 | Pottgen ..................... 205/777.5 |
| 6,415,821 B2 | 7/2002 | Kamholz ..................... 137/827 |
| 6,420,128 B1 | 7/2002 | Ouyang ........................ 435/14 |
| 6,421,633 B1 | 7/2002 | Heinonen ..................... 703/11 |
| 6,423,014 B1 | 7/2002 | Churchill ..................... 600/587 |
| 6,428,664 B1 | 8/2002 | Bhullar .................... 204/403.03 |
| 6,436,055 B1 | 8/2002 | Roe ............................ 600/584 |
| 6,436,256 B1 | 8/2002 | Williams ................. 204/403.14 |
| 6,436,721 B1 | 8/2002 | Kuo ............................ 436/514 |
| 6,440,645 B1 | 8/2002 | Yon-Hin ...................... 430/322 |
| 6,444,115 B1 | 9/2002 | Hodges ....................... 205/792 |
| 6,447,119 B1 | 9/2002 | Stewart et al. ............... 351/212 |
| 6,447,265 B1 | 9/2002 | Antaki ........................ 417/354 |
| 6,451,040 B1 | 9/2002 | Purcell ........................ 606/181 |
| 6,453,810 B1 | 9/2002 | Rossmeisl .................... 101/123 |
| 6,458,258 B2 | 10/2002 | Taniike ....................... 204/403 |
| 6,461,496 B1 | 10/2002 | Feldman ................... 205/777.5 |
| 6,462,162 B2 | 10/2002 | Van Antwerp ................. 528/77 |
| 6,464,649 B1 | 10/2002 | Duchon ....................... 600/583 |
| 6,471,903 B2 | 10/2002 | Sherman ...................... 264/328.1 |
| 6,472,220 B1 | 10/2002 | Simons ......................... 436/63 |
| 6,475,360 B1 | 11/2002 | Hodges .................... 204/403.14 |
| 6,475,372 B1 | 11/2002 | Ohara ....................... 205/777.5 |
| 6,475,436 B1 | 11/2002 | Schabbach .................... 422/64 |
| 6,475,750 B1 | 11/2002 | Han et al. ...................... 435/14 |
| 6,477,394 B2 | 11/2002 | Rice ............................ 600/318 |
| 6,477,424 B1 | 11/2002 | Thompson .................... 607/60 |
| 6,484,046 B1 | 11/2002 | Say ............................. 600/345 |
| 6,485,439 B1 | 11/2002 | Roe ............................. 600/578 |
| 6,485,461 B1 | 11/2002 | Mason ......................... 604/132 |
| 6,485,923 B1 | 11/2002 | Yani ............................. 435/14 |
| 6,488,827 B1 | 12/2002 | Shartle ........................ 204/403 |
| 6,488,872 B1 | 12/2002 | Beebe et al. .................... 264/31 |
| 6,488,891 B2 | 12/2002 | Mason ......................... 422/58 |
| 6,489,133 B2 | 12/2002 | Phillips ........................ 435/14 |
| 6,491,709 B2 | 12/2002 | Sharma ........................ 606/181 |
| 6,491,870 B2 | 12/2002 | Patel ........................... 422/58 |
| 6,494,830 B1 | 12/2002 | Wessel ........................ 600/300 |
| 6,497,845 B1 | 12/2002 | Sacherer ...................... 422/104 |
| 6,501,404 B2 | 12/2002 | Walker ........................ 341/143 |
| 6,501,976 B1 | 12/2002 | Sohrab ........................ 600/347 |
| 6,503,210 B1 | 1/2003 | Hirao .......................... 600/576 |
| 6,503,231 B1 | 1/2003 | Prausnitz .................... 604/272 |
| 6,503,290 B1 | 1/2003 | Jarosinski ..................... 75/252 |
| 6,503,381 B1 | 1/2003 | Gotoh .................... 204/403.14 |
| 6,506,165 B1 | 1/2003 | Sweeney ..................... 600/562 |
| 6,506,168 B1 | 1/2003 | Fathallah ..................... 600/578 |
| 6,506,575 B1 | 1/2003 | Knappe ......................... 435/25 |
| 6,508,795 B1 | 1/2003 | Samuelsson ................. 604/113 |
| 6,512,986 B1 | 1/2003 | Harmon ........................ 702/84 |
| 6,514,270 B1 | 2/2003 | Schraga ....................... 606/182 |
| 6,514,460 B1 | 2/2003 | Fendrock ...................... 422/55 |
| 6,519,241 B1 | 2/2003 | Theimer ....................... 370/338 |
| 6,520,326 B2 | 2/2003 | McIvor ........................ 206/305 |
| 6,521,110 B1 | 2/2003 | Hodges .................... 204/403.14 |
| 6,521,182 B1 | 2/2003 | Shartle ......................... 422/58 |
| 6,527,521 B2 | 3/2003 | Noda ........................... 417/355 |
| 6,527,716 B1 | 3/2003 | Epstein ........................ 600/309 |
| 6,527,778 B2 | 3/2003 | Athanasiou .................... 606/80 |
| 6,529,377 B1 | 3/2003 | Nelson ......................... 361/699 |
| 6,530,892 B1 | 3/2003 | Kelly ........................... 600/583 |
| 6,530,937 B1 | 3/2003 | Schraga ....................... 606/182 |
| 6,531,322 B1 | 3/2003 | Jurik ............................ 436/95 |
| 6,533,949 B1 | 3/2003 | Yeshurun ....................... 216/11 |
| 6,537,207 B1 | 3/2003 | Rice ............................ 600/121 |
| 6,537,242 B1 | 3/2003 | Palmer ......................... 604/22 |
| 6,537,264 B1 | 3/2003 | Cormier et al. .............. 604/506 |
| 6,537,292 B1 | 3/2003 | Lee ............................. 606/182 |
| 6,540,672 B1 | 4/2003 | Simonsen ..................... 600/300 |
| 6,540,675 B2 | 4/2003 | Aceti .......................... 600/309 |
| 6,540,762 B1 | 4/2003 | Bertling ....................... 606/182 |
| 6,540,891 B1 | 4/2003 | Stewart .................... 204/403.14 |
| 6,541,266 B2 | 4/2003 | Modzelewski ................. 436/95 |
| 6,547,954 B2 | 4/2003 | Ikeda ....................... 205/777.5 |
| 6,549,796 B2 | 4/2003 | Sohrab ........................ 600/345 |
| 6,551,494 B1 | 4/2003 | Heller ....................... 205/777.5 |
| 6,553,244 B2 | 4/2003 | Lesho ......................... 600/347 |
| 6,554,381 B2 | 4/2003 | Locher ........................... 347/7 |
| 6,555,061 B1 | 4/2003 | Leong .......................... 422/58 |
| D475,136 S | 5/2003 | Taniguchi .................... D24/165 |
| 6,558,320 B1 | 5/2003 | Causey ........................ 600/300 |
| 6,558,361 B1 | 5/2003 | Yeshurun ..................... 604/272 |
| 6,558,402 B1 | 5/2003 | Chelak ......................... 606/182 |
| 6,558,528 B1 | 5/2003 | Matzinger .................. 205/777.5 |
| 6,560,471 B1 | 5/2003 | Heller ......................... 600/347 |
| 6,561,978 B1 | 5/2003 | Conn ........................... 600/309 |
| 6,561,989 B2 | 5/2003 | Whitson ....................... 600/573 |
| 6,562,210 B1 | 5/2003 | Bhullar ..................... 204/403.3 |
| 6,565,509 B1 | 5/2003 | Say ............................. 600/365 |
| 6,565,808 B2 | 5/2003 | Hudak .......................... 422/58 |
| 6,569,157 B1 | 5/2003 | Shain ........................... 606/12 |
| 6,571,651 B1 | 6/2003 | Hodges ...................... 73/864.72 |
| 6,572,566 B2 | 6/2003 | Effenhauser ................. 600/584 |
| 6,572,822 B2 | 6/2003 | Jurik ............................ 422/56 |
| 6,574,490 B2 | 6/2003 | Abbink ........................ 600/316 |
| 6,575,905 B2 | 6/2003 | Knobbe ........................ 600/365 |
| 6,576,101 B1 | 6/2003 | Heller ...................... 204/403.14 |
| 6,576,117 B1 | 6/2003 | Iketaki et al. .............. 205/777.5 |
| 6,576,416 B2 | 6/2003 | Haviland ....................... 435/4 |
| 6,579,690 B1 | 6/2003 | Bonnecaze et al. ............ 435/14 |
| 6,582,573 B2 | 6/2003 | Douglas .................... 204/403.1 |
| 6,584,338 B1 | 6/2003 | Van Muiswinkel ........... 600/419 |
| D477,670 S | 7/2003 | Jurik ........................... D24/225 |
| 6,586,199 B2 | 7/2003 | Ouyang ......................... 435/26 |
| 6,587,705 B1 | 7/2003 | Kim ............................ 600/347 |
| 6,589,260 B1 | 7/2003 | Schmelzeisen ............... 606/181 |
| 6,589,261 B1 | 7/2003 | Abulhaj ....................... 606/181 |
| 6,591,124 B2 | 7/2003 | Sherman et al. .............. 600/345 |
| 6,591,125 B1 | 7/2003 | Buse ........................... 600/347 |
| 6,592,744 B1 | 7/2003 | Hodges ........................ 205/775 |
| 6,592,745 B1 | 7/2003 | Feldman ................... 205/777.5 |
| 6,595,919 B2 | 7/2003 | Berner ......................... 600/365 |
| 6,599,407 B2 | 7/2003 | Taniike ..................... 204/403.1 |
| 6,599,693 B2 | 7/2003 | Webb ............................ 435/4 |
| 6,599,769 B2 | 7/2003 | Kondo .......................... 438/28 |
| 6,601,534 B2 | 8/2003 | Hebrank ........................ 119/6.8 |
| 6,602,205 B1 | 8/2003 | Erickson ...................... 600/573 |
| 6,602,268 B2 | 8/2003 | Kuhr ........................... 606/181 |
| 6,602,678 B2 | 8/2003 | Kwon ........................... 435/14 |
| 6,604,050 B2 | 8/2003 | Trippel ........................ 702/19 |
| 6,607,362 B2 | 8/2003 | Lum ............................ 417/53 |
| 6,607,494 B1 | 8/2003 | Fowler ........................ 600/570 |
| 6,607,658 B1 | 8/2003 | Heller ...................... 205/777.5 |
| 6,612,111 B1 | 9/2003 | Hodges ......................... 60/593 |
| 6,616,616 B2 | 9/2003 | Fritz ............................ 600/583 |
| 6,616,819 B1 | 9/2003 | Liamos .................... 204/403.02 |

(56) References Cited

U.S. PATENT DOCUMENTS

| | | | | |
|---|---|---|---|---|
| 6,618,934 | B1 | 9/2003 | Feldman | 29/830 |
| 6,620,112 | B2 | 9/2003 | Klitmose | 600/583 |
| 6,620,310 | B1 | 9/2003 | Ohara | 205/792 |
| 6,623,501 | B2 | 9/2003 | Heller | 606/181 |
| 6,626,851 | B2 | 9/2003 | Hirao | 600/576 |
| 6,632,349 | B1 | 10/2003 | Hodges | 205/792 |
| 6,635,222 | B2 | 10/2003 | Kent | 422/22 |
| 6,638,415 | B1 | 10/2003 | Hodges | 205/775 |
| 6,638,772 | B1 | 10/2003 | Douglas | 436/518 |
| 6,641,533 | B2 | 11/2003 | Causey | 600/300 |
| 6,645,142 | B2 | 11/2003 | Braig | 600/300 |
| 6,645,219 | B2 | 11/2003 | Roe | 606/182 |
| 6,645,368 | B1 | 11/2003 | Beaty | 205/792 |
| 6,649,416 | B1 | 11/2003 | Kauer | 436/164 |
| 6,650,915 | B2 | 11/2003 | Routt | 600/319 |
| 6,652,720 | B1 | 11/2003 | Mansouri | 204/403.11 |
| 6,652,734 | B1 | 11/2003 | Hodges | 205/777.5 |
| 6,652,814 | B1 | 11/2003 | House | 422/104 |
| D484,600 | S | 12/2003 | Kaar | D24/169 |
| 6,656,428 | B1 | 12/2003 | Clark et al. | 422/404 |
| 6,656,697 | B1 | 12/2003 | Ouyang | 435/7.9 |
| 6,656,702 | B1 | 12/2003 | Yugawa | 435/26 |
| 6,659,966 | B2 | 12/2003 | Essenpreis | 600/583 |
| 6,660,018 | B2 | 12/2003 | Lum | 606/181 |
| 6,662,439 | B1 | 12/2003 | Bhullar | 29/825 |
| 6,669,669 | B2 | 12/2003 | Flaherty | 604/132 |
| 6,671,527 | B2 | 12/2003 | Peterson | 600/316 |
| D484,980 | S | 1/2004 | Hartwein | D24/165 |
| 6,673,617 | B2 | 1/2004 | Patel | 436/8 |
| 6,676,995 | B2 | 1/2004 | Dick | 427/286 |
| 6,679,841 | B2 | 1/2004 | Bojan | 600/309 |
| 6,679,852 | B1 | 1/2004 | Schmelzeisen-Redeker et al. | 600/583 |
| 6,682,933 | B2 | 1/2004 | Patel | 436/8 |
| 6,689,411 | B2 | 2/2004 | Dick | 427/2.13 |
| 6,706,000 | B2 | 3/2004 | Perez | 600/583 |
| 6,706,049 | B2 | 3/2004 | Moerman | 606/181 |
| 6,706,159 | B2 | 3/2004 | Moerman | 204/403.03 |
| 6,706,232 | B2 | 3/2004 | Hasegawa | 264/403.09 |
| 6,709,692 | B2 | 3/2004 | Sudor | 427/2.1 |
| 6,713,660 | B1 | 3/2004 | Roe | 604/361 |
| 6,716,577 | B1 | 4/2004 | Yu | 435/6 |
| 6,719,887 | B2 | 4/2004 | Hasegawa | 204/403.09 |
| 6,719,923 | B2 | 4/2004 | Stiene | 252/511 |
| 6,721,586 | B2 | 4/2004 | Kiser | 600/345 |
| 6,723,046 | B2 | 4/2004 | Lichtenstein | 600/300 |
| 6,723,111 | B2 | 4/2004 | Abulhaj | 606/181 |
| 6,723,371 | B2 | 4/2004 | Chih-hui | 472/2.13 |
| 6,723,500 | B2 | 4/2004 | Yu | 435/4 |
| 6,726,818 | B2 | 4/2004 | Cui | 204/403.1 |
| 6,729,546 | B2 | 5/2004 | Roustaei | 235/462.45 |
| 6,730,494 | B1 | 5/2004 | Toranto | 435/28 |
| 6,731,966 | B1 | 5/2004 | Spigelman | 600/407 |
| 6,733,493 | B2 | 5/2004 | Gruzdev | 606/9 |
| 6,736,777 | B2 | 5/2004 | Kim | 600/365 |
| 6,738,654 | B2 | 5/2004 | Sohrab | 600/345 |
| 6,740,215 | B1 | 5/2004 | Nakaminami et al. | 204/403.14 |
| 6,743,211 | B1 | 6/2004 | Prausnitz | 604/239 |
| 6,743,597 | B1 | 6/2004 | Guo | 435/14 |
| 6,743,635 | B2 | 6/2004 | Neel | 436/95 |
| 6,746,872 | B2 | 6/2004 | Zheng | 436/16 |
| 6,749,618 | B2 | 6/2004 | Levaughn | 606/182 |
| 6,749,740 | B2 | 6/2004 | Liamos | 205/792 |
| 6,749,792 | B2 | 6/2004 | Olson | 264/328.1 |
| 6,749,887 | B1 | 6/2004 | Dick | 427/2.13 |
| 6,751,491 | B2 | 6/2004 | Lew | 600/345 |
| 6,752,817 | B2 | 6/2004 | Flora | 606/181 |
| 6,753,187 | B2 | 6/2004 | Cizdziel | 436/169 |
| 6,759,190 | B2 | 7/2004 | Lin | 435/4 |
| 6,764,496 | B2 | 7/2004 | Schraga | 606/182 |
| 6,764,581 | B1 | 7/2004 | Forrow | 204/403 |
| 6,767,441 | B1 | 7/2004 | Cai | 204/403.03 |
| 6,773,671 | B1 | 8/2004 | Lewis | 422/58 |
| 6,776,888 | B2 | 8/2004 | Yamamoto | 204/403.06 |
| 6,780,645 | B2 | 8/2004 | Hayter | 436/8 |
| 6,780,647 | B2 | 8/2004 | Fujiwara | 436/169 |
| 6,783,502 | B2 | 8/2004 | Orloff | 600/583 |
| 6,783,537 | B1 | 8/2004 | Kuhr | 606/182 |
| 6,784,274 | B2 | 8/2004 | Van Antwerp | 528/77 |
| 6,786,874 | B2 | 9/2004 | Grace | 600/573 |
| 6,787,013 | B2 | 9/2004 | Chang | 204/412 |
| 6,787,109 | B2 | 9/2004 | Haar | 422/82.05 |
| 6,790,327 | B2 | 9/2004 | Ikeda | 204/403.1 |
| 6,790,599 | B1 | 9/2004 | Madou | 430/320 |
| 6,792,791 | B2 | 9/2004 | Sato | 73/1.02 |
| 6,793,632 | B2 | 9/2004 | Sohrab | 600/573 |
| 6,793,633 | B2 | 9/2004 | Douglas | 600/583 |
| 6,793,802 | B2 | 9/2004 | Lee | 205/777.5 |
| 6,797,150 | B2 | 9/2004 | Kermani | 205/777.5 |
| 6,800,488 | B2 | 10/2004 | Khan | 436/166 |
| 6,801,041 | B2 | 10/2004 | Karinka | 324/444 |
| 6,801,804 | B2 | 10/2004 | Miller | 604/20 |
| 6,802,199 | B2 | 10/2004 | Hilgers | 72/370.1 |
| 6,802,811 | B1 | 10/2004 | Slepian | 600/309 |
| 6,802,957 | B2 | 10/2004 | Jung | 205/777.5 |
| 6,805,780 | B1 | 10/2004 | Ryu | 204/403.01 |
| 6,808,499 | B1 | 10/2004 | Churchill | 600/587 |
| 6,808,908 | B2 | 10/2004 | Yao | 435/181 |
| 6,808,937 | B2 | 10/2004 | Ligler | 436/518 |
| 6,809,807 | B1 | 10/2004 | Erickson | 356/213 |
| 6,811,406 | B2 | 11/2004 | Grube | 439/66 |
| 6,811,557 | B2 | 11/2004 | Schraga | 606/182 |
| 6,811,659 | B2 | 11/2004 | Vachon | 204/224 |
| 6,811,753 | B2 | 11/2004 | Hirao | 422/101 |
| 6,811,792 | B2 | 11/2004 | Roser | 424/423 |
| 6,812,031 | B1 | 11/2004 | Carlsson | 436/52 |
| 6,814,843 | B1 | 11/2004 | Bhullar | 204/403.01 |
| 6,814,844 | B2 | 11/2004 | Bhullar | 204/403.1 |
| 6,814,845 | B2 | 11/2004 | Wilson | 204/486 |
| 6,815,186 | B2 | 11/2004 | Clark | 435/183 |
| 6,816,742 | B2 | 11/2004 | Kim | 600/345 |
| 6,818,180 | B2 | 11/2004 | Douglas | 422/58 |
| 6,821,483 | B2 | 11/2004 | Phillips | 422/58 |
| 6,823,750 | B2 | 11/2004 | Hodges | 73/864.72 |
| 6,825,047 | B1 | 11/2004 | Woudenberg | 436/518 |
| 6,827,250 | B2 | 12/2004 | Uhland | 228/110.1 |
| 6,827,829 | B2 | 12/2004 | Kawanaka | 204/403.02 |
| 6,829,507 | B1 | 12/2004 | Lidman | 607/19 |
| 6,830,551 | B1 | 12/2004 | Uchigaki | 600/584 |
| 6,830,668 | B2 | 12/2004 | Musho | 204/400 |
| 6,830,669 | B2 | 12/2004 | Miyazaki | 204/409 |
| 6,830,934 | B1 | 12/2004 | Harding | 436/166 |
| 6,833,540 | B2 | 12/2004 | MacKenzie | 250/214 |
| 6,835,184 | B1 | 12/2004 | Sage | 604/46 |
| 6,835,553 | B2 | 12/2004 | Han | 435/14 |
| 6,835,570 | B2 | 12/2004 | Patel | 436/8 |
| 6,837,858 | B2 | 1/2005 | Cunningham | 600/573 |
| 6,837,976 | B2 | 1/2005 | Cai | 204/403.14 |
| 6,837,988 | B2 | 1/2005 | Leong | 205/792 |
| 6,840,912 | B2 | 1/2005 | Kloepfer | 600/583 |
| 6,841,052 | B2 | 1/2005 | Musho | 204/401 |
| 6,843,254 | B2 | 1/2005 | Tapper | 128/898 |
| 6,843,902 | B1 | 1/2005 | Penner | 205/76 |
| 6,844,149 | B2 | 1/2005 | Goldman | 435/4 |
| 6,847,451 | B2 | 1/2005 | Pugh | 356/436 |
| 6,849,052 | B2 | 2/2005 | Uchigaki et al. | 600/584 |
| 6,849,168 | B2 | 2/2005 | Crumly | 204/416 |
| 6,849,216 | B2 | 2/2005 | Rappin | 264/134 |
| 6,849,456 | B2 | 2/2005 | Patel | 436/8 |
| 6,850,790 | B2 | 2/2005 | Berner | 600/347 |
| 6,852,119 | B1 | 2/2005 | Abulhaj | 606/182 |
| 6,852,212 | B2 | 2/2005 | Maxwell | 205/775 |
| 6,852,500 | B1 | 2/2005 | Hoss | 435/14 |
| 6,853,854 | B1 | 2/2005 | Proniewicz | 600/319 |
| 6,855,243 | B2 | 2/2005 | Khan | 205/777.5 |
| 6,856,125 | B2 | 2/2005 | Kermani | 324/71.1 |
| 6,856,928 | B2 | 2/2005 | Harmon | 702/84 |
| 6,858,015 | B2 | 2/2005 | List | 600/583 |
| 6,858,401 | B2 | 2/2005 | Phillips | 435/14 |
| 6,859,738 | B2 | 2/2005 | Bush | 702/25 |
| 6,862,466 | B2 | 3/2005 | Ackerman | 600/347 |
| 6,862,534 | B2 | 3/2005 | Sterling | 702/23 |
| 6,863,800 | B2 | 3/2005 | Karinka | 205/777.5 |
| 6,863,801 | B2 | 3/2005 | Hodges | 205/792 |

(56) References Cited

U.S. PATENT DOCUMENTS

| | | | | |
|---|---|---|---|---|
| 6,865,408 | B1 | 3/2005 | Abbink | 600/310 |
| 6,866,641 | B2 | 3/2005 | Marshall | 600/583 |
| 6,866,675 | B2 | 3/2005 | Perez | 606/181 |
| 6,866,758 | B2 | 3/2005 | Bhullar | 204/403.2 |
| 6,866,822 | B1 | 3/2005 | House | 422/82.05 |
| 6,869,418 | B2 | 3/2005 | Marano-Ford | 604/192 |
| 6,872,200 | B2 | 3/2005 | Mann | 604/890.1 |
| 6,872,297 | B2 | 3/2005 | Mansouri | 205/775 |
| 6,872,298 | B2 | 3/2005 | Kermani | 205/777.5 |
| 6,872,299 | B2 | 3/2005 | Kermani | 205/777.5 |
| 6,872,358 | B2 | 3/2005 | Hagen | 422/61 |
| 6,875,208 | B2 | 4/2005 | Santini | 604/890.1 |
| 6,875,223 | B2 | 4/2005 | Argauer | 606/181 |
| 6,875,327 | B1 | 4/2005 | Miyazaki | 204/403.14 |
| 6,875,613 | B2 | 4/2005 | Shartle | 436/63 |
| 6,878,120 | B2 | 4/2005 | Roe | 600/583 |
| 6,878,251 | B2 | 4/2005 | Hodges | 204/403.14 |
| 6,878,255 | B1 | 4/2005 | Wang | 204/452 |
| 6,878,262 | B2 | 4/2005 | Taniike | 205/777.5 |
| 6,880,968 | B1 | 4/2005 | Haar | 374/131 |
| 6,881,203 | B2 | 4/2005 | Delmore | 604/272 |
| 6,881,322 | B2 | 4/2005 | Tokunaga | 205/775 |
| 6,881,378 | B1 | 4/2005 | Zimmer | 422/58 |
| 6,881,541 | B2 | 4/2005 | Petersen | 435/6 |
| 6,881,550 | B2 | 4/2005 | Phillips | 435/14 |
| 6,881,551 | B2 | 4/2005 | Heller | 435/14 |
| 6,881,578 | B2 | 4/2005 | Otake | 436/44 |
| 6,882,940 | B2 | 4/2005 | Potts | 702/23 |
| 6,884,592 | B2 | 4/2005 | Matzinger | 435/7.1 |
| 6,885,196 | B2 | 4/2005 | Taniike | 324/444 |
| 6,885,883 | B2 | 4/2005 | Parris | 600/347 |
| 6,887,202 | B2 | 5/2005 | Currie | 600/309 |
| 6,887,239 | B2 | 5/2005 | Elstrom | 606/41 |
| 6,887,253 | B2 | 5/2005 | Schraga | 606/181 |
| 6,887,426 | B2 | 5/2005 | Phillips | 422/56 |
| 6,887,709 | B2 | 5/2005 | Leong | 436/8 |
| 6,889,069 | B2 | 5/2005 | Routt | 600/319 |
| 6,890,319 | B1 | 5/2005 | Crocker | 604/131 |
| 6,890,421 | B2 | 5/2005 | Ohara | 205/777.5 |
| 6,890,484 | B2 | 5/2005 | Bautista | 422/58 |
| 6,891,936 | B2 | 5/2005 | Kai | 379/106.02 |
| 6,892,085 | B2 | 5/2005 | McIvor | 600/347 |
| 6,893,396 | B2 | 5/2005 | Schulze | 600/300 |
| 6,893,545 | B2 | 5/2005 | Gotoh | 204/403.5 |
| 6,893,552 | B1 | 5/2005 | Wang | 205/777.5 |
| 6,895,263 | B2 | 5/2005 | Shin | 600/316 |
| 6,895,264 | B2 | 5/2005 | Rice | 600/319 |
| 6,895,265 | B2 | 5/2005 | Silver | 600/345 |
| 6,896,793 | B2 | 5/2005 | Erdosy | 205/775 |
| 6,897,788 | B2 | 5/2005 | Khair | 340/870.16 |
| 6,902,905 | B2 | 6/2005 | Burson | 435/14 |
| 6,904,301 | B2 | 6/2005 | Raskas | 600/310 |
| 6,905,733 | B2 | 6/2005 | Russell | 427/393.5 |
| 6,908,008 | B2 | 6/2005 | Pugh | 221/135 |
| 6,908,535 | B2 | 6/2005 | Rankin | 204/406 |
| 6,908,591 | B2 | 6/2005 | MacPhee | 422/22 |
| 6,908,593 | B1 | 6/2005 | Shartle | 422/58 |
| 6,911,130 | B2 | 6/2005 | Brenneman | 204/400 |
| 6,911,131 | B2 | 6/2005 | Miyazaki | 204/403.14 |
| 6,911,621 | B2 | 6/2005 | Bhullar | 219/121.69 |
| 6,911,937 | B1 | 6/2005 | Sparrow | 342/188 |
| 6,913,210 | B2 | 7/2005 | Baasch | 239/407 |
| 6,913,668 | B2 | 7/2005 | Matzinger | 156/256 |
| 6,916,410 | B2 | 7/2005 | Katsuki | 204/403 |
| 6,918,901 | B1 | 7/2005 | Theeuwes | 604/500 |
| 6,918,918 | B1 | 7/2005 | Schraga | 606/182 |
| 6,922,576 | B2 | 7/2005 | Raskas | 600/316 |
| 6,922,578 | B2 | 7/2005 | Eppstein | 600/347 |
| 6,923,764 | B2 | 8/2005 | Aceti | 600/309 |
| 6,923,894 | B2 | 8/2005 | Huang | 204/403.06 |
| 6,923,936 | B2 | 8/2005 | Swanson | 422/22 |
| 6,924,093 | B2 | 8/2005 | Haviland | 435/4 |
| 6,925,317 | B1 | 8/2005 | Samuels | 600/344 |
| 6,925,393 | B1 | 8/2005 | Kalatz | 702/27 |
| 6,929,631 | B1 | 8/2005 | Brugger | 604/502 |
| 6,929,649 | B2 | 8/2005 | Pugh | 606/182 |
| 6,929,650 | B2 | 8/2005 | Fukuzawa | 606/182 |
| 6,931,327 | B2 | 8/2005 | Goode | 702/22 |
| 6,931,328 | B2 | 8/2005 | Braig | 702/23 |
| 6,939,310 | B2 | 9/2005 | Matzinger | 600/573 |
| 6,939,312 | B2 | 9/2005 | Hodges | 600/583 |
| 6,939,450 | B2 | 9/2005 | Karinka | 204/409 |
| 6,939,685 | B2 | 9/2005 | Ouyang | 435/26 |
| 6,940,591 | B2 | 9/2005 | Sopp | 356/244 |
| 6,942,518 | B2 | 9/2005 | Liamos | 439/495 |
| 6,942,769 | B2 | 9/2005 | Cheng | 204/400 |
| 6,942,770 | B2 | 9/2005 | Cai | 204/403.04 |
| 6,944,486 | B2 | 9/2005 | Braig | 600/310 |
| 6,945,943 | B2 | 9/2005 | Pugh | 600/584 |
| 6,946,067 | B2 | 9/2005 | Hodges | 205/792 |
| 6,946,098 | B2 | 9/2005 | Miekka | 422/22 |
| 6,946,299 | B2 | 9/2005 | Neel | 436/95 |
| 6,949,111 | B2 | 9/2005 | Schraga | 606/182 |
| 6,949,221 | B2 | 9/2005 | Kiser | 422/56 |
| 6,951,631 | B1 | 10/2005 | Catt | 422/56 |
| 6,951,728 | B2 | 10/2005 | Qian | 435/14 |
| 6,952,603 | B2 | 10/2005 | Gerber | 600/310 |
| 6,952,604 | B2 | 10/2005 | DeNuzzio | 600/345 |
| 6,953,693 | B2 | 10/2005 | Neel | 436/149 |
| 6,954,662 | B2 | 10/2005 | Freger | 600/316 |
| 6,958,072 | B2 | 10/2005 | Schraga | 606/182 |
| 6,958,129 | B2 | 10/2005 | Galen | 422/57 |
| 6,958,809 | B2 | 10/2005 | Sterling | 356/39 |
| 6,959,211 | B2 | 10/2005 | Rule | 600/310 |
| 6,959,247 | B2 | 10/2005 | Neel | 702/19 |
| 6,960,287 | B2 | 11/2005 | Charlton | 205/775 |
| 6,960,289 | B2 | 11/2005 | Hodges | 205/778 |
| 6,960,323 | B2 | 11/2005 | Guo | 422/60 |
| 6,964,871 | B2 | 11/2005 | Bell | 436/95 |
| 6,965,791 | B1 | 11/2005 | Hitchcock | 600/345 |
| 6,966,880 | B2 | 11/2005 | Boecker | 600/583 |
| 6,966,977 | B2 | 11/2005 | Hasegawa | 204/403.07 |
| 6,967,105 | B2 | 11/2005 | Nomura | 436/169 |
| 6,968,375 | B1 | 11/2005 | Brown | 709/224 |
| 6,969,359 | B2 | 11/2005 | Duchon | 600/583 |
| 6,969,450 | B2 | 11/2005 | Taniike | 204/403.01 |
| 6,969,451 | B2 | 11/2005 | Shin | 204/412 |
| 6,973,706 | B2 | 12/2005 | Say | 29/595 |
| 6,975,893 | B2 | 12/2005 | Say | 600/347 |
| 6,977,032 | B2 | 12/2005 | Hasegawa | 204/403.05 |
| 6,977,722 | B2 | 12/2005 | Wohlstadter et al. | 356/246 |
| 6,979,544 | B2 | 12/2005 | Keen | 435/6 |
| 6,979,571 | B2 | 12/2005 | Modzelewski | 436/164 |
| 6,982,027 | B2 | 1/2006 | Yagi | 204/403.06 |
| 6,982,431 | B2 | 1/2006 | Modlin | 250/573 |
| 6,983,176 | B2 | 1/2006 | Gardner | 600/310 |
| 6,983,177 | B2 | 1/2006 | Rule | 600/310 |
| 6,984,307 | B2 | 1/2006 | Zweig | 205/777.5 |
| 6,986,777 | B2 | 1/2006 | Kim | 606/182 |
| 6,986,869 | B2 | 1/2006 | Tuohy | 422/56 |
| 6,988,996 | B2 | 1/2006 | Roe | 600/584 |
| 6,989,243 | B2 | 1/2006 | Yani | 435/14 |
| 6,989,891 | B2 | 1/2006 | Braig | 356/39 |
| 6,990,365 | B1 | 1/2006 | Parker | 600/328 |
| 6,990,366 | B2 | 1/2006 | Say | 600/345 |
| 6,990,367 | B2 | 1/2006 | Kiser | 600/345 |
| 6,990,849 | B2 | 1/2006 | Bohm | 73/53.01 |
| 6,991,918 | B2 | 1/2006 | Keith | 435/31 |
| 6,991,940 | B2 | 1/2006 | Carroll | 436/514 |
| 6,994,825 | B2 | 2/2006 | Haviland | 422/58 |
| 6,997,317 | B2 | 2/2006 | Catelli | 206/438 |
| 6,997,343 | B2 | 2/2006 | May | 221/232 |
| 6,997,344 | B2 | 2/2006 | Brown | 221/258 |
| 6,997,936 | B2 | 2/2006 | Marshall | 606/181 |
| 6,998,247 | B2 | 2/2006 | Monfre | 435/14 |
| 6,998,248 | B2 | 2/2006 | Yani | 435/14 |
| 6,999,810 | B2 | 2/2006 | Berner | 600/345 |
| 7,001,343 | B2 | 2/2006 | Erickson | 600/573 |
| 7,001,344 | B2 | 2/2006 | Freeman | 600/583 |
| 7,003,337 | B2 | 2/2006 | Harjunmaa | 600/316 |
| 7,003,340 | B2 | 2/2006 | Say | 600/345 |
| 7,003,341 | B2 | 2/2006 | Say | 600/345 |
| 7,004,928 | B2 | 2/2006 | Aceti | 604/191 |
| 7,005,048 | B1 | 2/2006 | Watanabe | 204/403.04 |

(56) References Cited

U.S. PATENT DOCUMENTS

| | | | | |
|---|---|---|---|---|
| 7,005,273 | B2 | 2/2006 | Heller | 435/25 |
| 7,005,459 | B2 | 2/2006 | Hekal | 523/102 |
| 7,005,857 | B2 | 2/2006 | Stiene | 324/449 |
| 7,006,857 | B2 | 2/2006 | Braig | 600/310 |
| 7,006,858 | B2 | 2/2006 | Silver | 600/345 |
| 7,008,384 | B2 | 3/2006 | Tapper | 600/573 |
| 7,010,432 | B2 | 3/2006 | Kermani | 702/19 |
| 7,011,630 | B2 | 3/2006 | Desai | 600/309 |
| 7,011,954 | B2 | 3/2006 | Ouyang | 435/7.9 |
| 7,014,615 | B2 | 3/2006 | Erickson | 600/573 |
| 7,015,262 | B2 | 3/2006 | Leong | 523/205 |
| 7,016,713 | B2 | 3/2006 | Gardner | 600/310 |
| 7,018,568 | B2 | 3/2006 | Tierney | 252/511 |
| 7,018,848 | B2 | 3/2006 | Douglas | 436/524 |
| 7,022,217 | B2 | 4/2006 | Hodges | 205/777.5 |
| 7,022,218 | B2 | 4/2006 | Taniike | 205/777.5 |
| 7,022,286 | B2 | 4/2006 | Lemke | 422/67 |
| 7,024,236 | B2 | 4/2006 | Ford | 600/345 |
| 7,024,248 | B2 | 4/2006 | Penner | 607/60 |
| 7,024,399 | B2 | 4/2006 | Sumner | 706/45 |
| 7,025,425 | B2 | 4/2006 | Kovatchev | 300/365 |
| 7,025,774 | B2 | 4/2006 | Freeman | 606/181 |
| 7,027,848 | B2 | 4/2006 | Robinson | 600/310 |
| 7,029,444 | B2 | 4/2006 | Shin | 600/365 |
| 7,033,322 | B2 | 4/2006 | Silver | 600/486 |
| 7,033,371 | B2 | 4/2006 | Alden | 606/181 |
| 7,039,560 | B2 | 5/2006 | Kawatahara | 702/187 |
| 7,041,057 | B1 | 5/2006 | Faupel | 600/365 |
| 7,041,063 | B2 | 5/2006 | Abreu | 600/549 |
| 7,041,068 | B2 | 5/2006 | Freeman | 600/583 |
| 7,041,210 | B2 | 5/2006 | Hodges | 205/792 |
| 7,041,254 | B2 | 5/2006 | Haviland | 422/58 |
| 7,041,468 | B2 | 5/2006 | Drucker | 435/14 |
| 7,043,287 | B1 | 5/2006 | Khalil | 600/310 |
| 7,043,821 | B2 | 5/2006 | Hodges | 29/594 |
| 7,044,911 | B2 | 5/2006 | Drinan | 600/300 |
| 7,045,046 | B2 | 5/2006 | Chambers | 204/400 |
| 7,045,054 | B1 | 5/2006 | Buck | 205/778 |
| 7,045,097 | B2 | 5/2006 | Kovacs | 422/82.08 |
| 7,045,310 | B2 | 5/2006 | Buck | 435/7.93 |
| 7,045,361 | B2 | 5/2006 | Heiss | 436/172 |
| 7,047,070 | B2 | 5/2006 | Wilkinson | 604/20 |
| 7,047,795 | B2 | 5/2006 | Sato | 73/64.56 |
| 7,049,087 | B2 | 5/2006 | Jenny | 435/13 |
| 7,049,130 | B2 | 5/2006 | Carroll | 435/287.2 |
| 7,050,843 | B2 | 5/2006 | Shartle | 600/345 |
| 7,051,495 | B2 | 5/2006 | Lang | 53/475 |
| 7,052,268 | B2 | 5/2006 | Powell | 425/542 |
| 7,052,591 | B2 | 5/2006 | Gao | 204/490 |
| 7,052,652 | B2 | 5/2006 | Zanzucchi | 422/82.05 |
| 7,052,864 | B2 | 5/2006 | Durkop | 435/25 |
| 7,054,682 | B2 | 5/2006 | Young | 604/20 |
| 7,054,759 | B2 | 5/2006 | Fukunaga | 702/23 |
| D522,656 | S | 6/2006 | Orr | D24/169 |
| D523,555 | S | 6/2006 | Loerwald | D24/146 |
| 7,056,425 | B2 | 6/2006 | Hasegawa | 204/403.04 |
| 7,056,495 | B2 | 6/2006 | Roser | 424/45 |
| 7,058,437 | B2 | 6/2006 | Buse | 600/347 |
| 7,059,352 | B2 | 6/2006 | Bohm | 137/828 |
| 7,060,059 | B2 | 6/2006 | Keith | 604/504 |
| 7,060,168 | B2 | 6/2006 | Taniike | 204/403.04 |
| 7,060,192 | B2 | 6/2006 | Yuzhakov | 216/11 |
| 7,061,593 | B2 | 6/2006 | Braig | 356/39 |
| 7,063,234 | B2 | 6/2006 | Giraud | 221/271 |
| 7,063,774 | B2 | 6/2006 | Bhullar | 204/403.02 |
| 7,063,775 | B2 | 6/2006 | Yamaoka | 204/403.06 |
| 7,063,776 | B2 | 6/2006 | Huang | 204/403.14 |
| 7,066,884 | B2 | 6/2006 | Custer | 600/309 |
| 7,066,885 | B2 | 6/2006 | Erickson | 600/309 |
| 7,070,564 | B2 | 7/2006 | Matzinger | 600/300 |
| 7,070,680 | B2 | 7/2006 | Bae | 204/403.04 |
| 7,073,246 | B2 | 7/2006 | Bhullar | 29/595 |
| 7,074,307 | B2 | 7/2006 | Simpson | 204/403.04 |
| 7,074,308 | B2 | 7/2006 | Mao | 204/403.14 |
| 7,077,328 | B2 | 7/2006 | Krishnaswamy | 235/472.01 |
| 7,077,828 | B2 | 7/2006 | Kuhr | 604/207 |
| 7,078,480 | B2 | 7/2006 | Nagel | 530/322 |
| 7,079,252 | B1 | 7/2006 | Debreezeny | 356/451 |
| 7,081,188 | B1 | 7/2006 | Cho | 204/403.04 |
| 7,083,712 | B2 | 8/2006 | Morita | 205/775 |
| 7,086,277 | B2 | 8/2006 | Tess | 73/53.01 |
| 7,087,149 | B1 | 8/2006 | Muguruma | 205/778 |
| 7,090,764 | B2 | 8/2006 | Iyengar | 205/775 |
| 7,096,053 | B2 | 8/2006 | Loeb | 600/317 |
| 7,096,124 | B2 | 8/2006 | Sterling | 702/23 |
| 7,097,631 | B2 | 8/2006 | Trautman | 604/46 |
| 7,098,038 | B2 | 8/2006 | Fukuoka | 436/164 |
| 7,103,578 | B2 | 9/2006 | Beck | 705/75 |
| 7,105,066 | B2 | 9/2006 | Jeong et al. | 606/182 |
| 7,107,253 | B1 | 9/2006 | Sumner | 706/45 |
| 7,108,680 | B2 | 9/2006 | Rohr | 604/151 |
| 7,108,778 | B2 | 9/2006 | Simpson | 205/778 |
| 7,109,271 | B2 | 9/2006 | Liu | 525/283 |
| 7,110,112 | B2 | 9/2006 | Uchida | 356/364 |
| 7,110,803 | B2 | 9/2006 | Shults | 600/347 |
| 7,112,265 | B1 | 9/2006 | McAleer | 204/403.09 |
| 7,112,451 | B2 | 9/2006 | Takahashi | 436/514 |
| 7,113,172 | B2 | 9/2006 | Hohl | 345/168 |
| 7,115,362 | B2 | 10/2006 | Douglas | 435/4 |
| 7,118,351 | B2 | 10/2006 | Effenhauser | 417/208 |
| 7,118,667 | B2 | 10/2006 | Lee | 205/777.5 |
| 7,118,668 | B1 | 10/2006 | Edelbrock | 205/777.5 |
| 7,118,916 | B2 | 10/2006 | Matzinger | 436/34 |
| 7,118,919 | B2 | 10/2006 | Yatscoff | 436/56 |
| 7,120,483 | B2 | 10/2006 | Russell | 600/345 |
| 7,122,102 | B2 | 10/2006 | Wogoman | 204/400 |
| 7,122,110 | B2 | 10/2006 | Deng | 205/777.5 |
| 7,122,111 | B2 | 10/2006 | Tokunaga | 205/792 |
| 7,125,481 | B2 | 10/2006 | Musho | 205/775 |
| 7,129,038 | B2 | 10/2006 | Gopalan | 435/4 |
| RE39,390 | E | 11/2006 | Hasegawa | 204/403.9 |
| D531,725 | S | 11/2006 | Loerwald | D24/146 |
| 7,131,342 | B2 | 11/2006 | Hodges | 73/864.72 |
| 7,131,984 | B2 | 11/2006 | Sato | 606/182 |
| 7,132,041 | B2 | 11/2006 | Deng | 205/777.5 |
| 7,133,710 | B2 | 11/2006 | Acosta | 600/316 |
| 7,134,550 | B2 | 11/2006 | Groth | 206/366 |
| 7,134,999 | B2 | 11/2006 | Brauker | 600/309 |
| 7,135,100 | B1 | 11/2006 | Lau | 204/403.14 |
| 7,137,957 | B2 | 11/2006 | Erickson | 600/573 |
| 7,138,041 | B2 | 11/2006 | Su | 204/403.04 |
| 7,138,089 | B2 | 11/2006 | Aitken | 422/82.01 |
| 7,141,034 | B2 | 11/2006 | Eppstein | 604/22 |
| 7,141,058 | B2 | 11/2006 | Briggs | 606/181 |
| 7,144,404 | B2 | 12/2006 | Whitson | 606/181 |
| 7,144,485 | B2 | 12/2006 | Hsu | 204/403.02 |
| 7,144,495 | B2 | 12/2006 | Teodorczyk | 205/792 |
| 7,144,496 | B2 | 12/2006 | Meserol | 205/792 |
| 7,144,709 | B2 | 12/2006 | Ouyang | 435/7.9 |
| 7,147,825 | B2 | 12/2006 | Matsuda | 422/58 |
| 7,150,755 | B2 | 12/2006 | Levaughn | 606/181 |
| 7,150,975 | B2 | 12/2006 | Tamada | 435/14 |
| 7,150,995 | B2 | 12/2006 | Xie | 436/67 |
| 7,153,696 | B2 | 12/2006 | Fukuoka | 436/164 |
| 7,155,371 | B2 | 12/2006 | Kawatahara | 702/187 |
| 7,156,117 | B2 | 1/2007 | Bohm | 137/14 |
| 7,156,810 | B2 | 1/2007 | Cho | 600/365 |
| 7,157,723 | B2 | 1/2007 | Colvin | 250/458.1 |
| 7,160,251 | B2 | 1/2007 | Neel | 600/365 |
| 7,160,313 | B2 | 1/2007 | Galloway | 606/167 |
| 7,160,678 | B1 | 1/2007 | Kayyem | 435/6 |
| 7,162,289 | B2 | 1/2007 | Shah | 600/345 |
| 7,163,616 | B2 | 1/2007 | Vreeke | 205/777.5 |
| 7,166,074 | B2 | 1/2007 | Reghabi | 600/365 |
| 7,166,208 | B2 | 1/2007 | Zweig | 205/777.5 |
| 7,167,734 | B2 | 1/2007 | Khalil | 600/310 |
| 7,167,735 | B2 | 1/2007 | Uchida | 600/310 |
| 7,167,818 | B2 | 1/2007 | Brown | 703/11 |
| 7,169,116 | B2 | 1/2007 | Day | 600/583 |
| 7,169,117 | B2 | 1/2007 | Allen | 600/584 |
| 7,169,289 | B2 | 1/2007 | Schulein | 205/777.5 |
| 7,169,600 | B2 | 1/2007 | Hoss | 435/287.1 |
| 7,172,728 | B2 | 2/2007 | Otake | 422/58 |
| 7,174,199 | B2 | 2/2007 | Berner et al. | 600/347 |

(56) References Cited

U.S. PATENT DOCUMENTS

| | | | |
|---|---|---|---|
| 7,175,641 B1 | 2/2007 | Schraga | 606/181 |
| 7,175,642 B2 | 2/2007 | Briggs | 606/181 |
| 7,179,233 B2 | 2/2007 | Chang | 600/584 |
| 7,182,910 B2 | 2/2007 | Allen | 422/50 |
| 7,183,068 B2 | 2/2007 | Burson | 435/14 |
| 7,183,102 B2 | 2/2007 | Monfre et al. | 200/51.09 |
| 7,188,034 B2 | 3/2007 | Staib | 702/22 |
| 7,189,576 B2 | 3/2007 | Fukuoka | 436/170 |
| 7,190,988 B2 | 3/2007 | Say | 600/345 |
| 7,192,405 B2 | 3/2007 | DeNuzzio | 600/583 |
| 7,192,450 B2 | 3/2007 | Brauker | 623/23.76 |
| 7,195,704 B2 | 3/2007 | Kermani | 205/777.5 |
| 7,198,606 B2 | 4/2007 | Boecker | 600/583 |
| 7,199,594 B2 | 4/2007 | Kermani | 324/663 |
| 7,202,854 B2 | 4/2007 | Hohl | 345/168 |
| 7,206,620 B2 | 4/2007 | Erickson | 600/310 |
| 7,206,623 B2 | 4/2007 | Blank | 600/344 |
| D542,681 S | 5/2007 | Young | D10/80 |
| 7,211,052 B2 | 5/2007 | Roe | 600/584 |
| 7,211,096 B2 | 5/2007 | Kuhr | 606/182 |
| 7,212,925 B2 | 5/2007 | Genshaw | 702/23 |
| 7,213,720 B2 | 5/2007 | Giraud | 220/839 |
| 7,215,982 B2 | 5/2007 | Oshima | 600/310 |
| 7,215,983 B2 | 5/2007 | Cho | 600/316 |
| 7,223,248 B2 | 5/2007 | Erickson | 600/584 |
| 7,225,008 B1 | 5/2007 | Ward | 600/345 |
| D543,878 S | 6/2007 | Castillo | D10/81 |
| D545,438 S | 6/2007 | Huang | D24/186 |
| 7,225,535 B2 | 6/2007 | Feldman | 29/831 |
| 7,226,414 B2 | 6/2007 | Ballerstadt | 600/365 |
| 7,226,461 B2 | 6/2007 | Boecker | 606/181 |
| 7,226,978 B2 | 6/2007 | Tapsak | 525/296 |
| 7,227,156 B2 | 6/2007 | Colvin | 250/458.1 |
| 7,228,159 B2 | 6/2007 | Petersson | 600/316 |
| 7,228,162 B2 | 6/2007 | Ward | 600/345 |
| 7,228,163 B2 | 6/2007 | Ackerman | 600/347 |
| 7,229,458 B2 | 6/2007 | Boecker | 606/181 |
| 7,232,451 B2 | 6/2007 | Boecker | 606/181 |
| 7,232,510 B2 | 6/2007 | Miyazaki | 204/403.1 |
| 7,233,816 B2 | 6/2007 | Blank | 600/310 |
| 7,235,056 B2 | 6/2007 | Duchon | 600/583 |
| 7,235,170 B2 | 6/2007 | Watanabe | 205/777.5 |
| 7,235,378 B2 | 6/2007 | Yonehara | 435/14 |
| 7,236,812 B1 | 6/2007 | Ballerstadt | 600/316 |
| 7,236,814 B2 | 6/2007 | Shioi | 600/344 |
| D545,705 S | 7/2007 | Voege | D10/81 |
| D546,216 S | 7/2007 | Bolognesi | D10/81 |
| D546,218 S | 7/2007 | Grasso | D10/81 |
| 2,747,138 A1 | 7/2007 | Reghabi | 600/365 |
| 7,238,192 B2 | 7/2007 | List | 606/181 |
| 7,238,534 B1 | 7/2007 | Zimmer | 436/169 |
| 7,241,265 B2 | 7/2007 | Cummings | 600/300 |
| 7,244,264 B2 | 7/2007 | Roe | 606/181 |
| 7,244,265 B2 | 7/2007 | Freeman | 606/181 |
| 7,244,266 B2 | 7/2007 | Garthe | 606/181 |
| 7,247,144 B2 | 7/2007 | Douglas | 600/583 |
| 7,250,037 B2 | 7/2007 | Shermer | 604/134 |
| 7,250,056 B2 | 7/2007 | Hamamoto | 606/181 |
| 7,250,095 B2 | 7/2007 | Black | 204/403.14 |
| 7,250,105 B1 | 7/2007 | Davies | 205/777.5 |
| 7,251,513 B2 | 7/2007 | Kondoh et al. | 600/310 |
| 7,251,514 B2 | 7/2007 | Cho | 600/316 |
| 7,251,515 B2 | 7/2007 | Cho | 600/316 |
| 7,251,516 B2 | 7/2007 | Walker | 600/316 |
| 7,251,517 B2 | 7/2007 | Cho | 600/316 |
| 7,251,518 B2 | 7/2007 | Herrmann | 600/322 |
| 7,252,804 B2 | 8/2007 | Miyashita | 422/104 |
| 7,254,426 B2 | 8/2007 | Cho | 600/316 |
| 7,254,427 B2 | 8/2007 | Cho | 600/316 |
| 7,254,428 B2 | 8/2007 | Cho | 600/316 |
| 7,254,429 B2 | 8/2007 | Schurman | 600/316 |
| 7,254,430 B2 | 8/2007 | Cho | 600/316 |
| 7,254,432 B2 | 8/2007 | Fine | 600/335 |
| 7,258,673 B2 | 8/2007 | Racchini | 600/583 |
| 7,258,693 B2 | 8/2007 | Freeman | 606/181 |
| 7,262,061 B2 | 8/2007 | Petrich | 436/169 |
| 7,264,139 B2 | 9/2007 | Brickwood | 221/270 |
| 7,264,627 B2 | 9/2007 | Perez | 606/181 |
| 7,266,400 B2 | 9/2007 | Fine | 600/316 |
| 7,267,665 B2 | 9/2007 | Steil | 604/131 |
| 7,267,750 B2 | 9/2007 | Watanabe | 204/403.04 |
| 7,270,247 B2 | 9/2007 | Charlton | 221/59 |
| 7,271,912 B2 | 9/2007 | Sterling | 356/436 |
| 7,273,484 B2 | 9/2007 | Thoes | 606/181 |
| 7,276,027 B2 | 10/2007 | Haar | 600/309 |
| 7,276,029 B2 | 10/2007 | Goode | 600/365 |
| 7,276,146 B2 | 10/2007 | Wilsey | 205/792 |
| 7,276,147 B2 | 10/2007 | Wilsey | 205/792 |
| 7,276,380 B2 | 10/2007 | Fukuyama | 436/164 |
| 7,277,740 B2 | 10/2007 | Rohleder | 600/316 |
| 7,278,983 B2 | 10/2007 | Ireland | 604/66 |
| 7,279,130 B2 | 10/2007 | Brown | 422/64 |
| 7,282,058 B2 | 10/2007 | Levin | 606/181 |
| 7,287,318 B2 | 10/2007 | Bhullar | 29/825 |
| 7,288,073 B2 | 10/2007 | Effenhauser | 600/584 |
| 7,288,102 B2 | 10/2007 | Griffin | 606/182 |
| 7,288,174 B2 | 10/2007 | Cui | 204/403.14 |
| 7,289,836 B2 | 10/2007 | Colvin | 600/316 |
| 7,291,117 B2 | 11/2007 | Boecker | 600/583 |
| 7,291,159 B2 | 11/2007 | Schmelzeisen | 606/181 |
| 7,291,256 B2 | 11/2007 | Teodorczyk | 205/777.5 |
| 7,291,497 B2 | 11/2007 | Holmes | 435/287.2 |
| 7,294,246 B2 | 11/2007 | Gundel | 204/403.14 |
| 7,295,867 B2 | 11/2007 | Berner | 600/345 |
| 7,297,122 B2 | 11/2007 | Boecker | 600/583 |
| 7,297,151 B2 | 11/2007 | Boecker | 606/181 |
| 7,297,152 B2 | 11/2007 | Fukuzawa | 606/181 |
| 7,297,241 B2 | 11/2007 | Kontschieder | 204/403.01 |
| 7,297,248 B2 | 11/2007 | Bae | 205/777.5 |
| 7,297,627 B2 | 11/2007 | Shah et al. | 438/622 |
| 7,299,079 B2 | 11/2007 | Rebec et al. | 600/316 |
| 7,299,080 B2 | 11/2007 | Acosta et al. | 600/316 |
| 7,299,081 B2 | 11/2007 | Mace et al. | 600/345 |
| 7,299,082 B2 | 11/2007 | Feldman | 600/347 |
| 7,300,402 B2 | 11/2007 | Iliff | 600/300 |
| 7,301,629 B2 | 11/2007 | Bambot | 356/337 |
| 7,303,573 B2 | 12/2007 | D'Agostino | 606/181 |
| 7,303,726 B2 | 12/2007 | McAllister | 422/68.1 |
| 7,303,922 B2 | 12/2007 | Jeng | 436/164 |
| 7,305,896 B2 | 12/2007 | Howell | 73/864.02 |
| 7,306,560 B2 | 12/2007 | Iliff | 600/300 |
| 7,308,164 B1 | 12/2007 | Banks | 385/12 |
| 7,308,292 B2 | 12/2007 | Colvin | 600/310 |
| 7,310,542 B2 | 12/2007 | Jeon | 600/344 |
| 7,310,543 B2 | 12/2007 | Smart | 600/345 |
| 7,310,544 B2 | 12/2007 | Brister | 600/345 |
| 7,311,718 B2 | 12/2007 | Schraga | 606/181 |
| 7,311,812 B2 | 12/2007 | Forrow | 204/403.06 |
| 7,312,042 B1 | 12/2007 | Petyt | 435/7.1 |
| 7,313,425 B2 | 12/2007 | Finarov | 600/310 |
| 7,314,453 B2 | 1/2008 | Kuo | 600/584 |
| 7,315,752 B2 | 1/2008 | Kraemer | 600/316 |
| 7,316,700 B2 | 1/2008 | Alden | 606/181 |
| 7,316,766 B2 | 1/2008 | Chen | 204/403.01 |
| 7,316,929 B2 | 1/2008 | Purcell | 436/8 |
| 7,317,938 B2 | 1/2008 | Lorenz | 600/316 |
| 7,317,939 B2 | 1/2008 | Fine | 600/322 |
| 7,320,412 B2 | 1/2008 | Fitzgerald | 340/870.07 |
| 7,322,942 B2 | 1/2008 | Roe | 600/583 |
| 7,322,996 B2 | 1/2008 | Taylor | 606/181 |
| 7,322,997 B2 | 1/2008 | Shi | 606/181 |
| 7,322,998 B2 | 1/2008 | Kuhr | 606/182 |
| 7,323,098 B2 | 1/2008 | Miyashita | 205/777.5 |
| 7,323,141 B2 | 1/2008 | Kirchhevel | 422/68.1 |
| 7,323,315 B2 | 1/2008 | Marfurt | 435/7.25 |
| 7,328,052 B2 | 2/2008 | Samsoondar | 600/310 |
| 7,331,931 B2 | 2/2008 | Freeman | 600/583 |
| 7,335,292 B2 | 2/2008 | Hodges | 205/775 |
| 7,335,294 B2 | 2/2008 | Heller | 205/792 |
| 7,337,918 B2 | 3/2008 | Fowler | 221/65 |
| 7,338,639 B2 | 3/2008 | Burke | 422/82.1 |
| 7,343,188 B2 | 3/2008 | Sohrab | 600/345 |
| 7,344,499 B1 | 3/2008 | Prausnitz | 600/309 |
| 7,344,500 B2 | 3/2008 | Talbot | 600/365 |

(56) References Cited

U.S. PATENT DOCUMENTS

| | | | |
|---|---|---|---|
| 7,344,507 B2 | 3/2008 | Briggs | 600/583 |
| 7,344,626 B2 | 3/2008 | Harding | 204/403.01 |
| 7,347,925 B2 | 3/2008 | Hsieh | 205/777.5 |
| 7,347,926 B2 | 3/2008 | Morita | 205/792 |
| 7,347,973 B2 | 3/2008 | Douglas | 422/61 |
| RE40,198 E | 4/2008 | Buck | 205/777.5 |
| 7,351,213 B2 | 4/2008 | Wong | 600/584 |
| 7,351,323 B2 | 4/2008 | Iketaki | 205/777.5 |
| 7,351,375 B2 | 4/2008 | Noda | 422/82.01 |
| 7,351,770 B2 | 4/2008 | Liu | 525/283 |
| 7,357,808 B2 | 4/2008 | Kennedy | 606/181 |
| 7,357,851 B2 | 4/2008 | Reid | 204/403.04 |
| 7,361,182 B2 | 4/2008 | Fukuda | 606/181 |
| 7,361,307 B2 | 4/2008 | Shartle | 422/82.01 |
| 7,371,247 B2 | 5/2008 | Boecker | 606/181 |
| 7,372,277 B2 | 5/2008 | Diamond | 324/444 |
| 7,374,544 B2 | 5/2008 | Freeman | 600/583 |
| 7,374,546 B2 | 5/2008 | Roe | 600/583 |
| 7,378,007 B2 | 5/2008 | Moerman | 204/403.03 |
| 7,378,270 B2 | 5/2008 | Azarnia et al. | 435/287.2 |
| 7,402,616 B2 | 7/2008 | Rodgers | 523/160 |
| 7,404,815 B2 | 7/2008 | Kollias | 604/501 |
| 7,410,468 B2 | 8/2008 | Freeman | 600/583 |
| 7,429,630 B2 | 9/2008 | Liu | 525/283 |
| 7,431,814 B2 | 10/2008 | Hodges | 204/403.02 |
| 7,431,820 B2 | 10/2008 | Hodges | 205/777.5 |
| 7,438,694 B2 | 10/2008 | Boozer | 600/583 |
| D579,652 S | 11/2008 | Lim | D3/201 |
| D579,653 S | 11/2008 | Lim | D3/201 |
| 7,462,265 B2 | 12/2008 | Leach | 204/403.14 |
| 7,465,380 B2 | 12/2008 | Rodgers | 204/403.14 |
| 7,468,125 B2 | 12/2008 | Kraft | 205/792 |
| D585,314 S | 1/2009 | Schvetz | D10/78 |
| 7,473,264 B2 | 1/2009 | Allen | 606/181 |
| 7,474,390 B2 | 1/2009 | Robinson | 356/42 |
| 7,474,391 B2 | 1/2009 | Baskeyfield | 356/42 |
| 7,481,776 B2 | 1/2009 | Boecker | 600/583 |
| 7,481,818 B2 | 1/2009 | Allen | 606/181 |
| D586,465 S | 2/2009 | Faulkner | D24/146 |
| D586,466 S | 2/2009 | Smith | D24/186 |
| D586,678 S | 2/2009 | Schvetz | D10/81 |
| D586,916 S | 2/2009 | Faulkner | D24/146 |
| 7,485,128 B2 | 2/2009 | Boecker | 606/181 |
| 7,491,178 B2 | 2/2009 | Boecker | 600/583 |
| 7,498,132 B2 | 3/2009 | Yu | 435/6 |
| 7,501,052 B2 | 3/2009 | Iyengar | 205/777.5 |
| 7,501,093 B2 | 3/2009 | Demelo | 422/58 |
| 7,521,019 B2 | 4/2009 | Polak | 422/82.06 |
| 7,524,293 B2 | 4/2009 | Freeman | 600/583 |
| 7,537,571 B2 | 5/2009 | Freeman | 600/583 |
| 7,547,287 B2 | 6/2009 | Boecker | 600/583 |
| 7,548,772 B2 | 6/2009 | Shartle | 600/345 |
| 7,553,511 B2 | 6/2009 | Hleong | 427/2.28 |
| 7,563,232 B2 | 7/2009 | Freeman | 600/583 |
| D598,126 S | 8/2009 | Alvarez-Icaza | D24/225 |
| 7,572,356 B2 | 8/2009 | Rodgers | 204/403.05 |
| 7,575,558 B2 | 8/2009 | Boecker | 600/573 |
| D600,349 S | 9/2009 | Bell | D24/169 |
| D600,812 S | 9/2009 | Lei | D24/169 |
| D600,813 S | 9/2009 | Bell | D24/169 |
| D601,255 S | 9/2009 | Schvetz | D24/169 |
| D601,258 S | 9/2009 | Bell | D24/169 |
| 7,582,063 B2 | 9/2009 | Wurster | 600/584 |
| 7,582,099 B2 | 9/2009 | Freeman | 606/181 |
| 7,586,590 B2 | 9/2009 | Baskeyfield | 356/42 |
| 7,588,670 B2 | 9/2009 | Rodgers | 204/403.14 |
| 7,589,828 B2 | 9/2009 | Robinson | 356/42 |
| 7,592,151 B2 | 9/2009 | Liu | 435/14 |
| 7,593,097 B2 | 9/2009 | Robinson | 356/42 |
| 7,604,592 B2 | 10/2009 | Freeman | 600/309 |
| 7,604,722 B2 | 10/2009 | Hodges | 204/403.02 |
| 7,608,175 B2 | 10/2009 | Hodges | 204/403.02 |
| 7,618,522 B2 | 11/2009 | Davies | 204/403.14 |
| 7,648,468 B2 | 1/2010 | Boecker | 600/583 |
| 7,648,469 B2 | 1/2010 | Boecker | 600/583 |
| 7,653,492 B2 | 1/2010 | Davies | 702/22 |
| 7,654,127 B2 | 2/2010 | Krulevitch | 73/1.16 |
| 7,655,119 B2 | 2/2010 | Davies | 204/403.14 |
| 7,665,303 B2 | 2/2010 | Bohm | 60/643 |
| 7,666,287 B2 | 2/2010 | Zhao | 204/600 |
| D611,151 S | 3/2010 | Lei | D24/169 |
| D611,372 S | 3/2010 | Salter | D10/81 |
| D611,489 S | 3/2010 | Bell | D14/486 |
| D611,853 S | 3/2010 | Salter | D10/81 |
| D612,274 S | 3/2010 | Heidemann | D10/78 |
| D612,275 S | 3/2010 | Salter | D10/81 |
| D612,279 S | 3/2010 | Heidemann | D10/103 |
| 7,674,232 B2 | 3/2010 | Boecker | 600/583 |
| 7,682,318 B2 | 3/2010 | Alden | 600/583 |
| 7,713,214 B2 | 5/2010 | Freeman et al. | 600/583 |
| 7,833,172 B2 | 11/2010 | Hein et al. | 600/583 |
| 7,879,058 B2 | 2/2011 | Ikeda | 606/182 |
| 7,901,365 B2 | 3/2011 | Freeman et al. | 600/583 |
| 8,079,960 B2 | 12/2011 | Briggs et al. | 600/583 |
| 8,162,968 B2 | 4/2012 | Boozer et al. | 606/182 |
| 8,206,319 B2 | 6/2012 | Freeman et al. | 600/583 |
| 8,231,548 B2 | 7/2012 | Hoenes | 600/583 |
| 8,251,922 B2 | 8/2012 | List et al. | 600/584 |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0018353 A1 | 8/2001 | Ishigaki | 455/566 |
| 2001/0023349 A1 | 9/2001 | VanTassel et al. | 606/53 |
| 2001/0027328 A1 | 10/2001 | Lum | 606/186 |
| 2001/0031931 A1 | 10/2001 | Cunningham | 600/573 |
| 2001/0037355 A1 | 11/2001 | Britt | 709/201 |
| 2001/0042004 A1 | 11/2001 | Taub | 705/11 |
| 2001/0045355 A1 | 11/2001 | Gephart | 204/400 |
| 2001/0054319 A1 | 12/2001 | Heller | 73/849 |
| 2002/0002326 A1 | 1/2002 | Causey | 600/300 |
| 2002/0002344 A1 | 1/2002 | Douglas | 600/583 |
| 2002/0004196 A1 | 1/2002 | Whitson | 600/573 |
| 2002/0016568 A1 | 2/2002 | Lebel | 604/131 |
| 2002/0016606 A1 | 2/2002 | Moerman | 606/181 |
| 2002/0016923 A1 | 2/2002 | Knaus | 713/200 |
| 2002/0019606 A1 | 2/2002 | Lebel | 604/66 |
| 2002/0019747 A1 | 2/2002 | Ware | 705/2 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040208 A1 | 4/2002 | Flaherty | 604/288.01 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum | 604/117 |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0058902 A1 | 5/2002 | Kollias et al. | 604/20 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0082543 A1 | 6/2002 | Park | 604/21 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0099308 A1 | 7/2002 | Bojan | 600/573 |
| 2002/0103499 A1 | 8/2002 | Perez | 606/182 |
| 2002/0120216 A1 | 8/2002 | Fritz | 600/583 |
| 2002/0120261 A1 | 8/2002 | Morris | 606/41 |
| 2002/0123335 A1 | 9/2002 | Luna | 455/419 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0141032 A1 | 10/2002 | Guarr et al. | 359/265 |
| 2002/0148739 A2 | 10/2002 | Liamos | 205/787 |
| 2002/0156355 A1 | 10/2002 | Gough | 600/345 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |

(56) References Cited

U.S. PATENT DOCUMENTS

| | | | |
|---|---|---|---|
| 2002/0169393 A1 | 11/2002 | Cunningham | 600/573 |
| 2002/0169394 A1 | 11/2002 | Eppstein | 600/573 |
| 2002/0176984 A1 | 11/2002 | Smart | 428/336 |
| 2002/0177761 A1 | 11/2002 | Orloff | 600/309 |
| 2002/0177763 A1 | 11/2002 | Burns | 600/345 |
| 2002/0188224 A1 | 12/2002 | Roe | 600/584 |
| 2003/0014010 A1 | 1/2003 | Carpenter | 604/117 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0032077 A1 | 2/2003 | Itoh | 435/14 |
| 2003/0038047 A1 | 2/2003 | Sleva | 206/370 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0057391 A1 | 3/2003 | Krulevitch | 251/11 |
| 2003/0060730 A1 | 3/2003 | Perez | 600/576 |
| 2003/0069509 A1 | 4/2003 | Matzinger et al. | 600/504 |
| 2003/0069753 A1 | 4/2003 | Brown | 705/2 |
| 2003/0072647 A1 | 4/2003 | Lum | 415/1 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0109860 A1 | 6/2003 | Black | 606/10 |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0120297 A1 | 6/2003 | Beyerlein | 606/185 |
| 2003/0135333 A1 | 7/2003 | Aceti | 702/31 |
| 2003/0136189 A1 | 7/2003 | Lauman | 73/304 C |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson | 600/573 |
| 2003/0150745 A1 | 8/2003 | Teodorczyk et al. | 205/775 |
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191376 A1 | 10/2003 | Samuels | 600/309 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0210811 A1 | 11/2003 | Dubowsky | 382/128 |
| 2003/0211619 A1* | 11/2003 | Olson et al. | 436/44 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | McAllister | 600/584 |
| 2003/0212347 A1 | 11/2003 | Sohrab | 600/584 |
| 2003/0212379 A1 | 11/2003 | Bylund | 604/504 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown | 600/300 |
| 2004/0026243 A1 | 2/2004 | Davies | 204/403.14 |
| 2004/0026244 A1 | 2/2004 | Hodges | 204/409 |
| 2004/0030353 A1 | 2/2004 | Schmelzeisen | 606/201 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0054267 A1 | 3/2004 | Feldman | 600/316 |
| 2004/0055898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0068283 A1 | 4/2004 | Fukuzawa et al. | 606/181 |
| 2004/0069657 A1 | 4/2004 | Hodges | 205/787 |
| 2004/0087990 A1 | 5/2004 | Boecker | 606/181 |
| 2004/0092842 A1 | 5/2004 | Boecker | 600/575 |
| 2004/0092994 A1 | 5/2004 | Briggs | 606/181 |
| 2004/0092995 A1 | 5/2004 | Boecker | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison | 606/181 |
| 2004/0102803 A1 | 5/2004 | Boecker | 606/183 |
| 2004/0106855 A1 | 6/2004 | Brown | 600/301 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0107116 A1 | 6/2004 | Brown | 705/2 |
| 2004/0115754 A1 | 6/2004 | Chang | 435/14 |
| 2004/0115831 A1 | 6/2004 | Meathrel | 436/514 |

(56) References Cited

U.S. PATENT DOCUMENTS

| | | | |
|---|---|---|---|
| 2004/0116780 A1 | 6/2004 | Brown | 600/300 |
| 2004/0116829 A1 | 6/2004 | Raney | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0137640 A1 | 7/2004 | Hirao | 436/514 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Keheiri | 606/182 |
| 2004/0167383 A1 | 8/2004 | Kim | 600/365 |
| 2004/0171057 A1 | 9/2004 | Yang | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | Van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koike | 606/181 |
| 2004/0193201 A1 | 9/2004 | Kim | 606/181 |
| 2004/0193377 A1 | 9/2004 | Brown | 702/19 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0199409 A1 | 10/2004 | Brown | 705/3 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.1 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219500 A1 | 11/2004 | Brown | 434/307 R |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220564 A1 | 11/2004 | Ho | 606/47 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231983 A1 | 11/2004 | Shen | 204/403.01 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Shraga | 606/181 |
| 2004/0238357 A1 | 12/2004 | Bhullar | 204/400 |
| 2004/0238358 A1 | 12/2004 | Forrow et al. | 204/403 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249254 A1 | 12/2004 | Racchini | 600/347 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | LeVaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode, Jr. | 600/365 |
| 2005/0027211 A1 | 2/2005 | Kuhr | 600/583 |
| 2005/0027562 A1 | 2/2005 | Brown | 705/2 |
| 2005/0033340 A1 | 2/2005 | Lipoma | 606/181 |

(56) References Cited

U.S. PATENT DOCUMENTS

| | | | |
|---|---|---|---|
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Nakahara et al. | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Shraga | 606/182 |
| 2005/0038465 A1 | 2/2005 | Shraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049472 A1 | 3/2005 | Manda | 600/345 |
| 2005/0049473 A1 | 3/2005 | Desai | 600/347 |
| 2005/0050859 A1 | 3/2005 | Coppeta | 53/471 |
| 2005/0054082 A1 | 3/2005 | Pachl | 435/287.2 |
| 2005/0054908 A1 | 3/2005 | Blank | 600/316 |
| 2005/0059872 A1 | 3/2005 | Shartle | 600/347 |
| 2005/0059895 A1 | 3/2005 | Brown | 600/481 |
| 2005/0060194 A1 | 3/2005 | Brown | 705/2 |
| 2005/0061668 A1 | 3/2005 | Brenneman | 204/403.01 |
| 2005/0064528 A1 | 3/2005 | Kwon | 435/14 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Gundel | 204/403.2 |
| 2005/0098433 A1 | 5/2005 | Gundel | 204/403.2 |
| 2005/0098434 A1 | 5/2005 | Gundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112712 A1 | 5/2005 | Ouyang | 435/14 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowicz | 705/1 |
| 2005/0114444 A1 | 5/2005 | Brown | 709/203 |
| 2005/0118056 A1 | 6/2005 | Swanson | 423/23 |
| 2005/0118062 A1 | 6/2005 | Otake | 422/68.1 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Prausnitz et al. | 604/173 |
| 2005/0137536 A1 | 6/2005 | Gonnelli | 604/264 |
| 2005/0140659 A1 | 6/2005 | Hohl | 345/169 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0149090 A1 | 7/2005 | Morita et al. | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0163176 A1 | 7/2005 | You et al. | 372/36 |
| 2005/0164299 A1 | 7/2005 | Stewart | 435/7.1 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169810 A1 | 8/2005 | Hagen | 422/102 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0176153 A1 | 8/2005 | O'hara | 436/70 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Saito | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205136 A1 | 9/2005 | Freeman | 137/554 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |

(56) References Cited

U.S. PATENT DOCUMENTS

| | | | |
|---|---|---|---|
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245846 A1 | 11/2005 | Casey | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030050 A1 | 2/2006 | Milne | 436/67 |
| 2006/0030761 A1 | 2/2006 | Raskas | 600/316 |
| 2006/0030788 A1 | 2/2006 | Wong | 600/583 |
| 2006/0034728 A1 | 2/2006 | Kloepfer | 422/68.1 |
| 2006/0037859 A1 | 2/2006 | Hodges | 204/400 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094985 A1 | 5/2006 | Aceti | 600/575 |
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olson | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0160100 A1 | 7/2006 | Gao | 435/6 |
| 2006/0161078 A1 | 7/2006 | Schraga | 600/583 |
| 2006/0161194 A1 | 7/2006 | Freeman | 606/185 |
| 2006/0163061 A1 | 7/2006 | Hodges | 204/401 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |

(56) References Cited

U.S. PATENT DOCUMENTS

| | | | |
|---|---|---|---|
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184065 A1 | 8/2006 | Deshmukh | 600/583 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0201804 A1 | 9/2006 | Chambers | 204/400 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222566 A1 | 10/2006 | Brauker et al. | 422/68.1 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | LeVaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0229652 A1 | 10/2006 | Lio et al. | 606/182 |
| 2006/0231396 A1 | 10/2006 | Yamaoka | 204/403.14 |
| 2006/0231418 A1 | 10/2006 | Harding | 205/775 |
| 2006/0231421 A1 | 10/2006 | Diamond | 205/777.5 |
| 2006/0231423 A1 | 10/2006 | Harding | 205/792 |
| 2006/0231425 A1 | 10/2006 | Harding | 205/792 |
| 2006/0231442 A1 | 10/2006 | Windus-Smith | 206/438 |
| 2006/0232278 A1 | 10/2006 | Diamond | 324/444 |
| 2006/0232528 A1 | 10/2006 | Harding | 345/87 |
| 2006/0233666 A1 | 10/2006 | Vu | 422/68.1 |
| 2006/0234263 A1 | 10/2006 | Light | 435/6 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247154 A1 | 11/2006 | Palmieri | 514/8 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | LeVaughn | 606/181 |
| 2006/0254932 A1 | 11/2006 | Hodges | 205/775 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0266644 A1 | 11/2006 | Pugh | 204/400 |
| 2006/0266765 A1 | 11/2006 | Pugh | 222/1 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0279431 A1 | 12/2006 | Bakarania et al. | 340/870.02 |
| 2006/0281187 A1 | 12/2006 | Emery | 436/169 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |
| 2007/0016103 A1 | 1/2007 | Calasso | 600/583 |
| 2007/0016104 A1 | 1/2007 | Jansen | 600/583 |
| 2007/0016239 A1 | 1/2007 | Sato | 606/181 |
| 2007/0017805 A1 | 1/2007 | Hodges | 204/400 |
| 2007/0027370 A1 | 2/2007 | Brauker | 600/309 |
| 2007/0027427 A1 | 2/2007 | Trautman | 604/46 |
| 2007/0032812 A1 | 2/2007 | Loerwald | 606/181 |
| 2007/0032813 A1 | 2/2007 | Flynn | 606/181 |
| 2007/0038149 A1 | 2/2007 | Calasso | 600/583 |
| 2007/0038235 A1 | 2/2007 | Freeman | 606/181 |
| 2007/0043305 A1 | 2/2007 | Boecker | 600/583 |
| 2007/0043386 A1 | 2/2007 | Freeman | 606/181 |
| 2007/0049901 A1 | 3/2007 | Wu | 604/506 |
| 2007/0049959 A1 | 3/2007 | Feaster | 606/181 |
| 2007/0055174 A1 | 3/2007 | Freeman | 600/583 |
| 2007/0055297 A1 | 3/2007 | Fukuzawa | 606/181 |
| 2007/0055298 A1 | 3/2007 | Uehata | 606/181 |
| 2007/0060842 A1 | 3/2007 | Alvarez-Icaza | 600/583 |
| 2007/0060843 A1 | 3/2007 | Alvarez-Icaza | 600/583 |
| 2007/0060844 A1 | 3/2007 | Alvarez-Icaza | 600/583 |
| 2007/0060845 A1 | 3/2007 | Perez | 600/583 |
| 2007/0061393 A1 | 3/2007 | Moore | 205/777.5 |
| 2007/0062250 A1 | 3/2007 | Krulevitch | 73/1.16 |
| 2007/0062251 A1 | 3/2007 | Anex | 73/1.36 |
| 2007/0062315 A1 | 3/2007 | Hodges | 73/864.72 |
| 2007/0064516 A1 | 3/2007 | Briggs | 365/230.05 |
| 2007/0066939 A1 | 3/2007 | Krulevitch | 604/152 |
| 2007/0066940 A1 | 3/2007 | Karunaratne | 604/152 |
| 2007/0068807 A1 | 3/2007 | Feldman | 204/403.01 |
| 2007/0073188 A1 | 3/2007 | Freeman | 600/583 |
| 2007/0073189 A1 | 3/2007 | Freeman | 600/583 |
| 2007/0074977 A1 | 4/2007 | Guo | 205/792 |
| 2007/0078358 A1 | 4/2007 | Escutia | 600/573 |
| 2007/0078360 A1 | 4/2007 | Matsumoto | 600/583 |
| 2007/0078474 A1 | 4/2007 | Kim | 606/181 |
| 2007/0080093 A1 | 4/2007 | Boozer | 206/569 |
| 2007/0083130 A1 | 4/2007 | Thomson | |
| 2007/0083131 A1 | 4/2007 | Escutia | 600/583 |
| 2007/0083222 A1 | 4/2007 | Schraga | 606/181 |
| 2007/0083335 A1 | 4/2007 | Moerman | 702/19 |
| 2007/0084749 A1 | 4/2007 | Demelo | 206/569 |
| 2007/0088377 A1 | 4/2007 | LeVaughn | 606/181 |
| 2007/0092923 A1 | 4/2007 | Chang | 435/14 |
| 2007/0093728 A1 | 4/2007 | Douglas | 600/583 |
| 2007/0093752 A1 | 4/2007 | Zhao | 604/131 |
| 2007/0093753 A1 | 4/2007 | Krulevitch | 604/131 |
| 2007/0093863 A1 | 4/2007 | Pugh | 606/181 |
| 2007/0093864 A1 | 4/2007 | Pugh | 606/181 |
| 2007/0095178 A1 | 5/2007 | Schraga | 83/13 |
| 2007/0100255 A1 | 5/2007 | Boecker | 600/583 |
| 2007/0100256 A1 | 5/2007 | Sansom | 600/583 |
| 2007/0100364 A1 | 5/2007 | Sansom | 606/181 |
| 2007/0102312 A1 | 5/2007 | Cha | 206/363 |
| 2007/0106178 A1 | 5/2007 | Roe | 600/583 |
| 2007/0108048 A1 | 5/2007 | Wang | 204/403.01 |
| 2007/0112281 A1 | 5/2007 | Olson | 600/583 |
| 2007/0112367 A1 | 5/2007 | Olson | 606/181 |
| 2007/0118051 A1 | 5/2007 | Korner et al. | 600/583 |

(56) References Cited

U.S. PATENT DOCUMENTS

| | | | |
|---|---|---|---|
| 2007/0119710 A1 | 5/2007 | Goldberger | 204/403.01 |
| 2007/0123801 A1 | 5/2007 | Goldberger | 600/583 |
| 2007/0123802 A1 | 5/2007 | Freeman | 600/583 |
| 2007/0123803 A1 | 5/2007 | Fujiwara et al. | 600/583 |
| 2007/0129618 A1 | 6/2007 | Goldberger | 600/345 |
| 2007/0129650 A1 | 6/2007 | Freeman | 600/583 |
| 2007/0131565 A1 | 6/2007 | Fujiwara | 205/777.5 |
| 2007/0135828 A1 | 6/2007 | Rutynowski | 606/181 |
| 2007/0142747 A1 | 6/2007 | Boecker | 600/583 |
| 2007/0142748 A1 | 6/2007 | Freeman | 600/583 |
| 2007/0142776 A9 | 6/2007 | Kovelman | 604/136 |
| 2007/0142854 A1 | 6/2007 | Schraga | 606/181 |
| 2007/0144235 A1 | 6/2007 | Werner | 73/1.82 |
| 2007/0149875 A1 | 6/2007 | Ouyang | 600/347 |
| 2007/0149897 A1 | 6/2007 | Ghesquiere | 600/583 |
| 2007/0161960 A1 | 7/2007 | Chen | |
| 2007/0162064 A1 | 7/2007 | Starnes | 606/181 |
| 2007/0162065 A1 | 7/2007 | Li | 606/182 |
| 2007/0167869 A1 | 7/2007 | Roe | 600/583 |
| 2007/0167870 A1 | 7/2007 | Freeman | 600/583 |
| 2007/0167871 A1 | 7/2007 | Freeman | 600/583 |
| 2007/0167872 A1 | 7/2007 | Freeman | 600/583 |
| 2007/0167873 A1 | 7/2007 | Freeman | 600/583 |
| 2007/0167874 A1 | 7/2007 | Freeman | 600/583 |
| 2007/0167875 A1 | 7/2007 | Freeman | 600/583 |
| 2007/0173739 A1 | 7/2007 | Chan | 600/583 |
| 2007/0173740 A1 | 7/2007 | Chan | 600/583 |
| 2007/0173741 A1 | 7/2007 | Boecker | 600/583 |
| 2007/0173742 A1 | 7/2007 | Freeman et al. | 600/583 |
| 2007/0173743 A1 | 7/2007 | Freeman | 600/583 |
| 2007/0173874 A1 | 7/2007 | Uschold | 606/181 |
| 2007/0173875 A1 | 7/2007 | Uschold | 606/181 |
| 2007/0173876 A1 | 7/2007 | Aylett | 606/181 |
| 2007/0176120 A1 | 8/2007 | Schwind et al. | 250/492.1 |
| 2007/0179356 A1 | 8/2007 | Wessel | 600/300 |
| 2007/0179404 A1 | 8/2007 | Escutia | 600/583 |
| 2007/0179405 A1 | 8/2007 | Emery | 600/583 |
| 2007/0179406 A1 | 8/2007 | DeNuzzio | 600/583 |
| 2007/0182051 A1 | 8/2007 | Harttig | 264/138 |
| 2007/0185412 A1 | 8/2007 | Boecker | 600/583 |
| 2007/0185515 A1 | 8/2007 | Stout | 606/181 |
| 2007/0185516 A1 | 8/2007 | Schosnig | 606/181 |
| 2007/0191702 A1 | 8/2007 | Yodfat | 600/365 |
| 2007/0191737 A1 | 8/2007 | Freeman | 600/583 |
| 2007/0191738 A1 | 8/2007 | Raney | 600/583 |
| 2007/0191739 A1 | 8/2007 | Roe | 600/583 |
| 2007/0193019 A1 | 8/2007 | Feldman | 29/592.1 |
| 2007/0193882 A1 | 8/2007 | Dai | 204/403.02 |
| 2007/0196240 A1 | 8/2007 | Boozer | 422/102 |
| 2007/0196242 A1 | 8/2007 | Boozer | 422/102 |
| 2007/0203514 A1 | 8/2007 | Flaherty | 606/181 |
| 2007/0203903 A1 | 8/2007 | Attaran | 707/5 |
| 2007/0205103 A1 | 9/2007 | Hodges | 204/403.01 |
| 2007/0207498 A1 | 9/2007 | Palmieri | 435/7.1 |
| 2007/0213601 A1 | 9/2007 | Freeman | 600/300 |
| 2007/0213637 A1 | 9/2007 | Boozer | 600/583 |
| 2007/0213682 A1 | 9/2007 | Haar | 604/500 |
| 2007/0213756 A1 | 9/2007 | Freeman | 606/181 |
| 2007/0218543 A1 | 9/2007 | Flaherty | 435/287.1 |
| 2007/0219346 A1 | 9/2007 | Trifiro | 530/308 |
| 2007/0219432 A1 | 9/2007 | Thompson | 600/300 |
| 2007/0219436 A1 | 9/2007 | Takase | 600/310 |
| 2007/0219462 A1 | 9/2007 | Briggs | 600/583 |
| 2007/0219463 A1 | 9/2007 | Briggs | 600/583 |
| 2007/0219572 A1 | 9/2007 | Deck | 606/181 |
| 2007/0219573 A1 | 9/2007 | Freeman | 606/183 |
| 2007/0219574 A1 | 9/2007 | Freeman | 606/185 |
| 2007/0225741 A1 | 9/2007 | Ikeda | 606/182 |
| 2007/0225742 A1 | 9/2007 | Abe | 606/182 |
| 2007/0227907 A1 | 10/2007 | Shah | 205/777.5 |
| 2007/0227911 A1 | 10/2007 | Wang | 205/792 |
| 2007/0227912 A1 | 10/2007 | Chatelier | 205/792 |
| 2007/0229085 A1 | 10/2007 | Kawai | 324/450 |
| 2007/0232872 A1 | 10/2007 | Prough | 600/316 |
| 2007/0232956 A1 | 10/2007 | Harman | 600/573 |
| 2007/0233013 A1 | 10/2007 | Schoenberg | 604/192 |
| 2007/0233166 A1 | 10/2007 | Stout | 606/182 |
| 2007/0233167 A1 | 10/2007 | Weiss | 606/182 |
| 2007/0233395 A1 | 10/2007 | Neel | 702/19 |
| 2007/0235329 A1 | 10/2007 | Harding | 204/403.01 |
| 2007/0235347 A1 | 10/2007 | Chatelier | 205/792 |
| 2007/0239068 A1 | 10/2007 | Rasch-Menges | 600/573 |
| 2007/0239188 A1 | 10/2007 | Boozer | 606/181 |
| 2007/0239189 A1 | 10/2007 | Freeman | 606/181 |
| 2007/0239190 A1 | 10/2007 | Alden | 606/181 |
| 2007/0240984 A1 | 10/2007 | Popovich | 204/403.01 |
| 2007/0240986 A1 | 10/2007 | Reymond | 204/412 |
| 2007/0244380 A1 | 10/2007 | Say | 600/347 |
| 2007/0244412 A1 | 10/2007 | Lav | 600/584 |
| 2007/0244498 A1 | 10/2007 | Steg | 606/181 |
| 2007/0244499 A1 | 10/2007 | Briggs | 606/182 |
| 2007/0249921 A1 | 10/2007 | Groll | 600/347 |
| 2007/0249962 A1 | 10/2007 | Alden | 600/583 |
| 2007/0249963 A1 | 10/2007 | Alden | 600/583 |
| 2007/0250099 A1 | 10/2007 | Flora | 606/181 |
| 2007/0251836 A1 | 11/2007 | Hsu | 205/792 |
| 2007/0254359 A1 | 11/2007 | Rezania | 435/325 |
| 2007/0255141 A1 | 11/2007 | Esenaliev | 600/475 |
| 2007/0255178 A1 | 11/2007 | Alvarez-Icaza | 600/583 |
| 2007/0255179 A1 | 11/2007 | Alvarez-Icaza | 600/583 |
| 2007/0255180 A1 | 11/2007 | Alvarez-Icaza | 600/583 |
| 2007/0255181 A1 | 11/2007 | Alvarez-Icaza | 600/583 |
| 2007/0255300 A1 | 11/2007 | Vanhiel | 606/181 |
| 2007/0255301 A1 | 11/2007 | Freeman | 606/181 |
| 2007/0255302 A1 | 11/2007 | Koeppel | 606/182 |
| 2007/0260271 A1 | 11/2007 | Freeman | 606/181 |
| 2007/0260272 A1 | 11/2007 | Weiss | 606/181 |
| 2007/0264721 A1 | 11/2007 | Buck | 436/150 |
| 2007/0265511 A1 | 11/2007 | Renouf | 600/319 |
| 2007/0265532 A1 | 11/2007 | Maynard | 600/477 |
| 2007/0265654 A1 | 11/2007 | Iio | 606/185 |
| 2007/0273901 A1 | 11/2007 | Baskeyfield | 358/1.9 |
| 2007/0273903 A1 | 11/2007 | Baskeyfield | 358/1.9 |
| 2007/0273904 A1 | 11/2007 | Robinson | 358/1.9 |
| 2007/0273928 A1 | 11/2007 | Robinson | 358/1.9 |
| 2007/0276197 A1 | 11/2007 | Harmon | 600/300 |
| 2007/0276211 A1 | 11/2007 | Mir | 600/345 |
| 2007/0276290 A1 | 11/2007 | Boecker | 600/583 |
| 2007/0276425 A1 | 11/2007 | Kim | 606/186 |
| 2007/0276621 A1 | 11/2007 | Davies | 702/104 |
| 2007/0278097 A1 | 12/2007 | Bhullar | 204/403.01 |
| 2007/0282186 A1 | 12/2007 | Gilmore | 600/365 |
| 2007/0282362 A1 | 12/2007 | Berg | 606/181 |
| 2007/0288047 A1 | 12/2007 | Thoes | 606/182 |
| 2007/0293743 A1 | 12/2007 | Monfre | 600/316 |
| 2007/0293744 A1 | 12/2007 | Monfre | 600/316 |
| 2007/0293790 A1 | 12/2007 | Bainczyk | 600/583 |
| 2007/0293882 A1 | 12/2007 | Harttig | 606/181 |
| 2007/0293883 A1 | 12/2007 | Horie | |
| 2007/0295616 A1 | 12/2007 | Harding | 205/777.5 |
| 2008/0004651 A1 | 1/2008 | Nicholls | 606/182 |
| 2008/0007141 A1 | 1/2008 | Deck | 310/328 |
| 2008/0009767 A1 | 1/2008 | Effenhauser | 600/583 |
| 2008/0009768 A1 | 1/2008 | Sohrab | 600/583 |
| 2008/0009892 A1 | 1/2008 | Freeman | 606/181 |
| 2008/0009893 A1 | 1/2008 | LeVaughn | 606/181 |
| 2008/0015425 A1 | 1/2008 | Douglas | 600/347 |
| 2008/0015623 A1 | 1/2008 | Deck | 606/181 |
| 2008/0017522 A1 | 1/2008 | Heller | 205/777.5 |
| 2008/0019870 A1 | 1/2008 | Newman | 422/68.1 |
| 2008/0021291 A1 | 1/2008 | Zocchi | 600/300 |
| 2008/0021293 A1 | 1/2008 | Schurman | 600/316 |
| 2008/0021295 A1 | 1/2008 | Wang | 600/347 |
| 2008/0021296 A1 | 1/2008 | Creaven | 600/365 |
| 2008/0021346 A1 | 1/2008 | Haar | 600/583 |
| 2008/0021490 A1 | 1/2008 | Briggs | 606/181 |
| 2008/0021491 A1 | 1/2008 | Freeman | 606/181 |
| 2008/0021492 A1 | 1/2008 | Freeman | 606/181 |
| 2008/0021493 A1 | 1/2008 | Levaughn | 606/181 |
| 2008/0021494 A1 | 1/2008 | Schmelzeisen | 606/181 |
| 2008/0027385 A1 | 1/2008 | Freeman | 604/117 |
| 2008/0031778 A1 | 2/2008 | Kramer | 422/68.1 |
| 2008/0033268 A1 | 2/2008 | Stafford | 600/345 |
| 2008/0033318 A1 | 2/2008 | Mace | 600/583 |

(56) References Cited

U.S. PATENT DOCUMENTS

| | | | |
|---|---|---|---|
| 2008/0033319 A1 | 2/2008 | Kloepfer | 600/583 |
| 2008/0033468 A1 | 2/2008 | Lathrop | 606/181 |
| 2008/0033469 A1 | 2/2008 | Winheim | 606/181 |
| 2008/0034834 A1 | 2/2008 | Schell | 73/1.02 |
| 2008/0034835 A1 | 2/2008 | Schell | 73/1.02 |
| 2008/0039885 A1 | 2/2008 | Purcell | 606/182 |
| 2008/0039886 A1 | 2/2008 | Shi | 606/182 |
| 2008/0039887 A1 | 2/2008 | Conway | 606/182 |
| 2008/0040919 A1 | 2/2008 | Griss | 29/777 |
| 2008/0045825 A1 | 2/2008 | Melker | 600/365 |
| 2008/0045992 A1 | 2/2008 | Schraga | 606/182 |
| 2008/0047764 A1 | 2/2008 | Lee | G08C 21/00 |
| 2008/0053201 A1 | 3/2008 | Roesicke | 73/61.41 |
| 2008/0057484 A1 | 3/2008 | Miyata | 434/739 |
| 2008/0058624 A1 | 3/2008 | Smart | 600/345 |
| 2008/0058626 A1 | 3/2008 | Miyata | 600/365 |
| 2008/0058631 A1 | 3/2008 | Draudt | 600/385 |
| 2008/0058847 A1 | 3/2008 | Abe | 606/181 |
| 2008/0058848 A1 | 3/2008 | Griffin | 606/182 |
| 2008/0058849 A1 | 3/2008 | Conway | 606/183 |
| 2008/0060424 A1 | 3/2008 | Babic | 73/61.41 |
| 2008/0064986 A1 | 3/2008 | Kraemer | 600/583 |
| 2008/0064987 A1 | 3/2008 | Escutia | 600/583 |
| 2008/0065130 A1 | 3/2008 | Patel | 606/181 |
| 2008/0065131 A1 | 3/2008 | List | 606/181 |
| 2008/0065132 A1 | 3/2008 | Trissel | 606/182 |
| 2008/0065133 A1 | 3/2008 | Kennedy | 606/182 |
| 2008/0065134 A1 | 3/2008 | Conway | 606/182 |
| 2008/0073224 A1 | 3/2008 | Diamond | 205/775 |
| 2008/0077048 A1 | 3/2008 | Escutia | 600/583 |
| 2008/0077167 A1 | 3/2008 | Flynn | 606/172 |
| 2008/0077168 A1 | 3/2008 | Nicholls | 606/182 |
| 2008/0081969 A1 | 4/2008 | Feldman | 600/322 |
| 2008/0081976 A1 | 4/2008 | Hodges | 600/345 |
| 2008/0082023 A1 | 4/2008 | Deck | 600/583 |
| 2008/0082116 A1 | 4/2008 | Lathrop | 606/181 |
| 2008/0082117 A1 | 4/2008 | Ruf | 606/182 |
| 2008/0086042 A1 | 4/2008 | Brister | 600/347 |
| 2008/0086044 A1 | 4/2008 | Brister | 600/365 |
| 2008/0086273 A1 | 4/2008 | Shults | 702/19 |
| 2008/0093227 A1 | 4/2008 | Diamond | 205/775 |
| 2008/0093228 A1 | 4/2008 | Diamond | 205/782 |
| 2008/0093230 A1 | 4/2008 | Diamond | 205/792 |
| 2008/0094804 A1 | 4/2008 | Reynolds | 361/727 |
| 2008/0097171 A1 | 4/2008 | Smart | 600/309 |
| 2008/0097241 A1 | 4/2008 | Maltezos | 600/576 |
| 2008/0097503 A1 | 4/2008 | Creaven | 606/182 |
| 2008/0098802 A1 | 5/2008 | Burke | 73/61.61 |
| 2008/0103396 A1 | 5/2008 | Johnson | 600/477 |
| 2008/0103415 A1 | 5/2008 | Roe | 600/583 |
| 2008/0103517 A1 | 5/2008 | Takemoto | 606/182 |
| 2008/0105024 A1 | 5/2008 | Creaven | 73/1.02 |
| 2008/0105568 A1 | 5/2008 | Wu | 205/780.5 |
| 2008/0108130 A1 | 5/2008 | Nakaminami | 435/287.1 |
| 2008/0108942 A1 | 5/2008 | Brister | 604/118 |
| 2008/0109024 A1 | 5/2008 | Berkovitch | 606/181 |
| 2008/0109025 A1 | 5/2008 | Yang | 606/182 |
| 2008/0109259 A1 | 5/2008 | Thompson | 705/3 |
| 2008/0114227 A1 | 5/2008 | Haar | 600/365 |
| 2008/0114228 A1 | 5/2008 | McCluskey | 600/365 |
| 2008/0118400 A1 | 5/2008 | Neel | 422/68.1 |
| 2008/0119703 A1 | 5/2008 | Brister | 600/347 |
| 2008/0119704 A1 | 5/2008 | Brister | 600/347 |
| 2008/0119706 A1 | 5/2008 | Brister | 600/365 |
| 2008/0119761 A1 | 5/2008 | Boecker | 600/583 |
| 2008/0119883 A1 | 5/2008 | Conway | 606/181 |
| 2008/0119884 A1 | 5/2008 | Flora | 606/182 |
| 2008/0121533 A1 | 5/2008 | Hodges | 205/775 |
| 2008/0125800 A1 | 5/2008 | List | 606/181 |
| 2008/0125801 A1 | 5/2008 | List | 606/181 |
| 2008/0134806 A1 | 6/2008 | Capriccio | 73/863.21 |
| 2008/0134810 A1 | 6/2008 | Neel | 73/866 |
| 2008/0135559 A1 | 6/2008 | Byrd | 220/506 |
| 2008/0140105 A1 | 6/2008 | Zhong | 606/182 |
| 2008/0144022 A1 | 6/2008 | Schulat | 356/213 |
| 2008/0146899 A1 | 6/2008 | Ruchti | 600/316 |
| 2008/0146966 A1 | 6/2008 | LeVaughn | 600/583 |
| 2008/0147108 A1 | 6/2008 | Kennedy | 606/182 |
| 2008/0149268 A1 | 6/2008 | Zhao | 156/299 |
| 2008/0149599 A1 | 6/2008 | Bohm | 216/94 |
| 2008/0152507 A1 | 6/2008 | Bohm | 417/44.1 |
| 2008/0154187 A1 | 6/2008 | Krulevitch | 604/48 |
| 2008/0154513 A1 | 6/2008 | Kovatchev | 702/19 |
| 2008/0159913 A1 | 7/2008 | Jung | 422/57 |
| 2008/0161664 A1 | 7/2008 | Mastrototaro | 600/347 |
| 2008/0161724 A1 | 7/2008 | Roe | 600/583 |
| 2008/0161725 A1 | 7/2008 | Wong | 600/583 |
| 2008/0166269 A1 | 7/2008 | Jansen | 422/63 |
| 2008/0167578 A1 | 7/2008 | Bryer | 600/583 |
| 2008/0167673 A1 | 7/2008 | Zhong | 606/181 |
| 2008/0188771 A1 | 8/2008 | Boecker | 600/583 |
| 2008/0194987 A1 | 8/2008 | Boecker | 600/583 |
| 2008/0194989 A1 | 8/2008 | Briggs | 600/583 |
| 2008/0208026 A1 | 8/2008 | Noujaim | 600/365 |
| 2008/0208079 A1 | 8/2008 | Hein | 600/583 |
| 2008/0210574 A1 | 9/2008 | Boecker | 205/777.5 |
| 2008/0214909 A1 | 9/2008 | Fuerst | 600/309 |
| 2008/0214917 A1 | 9/2008 | Boecker | 600/347 |
| 2008/0214919 A1 | 9/2008 | Harmon | 600/365 |
| 2008/0214956 A1 | 9/2008 | Briggs | 600/575 |
| 2008/0228212 A1 | 9/2008 | List | 606/182 |
| 2008/0249435 A1 | 10/2008 | Haar | 600/583 |
| 2008/0249554 A1 | 10/2008 | Freeman | 606/181 |
| 2008/0255598 A1 | 10/2008 | LeVaughn et al. | 606/183 |
| 2008/0262387 A1 | 10/2008 | List | 600/583 |
| 2008/0262388 A1 | 10/2008 | List | 600/583 |
| 2008/0267822 A1 | 10/2008 | List | 422/68.1 |
| 2008/0269723 A1 | 10/2008 | Mastrototaro | 604/890.1 |
| 2008/0269791 A1 | 10/2008 | Hoenes | 606/181 |
| 2008/0275365 A1 | 11/2008 | Guthrie | 600/584 |
| 2008/0275384 A1 | 11/2008 | Mastrototaro | 604/66 |
| 2008/0277291 A1 | 11/2008 | Heller | 205/777.5 |
| 2008/0277292 A1 | 11/2008 | Heller | 205/777.5 |
| 2008/0277293 A1 | 11/2008 | Heller | 205/777.5 |
| 2008/0277294 A1 | 11/2008 | Heller | 205/777.5 |
| 2008/0286149 A1 | 11/2008 | Roe | 422/58 |
| 2008/0294068 A1 | 11/2008 | Briggs | 600/583 |
| 2008/0300614 A1 | 12/2008 | Freeman | 606/181 |
| 2008/0318193 A1 | 12/2008 | Alvarez-Icaza | 434/262 |
| 2008/0319284 A1 | 12/2008 | Alvarez-Icaza | 600/309 |
| 2008/0319291 A1 | 12/2008 | Freeman | 600/347 |
| 2009/0005664 A1 | 1/2009 | Freeman | 600/347 |
| 2009/0020438 A1 | 1/2009 | Hodges | 205/782 |
| 2009/0024009 A1 | 1/2009 | Freeman | |
| 2009/0026075 A1 | 1/2009 | Harding | 204/403.14 |
| 2009/0026091 A1 | 1/2009 | Harding | 205/777.5 |
| 2009/0027040 A1 | 1/2009 | Kermani | 324/123 |
| 2009/0029479 A1 | 1/2009 | Docherty | 436/149 |
| 2009/0030441 A1 | 1/2009 | Freeman et al. | 600/583 |
| 2009/0043177 A1 | 2/2009 | Milledge | 600/309 |
| 2009/0043183 A1 | 2/2009 | Kermani | 600/365 |
| 2009/0048536 A1 | 2/2009 | Freeman | 600/583 |
| 2009/0054813 A1 | 2/2009 | Freeman | 600/584 |
| 2009/0057146 A1 | 3/2009 | Teodorczyk | 204/403.01 |
| 2009/0069716 A1 | 3/2009 | Freeman | 600/583 |
| 2009/0084687 A1 | 4/2009 | Chatelier | 205/792 |
| 2009/0105572 A1 | 4/2009 | Malecha | 600/365 |
| 2009/0105573 A1 | 4/2009 | Malecha | 600/365 |
| 2009/0112123 A1 | 4/2009 | Freeman | 600/583 |
| 2009/0112155 A1 | 4/2009 | Zhao | 604/67 |
| 2009/0112180 A1 | 4/2009 | Krulevitch | 604/506 |
| 2009/0112185 A1 | 4/2009 | Krulevitch | 604/523 |
| 2009/0124932 A1 | 5/2009 | Freeman | 606/181 |
| 2009/0131829 A1 | 5/2009 | Freeman | 600/583 |
| 2009/0131830 A1 | 5/2009 | Freeman | 600/583 |
| 2009/0131964 A1 | 5/2009 | Freeman | 606/181 |
| 2009/0131965 A1 | 5/2009 | Freeman | 606/181 |
| 2009/0137930 A1 | 5/2009 | Freeman | 600/583 |
| 2009/0138032 A1 | 5/2009 | Freeman | 606/181 |
| 2009/0139300 A1 | 6/2009 | Pugh | 73/1.36 |
| 2009/0177117 A1 | 7/2009 | Amano et al. | 600/583 |
| 2009/0184004 A1 | 7/2009 | Chatelier | 205/777.5 |
| 2009/0187351 A1 | 7/2009 | Orr | 702/19 |
| 2009/0192410 A1 | 7/2009 | Freeman | 600/583 |

(56) References Cited

U.S. PATENT DOCUMENTS

| | | | |
|---|---|---|---|
| 2009/0192411 A1 | 7/2009 | Freeman | 600/583 |
| 2009/0196580 A1 | 8/2009 | Freeman | 386/124 |
| 2009/0204025 A1 | 8/2009 | Marsot | 600/573 |
| 2009/0216100 A1 | 8/2009 | Ebner | 600/347 |
| 2009/0237262 A1 | 9/2009 | Smith | 340/634 |
| 2009/0240127 A1 | 9/2009 | Ray | 600/365 |
| 2009/0247838 A1 | 10/2009 | Cummings | 600/309 |
| 2009/0247982 A1 | 10/2009 | Krulevitch | 604/500 |
| 2009/0259146 A1 | 10/2009 | Freeman | 600/583 |
| 2009/0270765 A1 | 10/2009 | Ghesquiere et al. | 600/583 |
| 2009/0280551 A1 | 11/2009 | Cardosi | 435/190 |
| 2009/0281457 A1 | 11/2009 | Faulkner | 600/583 |
| 2009/0281458 A1 | 11/2009 | Faulkner | 600/583 |
| 2009/0281459 A1 | 11/2009 | Faulkner | 600/583 |
| 2009/0301899 A1 | 12/2009 | Hodges | 205/777.5 |
| 2009/0302872 A1 | 12/2009 | Haggett | 324/715 |
| 2009/0302873 A1 | 12/2009 | Haggett | 324/724 |
| 2009/0322630 A1 | 12/2009 | Friman | 343/720 |
| 2009/0325307 A1 | 12/2009 | Haggett | 436/150 |
| 2010/0016700 A1 | 1/2010 | Sieh | 600/365 |
| 2010/0018878 A1 | 1/2010 | Davies | 205/782 |
| 2010/0030110 A1 | 2/2010 | Choi | 600/583 |
| 2010/0041084 A1 | 2/2010 | Stephens | 435/14 |
| 2010/0113981 A1 | 5/2010 | Oki et al. | 600/587 |
| 2010/0198107 A1 | 8/2010 | Groll et al. | 600/583 |
| 2010/0256525 A1 | 10/2010 | List et al. | 600/583 |
| 2010/0292611 A1 | 11/2010 | Lum et al. | 600/583 |
| 2010/0324452 A1 | 12/2010 | Freeman et al. | 600/583 |
| 2011/0077478 A1 | 3/2011 | Freeman et al. | 600/309 |
| 2011/0077553 A1 | 3/2011 | Alroy | 600/573 |
| 2011/0098541 A1 | 4/2011 | Freeman et al. | 600/309 |
| 2012/0149999 A1 | 6/2012 | Freeman et al. | 600/309 |
| 2012/0232425 A1 | 9/2012 | Freeman et al. | 600/583 |
| 2012/0271197 A1 | 10/2012 | Castle et al. | 600/583 |
| 2012/0296233 A9 | 11/2012 | Freeman | 600/583 |

FOREIGN PATENT DOCUMENTS

| | | | |
|---|---|---|---|
| EP | 0199484 A2 | 10/1986 | |
| EP | 0 951 939 | 10/1999 | |
| EP | 0 985 376 | 5/2000 | |
| EP | 1 101 443 | 5/2001 | |
| EP | 1101443 | 5/2001 | |
| EP | 1 157 660 | 11/2001 | |
| EP | 1486766 | 12/2004 | G01N 1/00 |
| EP | 1790288 A1 | 5/2007 | |
| EP | 1881322 A1 | 1/2008 | G01N 33/487 |
| EP | 2039294 A1 | 3/2009 | |
| EP | 2130493 A1 | 12/2009 | A61B 5/15 |
| FR | 2 555 432 A | 5/1985 | |
| GB | 233936 A | 6/1999 | |
| GB | 2335860 A | 10/1999 | |
| GB | 2335990 A | 10/1999 | |
| JP | 9-276235 | 10/1997 | A61B 5/00 |
| WO | WO 93/02720 | 2/1993 | A61M 5/00 |
| WO | WO 93/12726 | 7/1993 | A61B 17/34 |
| WO | WO 95/06240 | 3/1995 | |
| WO | WO 97/11883 A1 | 4/1997 | |
| WO | WO 98/24373 | 6/1998 | A61B 17/00 |
| WO | WO 99/07431 A1 | 2/1999 | A61M 25/06 |
| WO | WO 01/15807 | 3/2001 | |
| WO | WO 01/72220 A | 10/2001 | |
| WO | WO 01/95806 | 12/2001 | |
| WO | WO 03/082091 A2 | 10/2003 | |
| WO | WO 03/088851 A1 | 10/2003 | A61B 17/14 |
| WO | WO 2004/045375 | 6/2004 | |
| WO | WO 2004/112612 A1 | 12/2004 | |
| WO | WO 2005045414 A1 | 5/2005 | C12Q 1/00 |
| WO | WO 2005/104948 A1 | 11/2005 | |
| WO | WO 2005/120365 A1 | 12/2005 | |
| WO | WO 2007/010087 A2 | 1/2007 | A61B 5/151 |
| WO | WO 2007/088905 A1 | 8/2007 | A61B 5/1473 |
| WO | WO 2008/085052 A2 | 7/2008 | A61B 5/15 |
| WO | WO 2010109461 A1 | 9/2010 | A61B 5/151 |

OTHER PUBLICATIONS

Wolfbeis et al. (Sol-gel based glucose biosensors employing optical oxygen transducers, and a method for compensating for variable oxygen background, Biosensors & Bioelectronics 15 (2000) pp. 69-76).

G. Jarzabek, Z. Borkowska, On the Real Surface Area of Smooth Solid Electrodes, 1997, Electrochimica Acta, vol. 42, No. 19, pp. 2915-2918.

A. Bott, W. Heineman, Chronocoulometry, Current Separations, 2004, 20, pp. 121.

* cited by examiner

METHOD AND APPARATUS FOR ANALYTE MEASUREMENT TEST TIME

CROSS-REFERENCE TO RELATED CASES

This application is a continuation-in-part of U.S. Ser. No. 11/813,014 filed Dec. 30, 2005, which is a filing under 35 U.S.C. §371 of PCT/US05/47480 filed Dec. 30, 2005, which application claims the benefit of U.S. Ser. No. 60/640,879 filed Dec. 30, 2004, all of which applications are fully incorporated herein by reference. This application is also a continuation in part of U.S. Ser. No. 10/540,912, filed Dec. 15, 2003.

BACKGROUND OF THE INVENTION

1. Technical Field

The technical field relates to analyte measurement, and more specifically, the amount of time it takes to complete an analyte measurement.

2. Background Art

Lancing devices are known in the medical health-care products industry for piercing the skin to produce blood for analysis. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. The device may be held against the skin and mechanically triggered to ballistically launch the lancet. Unfortunately, the pain associated with each lancing event using known technology discourages patients from testing. In addition to vibratory stimulation of the skin as the driver impacts the end of a launcher stop, known spring based devices have the possibility of firing lancets that harmonically oscillate against the patient tissue, causing multiple strikes due to recoil. This recoil and multiple strikes of the lancet is one major impediment to patient compliance with a structured glucose monitoring regime.

Success rate generally encompasses the probability of producing a blood sample with one lancing action, which is sufficient in volume to perform the desired analytical test. The blood may appear spontaneously at the surface of the skin, or may be "milked" from the wound. Milking generally involves pressing the side of the digit, or in proximity of the wound to express the blood to the surface. In traditional methods, the blood droplet produced by the lancing action must reach the surface of the skin to be viable for testing.

When using existing methods, blood often flows from the cut blood vessels but is then trapped below the surface of the skin, forming a hematoma. In other instances, a wound is created, but no blood flows from the wound. In either case, the lancing process cannot be combined with the sample acquisition and testing step. Spontaneous blood droplet generation with current mechanical launching system varies between launcher types but on average it is about 50% of lancet strikes, which would be spontaneous. Otherwise milking is required to yield blood. Mechanical launchers are unlikely to provide the means for integrated sample acquisition and testing if one out of every two strikes does not yield a spontaneous blood sample.

Many diabetic patients (insulin dependent) are required to self-test for blood glucose levels five to six times daily. The large number of steps required in traditional methods of glucose testing ranging from lancing, to milking of blood, applying blood to the test strip, and getting the measurements from the test strip discourages many diabetic patients from testing their blood glucose levels as often as recommended. Tight control of plasma glucose through frequent testing is therefore mandatory for disease management. The pain associated with each lancing event further discourages patients from testing. Additionally, the wound channel left on the patient by known systems may also be of a size that discourages those who are active with their hands or who are worried about healing of those wound channels from testing their glucose levels.

Another problem frequently encountered by patients who must use lancing equipment to obtain and analyze blood samples is the amount of manual dexterity and hand-eye coordination required to properly operate the lancing and sample testing equipment due to retinopathies and neuropathies particularly, severe in elderly diabetic patients. For those patients, operating existing lancet and sample testing equipment can be a challenge. Once a blood droplet is created, that droplet must then be guided into a receiving channel of a small test strip or the like. If the sample placement on the strip is unsuccessful, repetition of the entire procedure including re-lancing the skin to obtain a new blood droplet is necessary.

Early methods of using test strips required a relatively substantial volume of blood to obtain an accurate glucose measurement. This large blood requirement made the monitoring experience a painful one for the user since the user may need to lance deeper than comfortable to obtain sufficient blood generation. Alternatively, if insufficient blood is spontaneously generated, the user may need to "milk" the wound to squeeze enough blood to the skin surface. Neither method is desirable as they take additional user effort and may be painful. The discomfort and inconvenience associated with such lancing events may deter a user from testing their blood glucose levels in a rigorous manner sufficient to control their diabetes.

A further impediment to patient compliance is the amount of time it takes for a user to obtain an analyte measurement using known devices. There are typically several devices in separate packaging that are typically brought together to perform the testing. These multiple devices such as test strips, lancets, a meter, and/or a lancet launcher all increase the complexity and burden on a user.

There is a need to provide methods for reducing the total test time for a user to complete an analyte measurements using analyte measurement devices.

SUMMARY OF THE INVENTION

Accordingly, an object of the present invention is to provide a method for improving analyte measurement test time and convenience.

Another object of the present invention is to provide a method for improving glucose measurement test time and convenience.

Yet another embodiment of the present invention is to provide a method for measuring an analyte with an analyte measurement device in less than 10 seconds.

A further object of the present invention is to provide a method for measuring analyte with an analyte measurement device that has penetrating members, that is quick and does not require the user to directly handle the penetrating members Another object of the present invention is to provide a method for measuring analyte with an analyte measurement device that has penetrating members, that is quick and does not require the user to remove and dispose of the penetrating members from the analyte measurement device.

Yet another object of the present invention is to provide a method for measuring analyte with an analyte measurement device that has penetrating members, that is quick and where the analyte measure device is ready for the next lancing event without having to dispose of the used penetrating member or a used analyte detecting member.

These and other objects of the present invention are achieved with a disposable biosensor test strip that includes a plurality of penetrating members. Each penetrating member is associated with a capillary chamber that has a depth suitable for capillary flow of blood and holds a volume of less than about 1.0 µl of the blood sample. A working electrode and a counter or reference electrode are disposed within the capillary chamber. A reagent is proximal to or in contact with at least the working electrode. The reagent includes an enzyme and a mediator. The reagent reacts with glucose to produce an electroactive reaction product. A blood sample, containing glucose, is applied into the capillary chamber. The capillary chamber directs capillary flow of the blood sample into contact with the reagent to cause the blood sample to at least partially solubilize or hydrate the reagent. The blood sample is detected in the capillary chamber. The electroactive reaction product is electro-oxidized or electro-reduced at the working electrode. Within 10 seconds after detecting, a determination is made of glucose concentration and a readout of the measurement is provided. The glucose determination is made by correlating the electro-oxidized or electro-reduced electroactive reaction product to the concentration of glucose in the blood sample.

In another embodiment of the present invention, a disposable biosensor test strip and a plurality of penetrating members are provided. Each penetrating member is associated with a capillary chamber that has a depth suitable for capillary flow of blood and holds a volume of less than about 1.0 µl of the blood sample. A working electrode and a counter or reference electrode are disposed within the capillary chamber. A reagent is proximal to or in contact with at least the working electrode. The reagent includes an enzyme and a mediator and reacts with glucose to produce an electroactive reaction product. A blood sample containing glucose is applied into the capillary chamber. The capillary chamber directing capillary flow of the blood sample into contact with the reagent to cause the blood sample to at least partially solubilize or hydrate the reagent; The blood sample is detected in the capillary chamber and the electroactive reactive product is electrooxidized at the working electrode. Within 10 seconds after the detecting step, a readout of the glucose concentration in the blood sample is made. The determination of glucose is made by correlating the electrooxidized electroactive reaction product to the concentration of glucose in the blood sample.

DESCRIPTION OF THE SPECIFIC EMBODIMENTS

Figure 1:
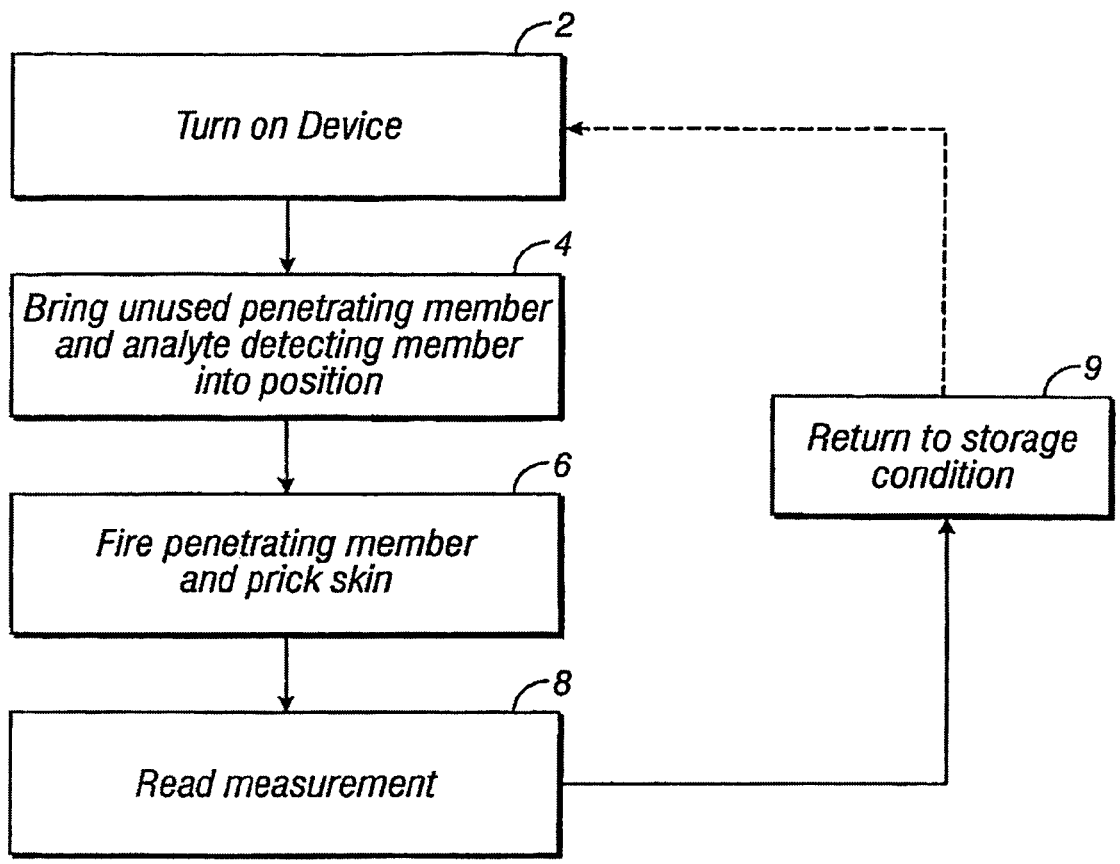
FIG. 1 is a flow chart illustrating one method of the present invention.

The present invention provides a solution for body fluid sampling. Specifically, some embodiments of the present invention provide improved devices and methods for storing a sampling device. The invention may use a high density penetrating member design. It may use penetrating members of smaller size, such as but not limited to diameter or length, than those of conventional penetrating members known in the art. The device may be used for multiple lancing events without having to remove a disposable from the device. The invention may provide improved sensing capabilities. At least some of these and other objectives described herein will be met by embodiments of the present invention.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

In one embodiment of the present invention, a method is provided for doing an analyte measurement by a user using an analyte measurement device in three steps. In a first step, a penetrating member and unused analyte detecting member of the analyte measurement device are presented into an active position. In a second step, the penetrating member is fired to prick the skin and bring a fluid sample to the analyte-detecting member. In a third step, the analyte level is measured. In one embodiment, these three steps occur in less than 10 seconds. In another embodiment, these steps occur in less than 7 seconds. The analyte level can be displayed to the use, and a value of the analyte level can be stored in or out of the analyte measurement device.

These three steps can be performed without the user directly handling the penetrating member to obtain a fresh penetrating member or load the penetrating member, and/or without the user coding the analyte measurement device. Blood is applied to an analyte detection member during lancing. Application of blood to an analyte detection member during lancing occurs without removal and disposal of penetrating members from the analyte measurement device. The three steps can be performed without a separate step of apply blood to a analyte detection member after lancing. The second step can be performed without milking a wound. The second step can be performed using at least one of a penetrating member driver selected from, spring based, electromechanical based, magnetic driver based, and nanomuscle based.

The second step can be performed with controlled velocity and depth of penetration, as more fully described hereafter. The analyte measurement device can be returned to a storage condition without having to dispose of a used penetrating member or used analyte detecting members. The analyte measurement device is ready for the next lancing event without having to dispose of the used penetrating member or the used analyte detecting member. In one embodiment, a time from pressing an on button of the analyte measurement device to lancing and measuring the analyte level is no more than 10 seconds.

From the moment the user thinks that it is time to do an analyte measurement (and begins the test process, reaches for the analyte measurement device, or initiates movement to begin the testing) to the time that a reading appears, in one embodiment, the present invention desires to be 10 seconds or less.

The test time breaks down into smaller pieces. The user will desire to do a test and then grab their measurement kit. In some embodiments, the user will take some action to turn on the analyte measurement device and take some action to prepare it. The user would hold the analyte measurement device to their skin and then first with some action by the user. Thus so far, the user will turn on the analyte measurement device, prepare it, and fire it. This may be combined into one. The time it takes is about 2 seconds to fire, 2 process to interact, and 4 seconds to get your readings.

A user right now will take about 20 seconds if certain steps are skipped. If the proper steps are taken then it takes a user about a minute. It is unlikely that a user may improve by a second or two if a second person helps. The speed is based on someone with dexterity to do things quickly. In one embodiment, the present invention provides a testing regime that removes much of the user variability and dexterity to testing.

In one embodiment of the present invention, the user does not need to dispose of or handle waste materials after each testing event, the user does not need to put the lancer back in place, the via back in place, or meter back in place. The present invention can offer a single analyte measurement device. The present invention can allow a user to get their reading and the put the analyte measurement device back down to where they had it. Whatever the user needs to do to return the analyte measurement device to their normal state or storage state is the end point of the time measurement.

The present invention removes taking a strip out of a vial, putting a strip into a meter, disposing of the strip, eliminate the need to grab a separate lancing device, eliminate the transfer step from a finger to a test strip.

The starting point for measuring may be when they open the carrying case or grabbing the test strip vial (to begin a test process). This may involve press the button or slide the slider to produce the test strip from the analyte measurement device. The step of physically preparing the strip is removed. Some users will leave the meter in a carrying case.

The present invention is the lower test time and the removal of certain steps. The present invention provides a convenience factor. Even though some steps will be reduced in time, the number of steps to reach a reading is improved. The user may wait less, but there is no reduction in convenience. The absolute time is more of a benefit of reduced steps. Even the automatically dispensing test strip devices still have the step of placing the strip and then removing it when done. There are no elimination of steps.

In the present invention, opening a latch or other trigger on the analyte measurement device may be used to prepare the analyte measurement device to have more device steps performed by fewer user steps. A latch may be opened and this may allow the analyte measurement device to power up and advance for next lancing event.

FIG. 1 is a flow chart of one embodiment of a method of the present invention. The analyte measurement device may be turned on at step 2. In some embodiments, the turn on at step 2 also performs the bringing of an unused penetrating member (and analyte detecting member as the case may be) into position. Some embodiments of the present invention has an explicit step 4 for bringing an unused penetrating member and analyte detecting member into position. Step 6 shows that the user may fire the analyte measurement device by a variety of methods including but not limited to pressing a button on the analyte measurement device. The firing will prick the skin and bring a blood sample into the analyte measurement device. The user then waits to see a measurement at step 8. At step 9, the user replaces the analyte measurement device into its storage condition, perhaps in a carrying case or by simply placing it back where the user stores testing devices. As indicated by the phantom line, the user will proceed back to step 2 when time comes for the next lancing event.

The present invention desires to complete the end-to-end testing process in less than 10 seconds. In some embodiments, the testing process is completed in less than 11, 12, 13, 14, 15, 16, 17, 18, 19, or 20 seconds. The present invention provides greater convenience by eliminating certain step but still arrive at the same end result of obtaining an analyte measurement.

It should be understood that one way to view the present invention is the number of steps performed by the user and the number of steps performed by the analyte measurement device. The present invention shifts the number of steps performed by the user and minimizes those steps while increasing the number of steps performed by analyte measurement device. Thus in one embodiment, the user may perform four steps (turn on, activate new penetrating member/analyte detecting member, pick skin, return meter to storage condition), the analyte measurement device will perform additional steps not seen by the user (rotate cartridge to bring new penetrating member in position, obtain sample from skin prick, transfer sample to detecting member, store used penetrating member, store used analyte testing devices. The present invention involves removing some steps completely and shifting many of the steps into the analyte measurement device.

In another embodiment of the present invention, a method of analyte measurement by a user uses an analyte measurement device in four steps. In the first step, a decision is made to test. In the second step, a penetrating member and unused analyte detecting member of the analyte measurement device is presented into an active position. In the third step, the penetrating member is fired to prick the skin and bring a fluid sample to the analyte detecting member. In the fourth step, the analyte level is measured. These four steps occur in no more than 1 minute. In various embodiments, steps one through four occur in more than, 30 seconds, 15 seconds, 10 seconds, and the like.

In another embodiment of the present invention, a method of analyte measurement is performed with an analyte measurement device in four steps. In a first step, a penetrating member and unused analyte detecting member of the analyte measurement device is presented into an active position by rotating a disposabe device to align in an active position. Seals covering the penetrating member and analyte detecting member are removed. In a second step, the penetrating member is fired to prick the skin using a driver to advance and retract from the skin to create a wound from which body fluid expresses. In a third step, a fluid sample is brought to the analyte detecting member by providing a sample capture structure positioned to contact body fluid expressed from the wound. In a fourth step, the analyte levels are measured. In one embodiment, these four steps occur in no more than 10 seconds. In various embodiments, these four steps are performed without the user, directly handling the penetrating member to obtain a fresh penetrating member or load the penetrating member, or coding the analyte measurement device.

In one embodiment, the four steps are performed without a separate step of apply blood to a analyte detection member after lancing. In another embodiment, the second and third steps are performed without milking a wound.

The analyte level can be displayed to the use, and a value of the analyte level can be stored in or out of the analyte measurement device. Blood is applied to an analyte detection member during lancing. Application of blood to an analyte detection member during lancing occurs without removal and disposal of penetrating members from the analyte measurement device.

In one embodiment, the second and third steps are performed using at least one of a penetrating member driver selected from, spring based, electro-mechanical based, magnetic driver based, and nanomuscle based. In another embodiment, the third step is performed with controlled velocity and depth of penetration.

The analyte measurement device can be returned to a storage condition without having to dispose of a used penetrating member or used analyte detecting members. The analyte measurement device is ready for the next lancing event without having to dispose of the used penetrating member or the used analyte detecting member. In one embodiment, a time from pressing an on button of the analyte measurement device to lancing and measuring the analyte level is no more than 10 seconds. In another embodiment, there is no disposal of a used analyte detecting member and a used penetrating member after each lancing step. In another embodiment, the four steps are performed without a disposal or handling of waste step.

The present invention may be used with a variety of different penetrating member drivers. It is contemplated that these penetrating member drivers may be spring based, solenoid based, magnetic driver based, nanomuscle based, or based on any other mechanism useful in moving a penetrating member along a path into tissue. It should be noted that the present invention is not limited by the type of driver used with the penetrating member feed mechanism. One suitable penetrating member driver for use with the present invention is shown in FIG. 1. This is an embodiment of a solenoid type electromagnetic driver that is capable of driving an iron core or slug mounted to the penetrating member assembly using a direct current (DC) power supply. The electromagnetic driver includes a driver coil pack that is divided into three separate coils along the path of the penetrating member, two end coils and a middle coil. Direct current is alternated to the coils to advance and retract the penetrating member. Although the driver coil pack is shown with three coils, any suitable number of coils may be used, for example, 4, 5, 6, 7 or more coils may be used.

Figure 2:
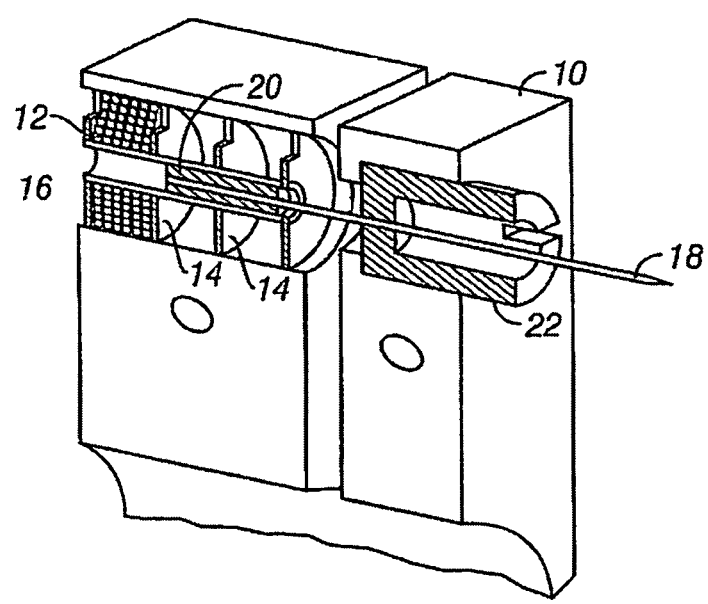
FIG. 2 illustrates an embodiment of a penetrating member driver that can used with the methods of the present invention.
Figure 3A:
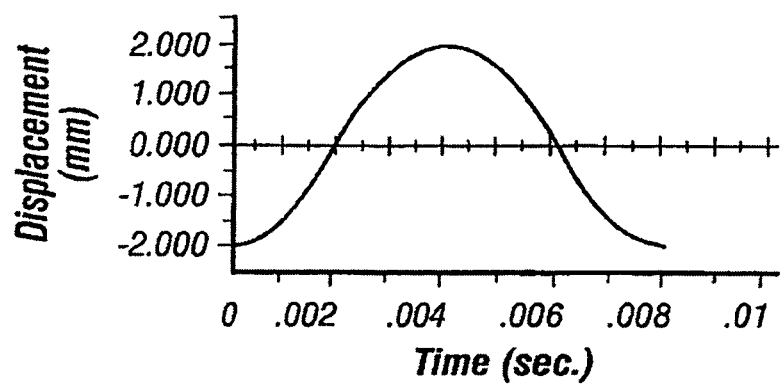
FIGS. 3(a) and 3(b) illustrate embodiments of displacement and velocity profiles, respectively, of a harmonic spring/mass powered driver that can be used with the methods of the present invention.
Figure 3B:
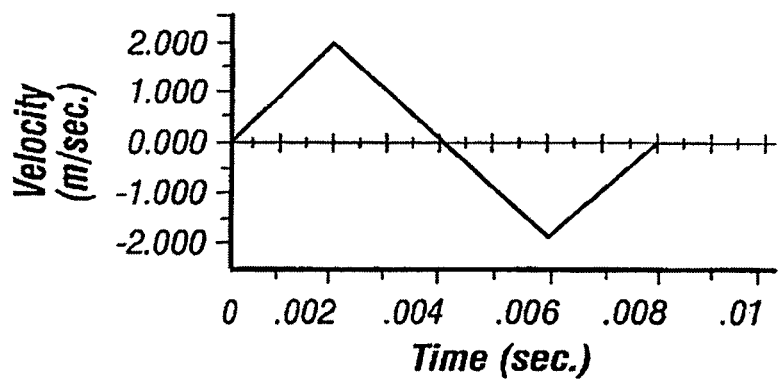
Figure 3C:
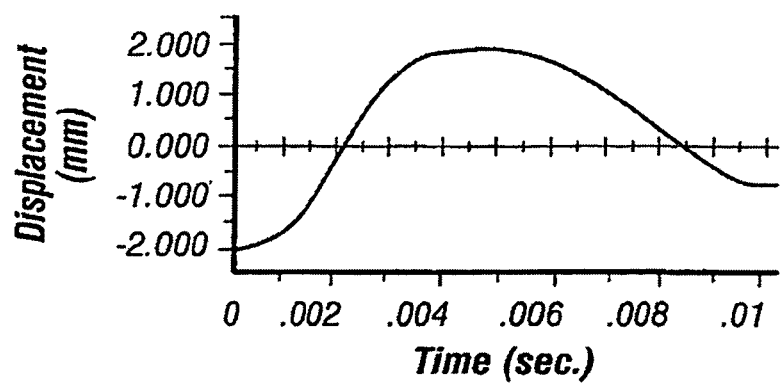
FIG. 3(c) illustrates an embodiment of a controlled displacement profile that can be utilized with the methods of the present invention.
Figure 3D:
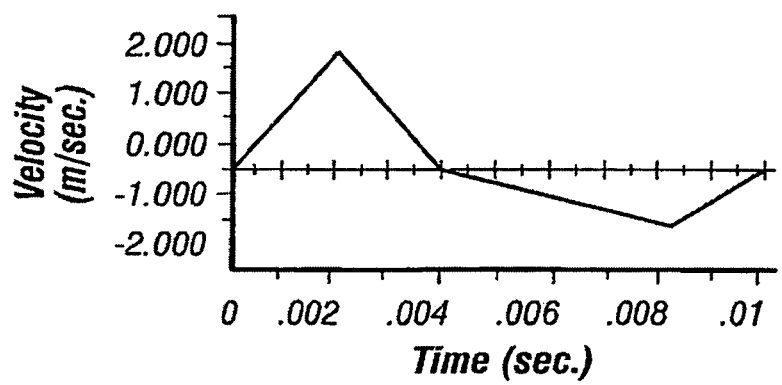
FIG. 3(d) illustrates an embodiment of a the controlled velocity profile that can be used with the methods of the present invention.

Referring to the embodiment of FIG. 2, a stationary iron housing 10 may contain the driver coil pack with a first coil 12 flanked by iron spacers 14 which concentrate the magnetic flux at the inner diameter creating magnetic poles. The inner insulating housing 16 isolates the penetrating member 18 and iron core 20 from the coils and provides a smooth, low friction guide surface. The penetrating member guide 22 further centers the penetrating member 18 and iron core 20. The penetrating member 18 is protracted and retracted by alternating the current between the first coil 12, the middle coil, and the third coil to attract the iron core 20. Reversing the coil sequence and attracting the core and penetrating member back into the housing retracts the penetrating member. The penetrating member guide 22 also serves as a stop for the iron core 20 mounted to the penetrating member 18.

As discussed above, analyte measurement devices which employ spring or cam driving methods have a symmetrical or nearly symmetrical actuation displacement and velocity profiles on the advancement and retraction of the penetrating member. In most of the available analyte measurement devices, once the launch is initiated, the stored energy determines the velocity profile until the energy is dissipated. Controlling impact, retraction velocity, and dwell time of the penetrating member within the tissue can be useful in order to achieve a high success rate while accommodating variations in skin properties and minimize pain. Advantages can be achieved by taking into account of the fact that tissue dwell time is related to the amount of skin deformation as the penetrating member tries to puncture the surface of the skin and variance in skin deformation from patient to patient based on skin hydration.

In this embodiment, the ability to control velocity and depth of penetration may be achieved by use of a controllable force driver where feedback is an integral part of driver control. Such drivers can control either metal or polymeric penetrating members or any other type of tissue penetration element. The dynamic control of such a driver is illustrated in FIG. 3(*c*) which illustrates an embodiment of a controlled displacement profile and FIG. 3(*d*) which illustrates an embodiment of a the controlled velocity profile. These are compared to FIGS. 3(*a*) and 3(*b*), which illustrate embodiments of displacement and velocity profiles, respectively, of a harmonic spring/mass powered driver. Reduced pain can be achieved by using impact velocities of greater than about 2 m/s entry of a tissue penetrating element, such as a lancet, into tissue. Other suitable embodiments of the penetrating member driver are described in commonly assigned, copending U.S. patent application Ser. No. 10/127,395, filed Apr. 19, 2002 and previously incorporated herein.

Figure 4:
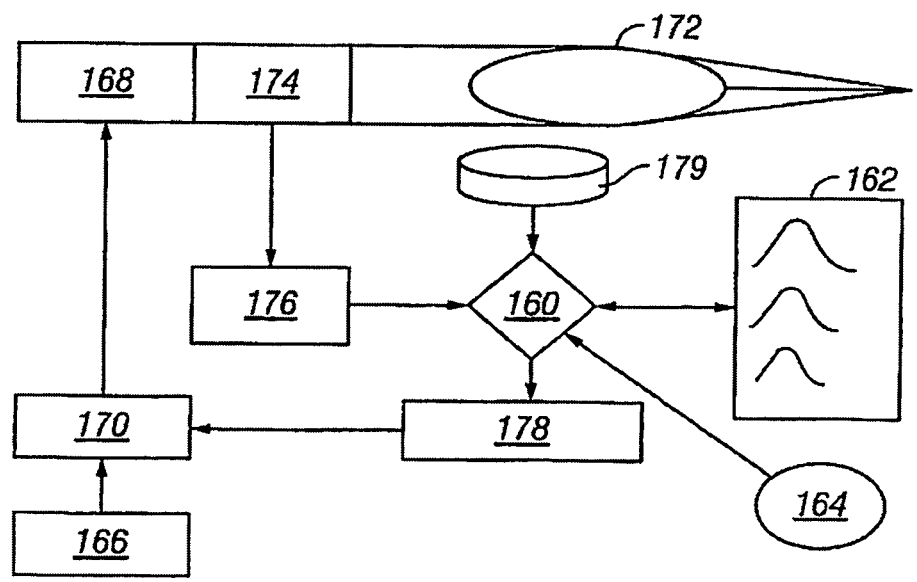
FIG. 4 illustrates a feedback loop and a processor that can be used with the methods of the present invention.

FIG. 4 illustrates the operation of a feedback loop using a processor 60. The processor 60 stores profiles 62 in non-volatile memory. A user inputs information 64 about the desired circumstances or parameters for a lancing event. The processor 60 selects a driver profile 62 from a set of alternative driver profiles that have been preprogrammed in the processor 60 based on typical or desired analyte measurement device performance determined through testing at the factory or as programmed in by the operator. The processor 60 may customize by either scaling or modifying the profile based on additional user input information 64. Once the processor has chosen and customized the profile, the processor 60 is ready to modulate the power from the power supply 66 to the penetrating member driver 68 through an amplifier 70. The processor 60 may measure the location of the penetrating member 72 using a position sensing mechanism 74 through an analog to digital converter 76 linear encoder or other such transducer. Examples of position sensing mechanisms have been described in the embodiments above and may be found in the specification for commonly assigned, copending U.S. patent application Ser. No. 10/127,395, filed Apr. 19, 2002 and previously incorporated herein. The processor 60 calculates the movement of the penetrating member by comparing the actual profile of the penetrating member to the predetermined profile. The processor 60 modulates the power to the penetrating member driver 68 through a signal generator 78, which may control the amplifier 70 so that the actual velocity profile of the penetrating member does not exceed the predetermined profile by more than a preset error limit. The error limit is the accuracy in the control of the penetrating member.

After the lancing event, the processor 60 can allow the user to rank the results of the lancing event. The processor 60 stores these results and constructs a database 80 for the individual user. Using the database 79, the processor 60 calculates the profile traits such as degree of painlessness, success rate, and blood volume for various profiles 62 depending on user input information 64 to optimize the profile to the individual user for subsequent lancing cycles. These profile traits depend on the characteristic phases of penetrating member advancement and retraction. The processor 60 uses these calculations to optimize profiles 62 for each user. In addition to user input information 64, an internal clock allows storage in the database 79 of information such as the time of day to generate a time stamp for the lancing event and the time between lancing events to anticipate the user's diurnal needs. The database stores information and statistics for each user and each profile that particular user uses.

In addition to varying the profiles, the processor 60 can be used to calculate the appropriate penetrating member diameter and geometry suitable to realize the blood volume required by the user. For example, if the user requires about 1-5 μl volume of blood, the processor 60 may select a 200 micron diameter penetrating member to achieve these results. For each class of lancet, both diameter and lancet tip geometry, is stored in the processor 60 to correspond with upper and lower limits of attainable blood volume based on the predetermined displacement and velocity profiles.

The analyte measurement device is capable of prompting the user for information at the beginning and the end of the lancing event to more adequately suit the user. The goal is to either change to a different profile or modify an existing profile. Once the profile is set, the force driving the penetrating member is varied during advancement and retraction to follow the profile. The method of lancing using the analyte measurement device comprises selecting a profile, lancing according to the selected profile, determining lancing profile traits for each characteristic phase of the lancing cycle, and optimizing profile traits for subsequent lancing events.

Figure 5:
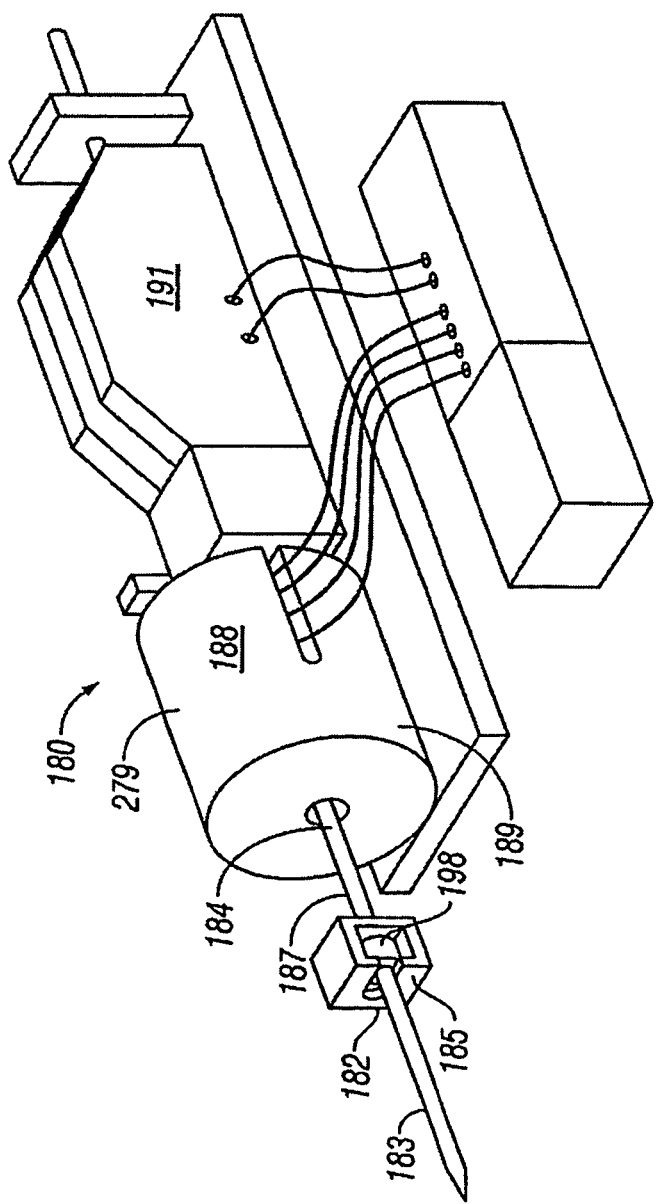
FIG. 5 illustrates a tissue penetration device, more specifically, a lancing device and a controllable driver coupled to a tissue penetration element, that can be used with the methods of the present invention.

FIG. 5 illustrates an embodiment of an analyte measurement device, more specifically, a lancing device 80 that includes a controllable driver 79 coupled to a tissue penetration element. The lancing device 80 has a proximal end 81 and a distal end 82. At the distal end 82 is the tissue penetration element in the form of a penetrating member 83, which is coupled to an elongate coupler shaft 84 by a drive coupler 85. The elongate coupler shaft 84 has a proximal end 86 and a distal end 87. A driver coil pack 88 is disposed about the elongate coupler shaft 84 proximal of the penetrating member 83. A position sensor 91 is disposed about a proximal portion 92 (FIG. 6) of the elongate coupler shaft 84 and an electrical conductor 94 electrically couples a processor 93 to the position sensor 91. The elongate coupler shaft 84 driven by the driver coil pack 88 controlled by the position sensor 91 and processor 93 form the controllable driver, specifically, a controllable electromagnetic driver.

Figure 6:
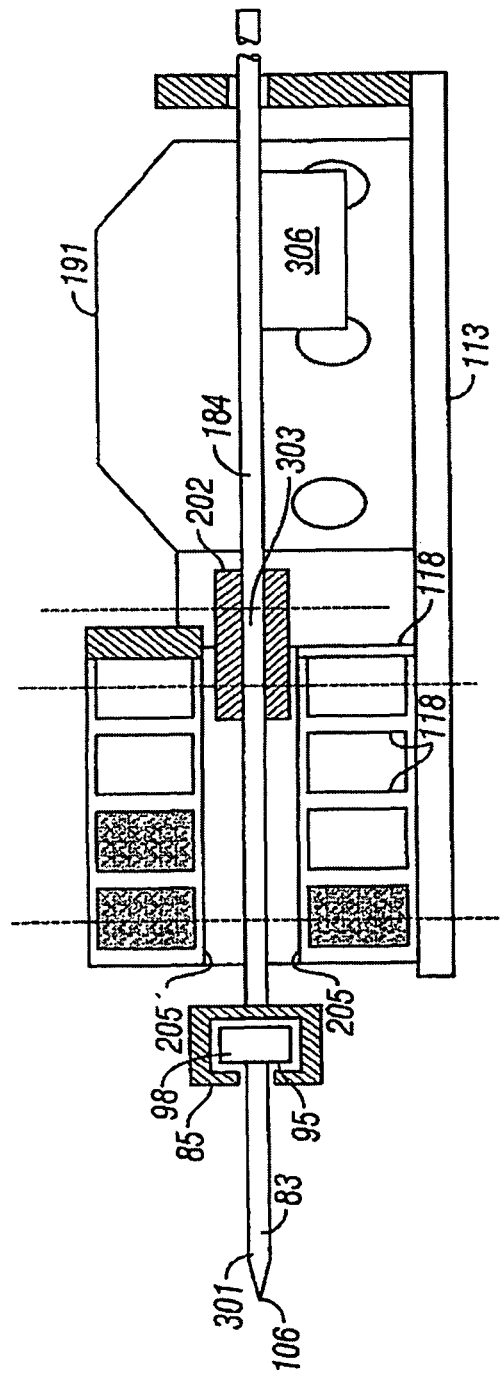
FIG. 6 illustrates the lancing device of FIG. 5 in more detail.

Referring to FIG. 6, the lancing device 80 can be seen in more detail, in partial longitudinal section. The penetrating member 83 has a proximal end 95 and a distal end 96 with a sharpened point at the distal end 96 of the penetrating member 83 and a drive head 98 disposed at the proximal end 95 of the penetrating member 83. A penetrating member shaft 101 is disposed between the drive head 98 and the sharpened point 97. The penetrating member shaft 101 may be comprised of stainless steel, or any other suitable material or alloy and have a transverse dimension of about 0.1 to about 0.4 mm. The penetrating member shaft may have a length of about 3 mm to about 50 mm, specifically, about 15 mm to about 20 mm. The drive head 98 of the penetrating member 83 is an enlarged portion having a transverse dimension greater than a transverse dimension of the penetrating member shaft 101 distal of the drive head 98. This configuration allows the drive head 98 to be mechanically captured by the drive coupler 85. The drive head 98 may have a transverse dimension of about 0.5 to about 2 mm.

A magnetic member 102 is secured to the elongate coupler shaft 84 proximal of the drive coupler 85 on a distal portion 203 of the elongate coupler shaft 84. The magnetic member 102 is a substantially cylindrical piece of magnetic material having an axial lumen 104 extending the length of the magnetic member 102. The magnetic member 102 has an outer transverse dimension that allows the magnetic member 102 to slide easily within an axial lumen 105 of a low friction, possibly lubricious, polymer guide tube 106 disposed within the driver coil pack 88. The magnetic member 102 may have an outer transverse dimension of about 1.0 to about 5.0 mm, specifically, about 2.3 to about 2.5 mm. The magnetic member 102 may have a length of about 3.0 to about 5.0 mm, specifically, about 4.7 to about 4.9 mm. The magnetic member 102 can be made from a variety of magnetic materials including ferrous metals such as ferrous steel, iron, ferrite, or the like. The magnetic member 102 may be secured to the distal portion 203 of the elongate coupler shaft 84 by a variety of methods including adhesive or epoxy bonding, welding, crimping or any other suitable method.

Proximal of the magnetic member 102, an optical encoder flag 106 is secured to the elongate coupler shaft 84. The optical encoder flag 106 is configured to move within a slot in the position sensor 91. The slot may have separation width of about 1.5 to about 2.0 mm. The optical encoder flag 106 can have a length of about 14 to about 18 mm, a width of about 3 to about 5 mm and a thickness of about 0.04 to about 0.06 mm.

The optical encoder flag 106 interacts with various optical beams generated by LEDs disposed on or in the position sensor 91 in a predetermined manner. The interaction of the optical beams generated by the LEDs of the position sensor 91 generates a signal that indicates the longitudinal position of the optical flag 106 relative to the position sensor 91 with a substantially high degree of resolution. The resolution of the position sensor 91 may be about 200 to about 400 cycles per inch, specifically, about 350 to about 370 cycles per inch. The position sensor 91 may have a speed response time (position/time resolution) of 0 to about 120,000 Hz, where one dark and light stripe of the flag constitutes one Hertz, or cycle per second. The position of the optical encoder flag 206 relative to the magnetic member 102, driver coil pack 88 and position sensor 91 is such that the position sensor 91 can provide precise positional information about the penetrating member 83 over the entire length of the penetrating member's power stroke.

An optical encoder that is suitable for the position sensor 91 is a linear optical incremental encoder, model HEDS 9200, manufactured by Agilent Technologies. The model HEDS 9200 may have a length of about 20 to about 30 mm, a width of about 8 to about 12 mm, and a height of about 9 to about 11 mm. Although the position sensor 91 illustrated is a linear optical incremental encoder, other suitable position sensor embodiments could be used, provided they posses the requisite positional resolution and time response. The HEDS 9200 is a two channel device where the channels are 90 degrees out of phase with each other. This results in a resolution of four times the basic cycle of the flag. These quadrature outputs make it possible for the processor to determine the direction of penetrating member travel. Other suitable position sensors include capacitive encoders, analog reflective sensors, such as the reflective position sensor discussed above, and the like.

A coupler shaft guide 111 is disposed towards the proximal end 81 of the lancing device 80. The guide 111 has a guide lumen 112 disposed in the guide 111 to slidingly accept the proximal portion 92 of the elongate coupler shaft 84. The guide 111 keeps the elongate coupler shaft 84 centered horizontally and vertically in the slot 102 of the position sensor 91.

Figure 7:
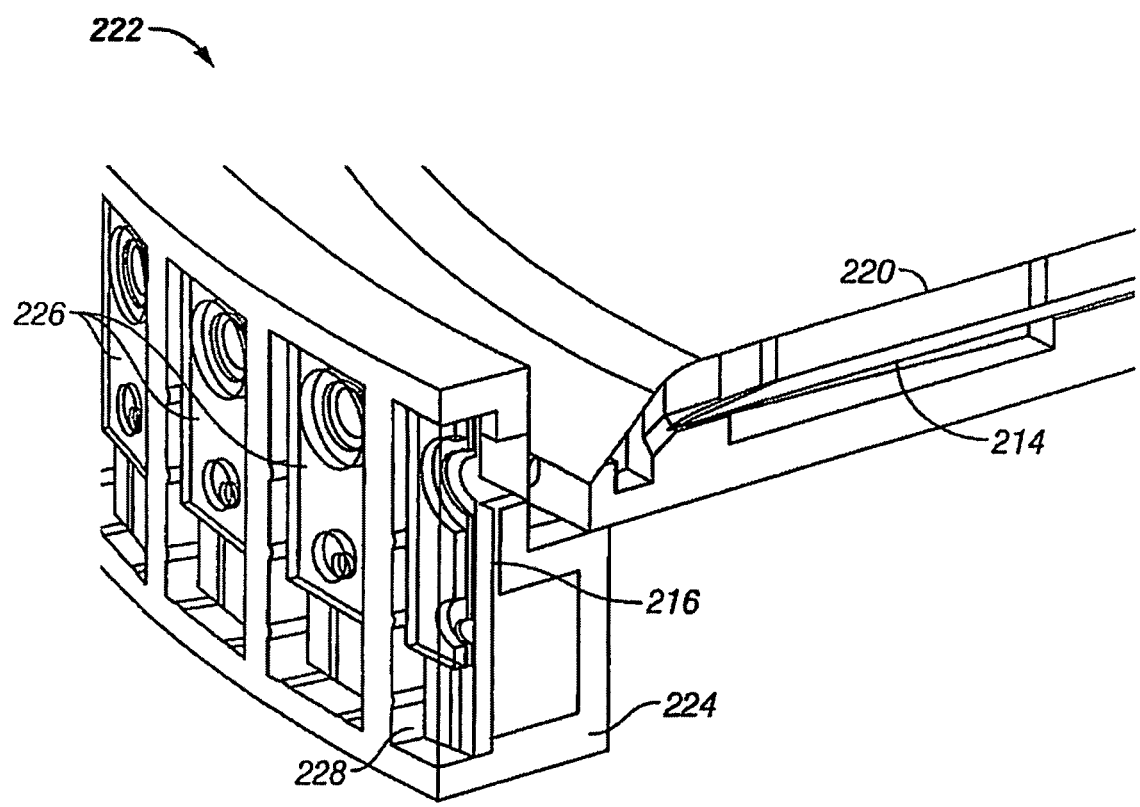
FIG. 7 is a partial sectional view of a disposable device that can be utilized with the methods of the present invention.
Figure 8:
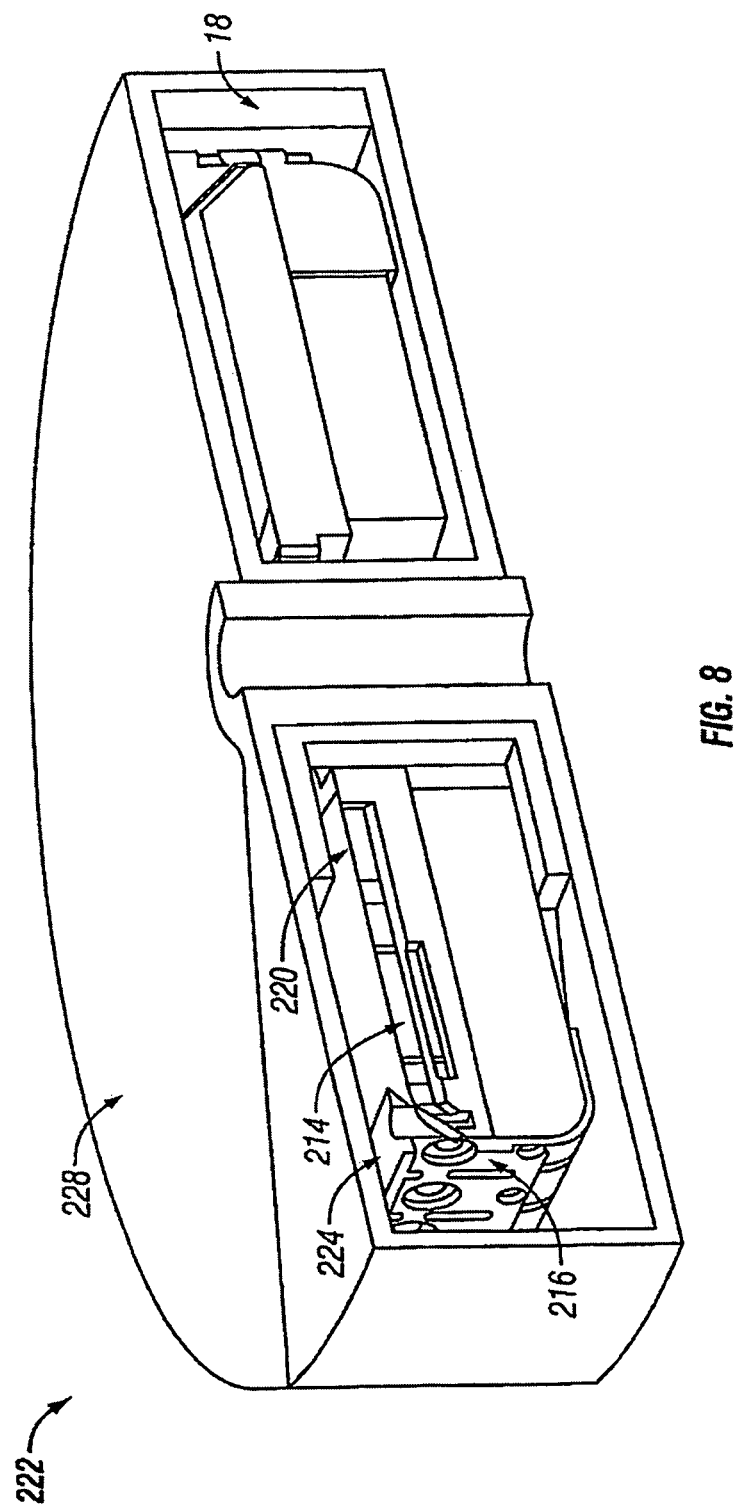
FIG. 8 is a full sectional view of the FIG. 7 disposable device.
Figure 9:
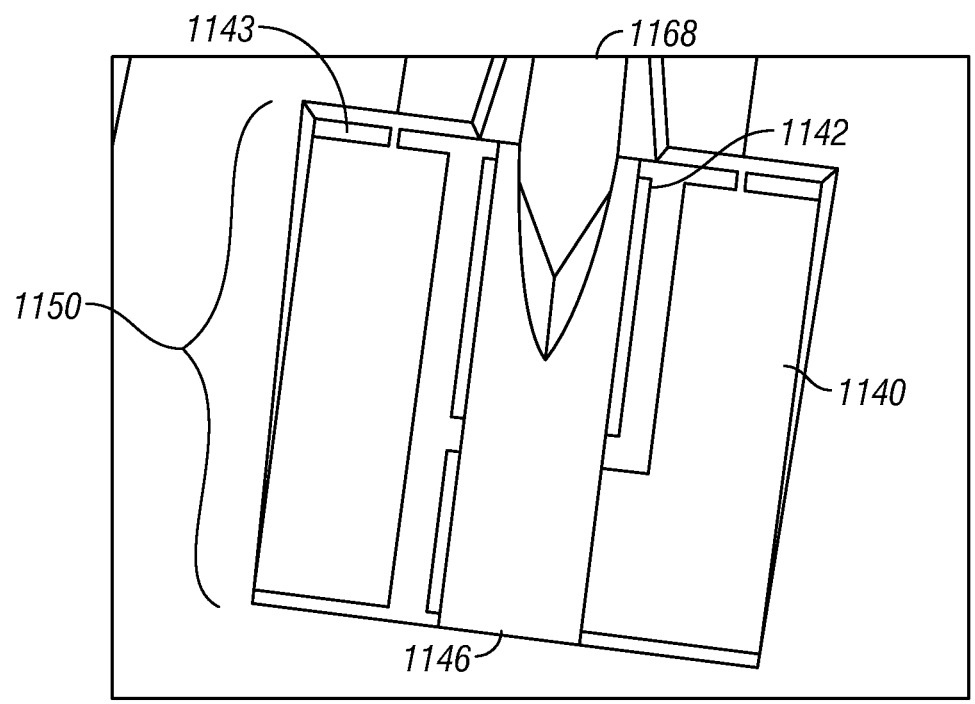
FIG. 9 shows an example of a disposable biosensor test strip including a plurality of penetrating members, capillary chamber associated with each of the penetrating member, working electrode and a counter or reference electrode disposed within the capillary chamber, and a vent 1146 communicating with the capillary chamber.
Figure 10:
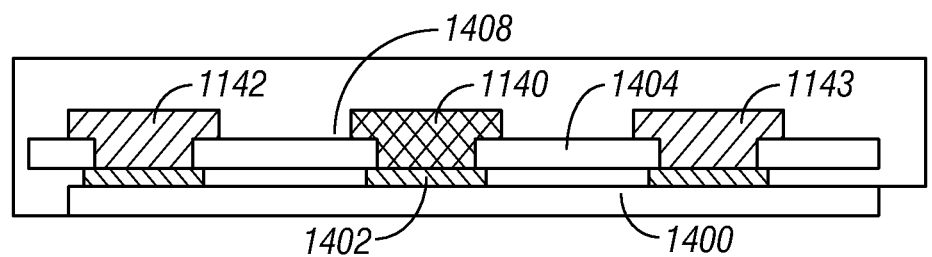
FIG. 10 shows a cross-section of test strip depicted in FIG. 10 having a bottom substrate, a spacing layer, and a top substrate.

As shown in FIGS. 7 and 8, a plurality of penetrating members 214 can be in a disposable member 222 that is placed in a housing of the analyte measurement device. A plurality of analyte detecting members 216 are also included. Each of an analyte detecting member 16 is coupled to a penetrating member 214. A sterility barrier 220 is configured to provide sterile environments for the plurality of penetrating members 214. The sterility barrier 220 can be made of a variety of materials including but not limited to, a metallic foil or other seal materials and may be of a tensile strength and other quality that may provide a sealed, sterile environment until the sterility barrier 220 is penetrated by a penetrating device 214, providing a preselected or selected amount of force to open the sealed, sterile environment.

The sterility barrier 220 can be a planar material that is adhered to a surface of the disposable device 222. Depending on the orientation of the disposable device 222, the sterility barrier 220 can be on the top surface, side surface, bottom surface, or other positioned surface of the disposable device 222.

The plurality of analyte detecting members 216 can be supported on a scaffolding 224. The scaffolding 224 can be attached to a bottom surface of the disposable device 222. The scaffolding 224 can be made of a material such as, but not limited to, a polymer, a foil, and the like. The scaffolding 224 can hold a plurality of analyte detecting members 216, such as but not limited to, about 10-50, 50-100, or other combinations of analyte detecting members 216. This facilitates the assembly and integration of analyte detecting members 216 with disposable device 222. These analyte detecting members 216 can enable an integrated body fluid sampling system where the penetrating members 214 create a wound tract in a target tissue, which expresses body fluid that flows into the disposable device 222 for analyte detection by at least one of the analyte detecting members 216.

In one embodiment, many analyte detecting members 216 can be printed onto a single scaffolding 224 which is then adhered to the disposable device 222 to facilitate manufacturing and simplify assembly. The analyte detecting members 216 can be electrochemical in nature. The analyte detecting members 216 can further contain enzymes, dyes, or other detectors which react when exposed to the desired analyte. Additionally, the analyte detecting members 216 can comprise of clear optical windows that allow light to pass into the body fluid for analyte analysis. The number, location, and type of analyte detecting member 216 can be varied as desired, based in part on the design of the disposable device 222, number of analytes to be measured, the need for analyte detecting member calibration, and the sensitivity of the analyte detecting members 216. Wicking elements, capillary tube or other devices on the disposable device 222 can be provided to allow body fluid to flow from the disposable device 222 to the analyte detecting members 216 for analysis. In other configurations, the analyte detecting members 216 can be printed, formed, or otherwise located directly in the disposable device 222.

The disposable device 222 can include a plurality of cavities 226. Each penetrating member 214 may be contained in a cavity 226 in the disposable device 222 with its sharpened end facing radially outward and may be in the same plane as that of the disposable device 222. The cavity 226 may be molded, pressed, forged, or otherwise formed in the disposable device 222. Although not limited in this manner, the ends of the cavities 226 may be divided into individual fingers (such as one for each cavity) on the outer periphery of the disposable device 222. The particular shape of each cavity 226 may be designed to suit the size or shape of the penetrating member therein or the amount of space desired for placement of the analyte detecting members 216. For example and not limitation, the cavity 226 may have a V-shaped cross-section, a U-shaped cross-section, C-shaped cross-section, a multi-level cross section or the other cross-sections. The opening through which a penetrating member 214 may exit to penetrate tissue may also have a variety of shapes, such as but not limited to, a circular opening, a square or rectangular opening, a U-shaped opening, a narrow opening that only allows the penetrating member 214 to pass, an opening with more clearance on the sides, a slit, and the like.

The use of the sterility barrier 220 can facilitate the manufacture of disposable device 222. For example, a single sterility barrier 220 can be adhered, attached, or otherwise coupled to the disposable device 222 to seal many of the cavities 226 at one time. A sheet of analyte detecting members 216 can also be adhered, attached, or otherwise coupled to the disposable device 222 to provide many analyte detecting members 216 on or in the disposable device 222 at one time. During manufacturing of one embodiment of the present invention, the disposable device 222 can be loaded with penetrating members 214, sealed with sterility barrier 220 and a temporary layer (not shown) on the bottom where scaffolding 224 would later go, to provide a sealed environment for the penetrating members 214. This assembly with the temporary bottom layer is then taken to be sterilized. After sterilization, the assembly is taken to a clean room (or it can already be in a clear room or equivalent environment) where the temporary bottom layer is removed and the scaffolding 224 with analyte detecting members 216 is coupled to the disposable device 222. This process allows for the sterile assembly of the disposable device 222 with the penetrating members 214 using processes and/or temperatures that can degrade the accuracy or functionality of the analyte detecting members 216 on the scaffolding 224.

In some embodiments, more than one sterility barrier 220 can be used to seal the cavities 226. As examples of some embodiments, multiple layers can be placed over each cavity 226, half or some selected portion of the cavities 226 can be sealed with one layer with the other half or selected portion of the cavities sealed with another sheet or layer, different shaped cavities 226 can use different seal layer, or the like. The sterility barrier 220 can have different physical properties, such as those covering the penetrating members 214 near the end of the disposable device 222 can have a different color such as red to indicate to the user (if visually inspectable) that the user is down to say 10, 5, or other number of penetrating members before the cartridge should be changed out.

After actuation, the penetrating member 214 is returned into the disposable device 222 and is held therein in a manner so that it is not able to be used again. By way of example and not limitation, a used penetrating member 214 may be returned into the disposable member 222 and held by a launcher in position until the next lancing event. At the time of the next lancing, the launcher may disengage the used penetrating member with the disposable device 222 turned or indexed to the next clean penetrating member 214 such that the cavity 226 holding the used penetrating member is positioned so that it is not accessible to the user (i.e. turn away from a penetrating member exit opening). In some embodiments, the tip of a used penetrating member 214 may be driven into a protective stop that hold the penetrating member in place after use. The disposable device 222 is replaceable with a new disposable device 222 once all the penetrating members 214 have been used or at such other time or condition as deemed desirable by the user.

The disposable device 222 can provide sterile environments for penetrating members 214 via the sterility barrier 220, seals, foils, covers, polymeric, or similar materials used to seal the cavities 226 and provide enclosed areas for the penetrating members 214 to rest in. In one embodiment, sterility barrier 220 is applied to one surface of the disposable device 220. Each cavity 226 may be individually sealed in a manner such that the opening of one cavity 226 does not interfere with the sterility in an adjacent or other cavity 226. Additionally, the disposable device 222 can include a moisture barrier 228.

The plurality of penetrating members 214 can be at least partially contained in the cavities 226 of the disposable device 222. The penetrating members 214 are slidably movable to extend outward from the disposable device 222 to penetrate tissue. The cavities 226 can each have a longitudinal opening that provides access to an elongate portion of the penetrating member 214. The sterility barrier 220 can cover the longitudinal openings. The sterility barrier 220 can be configured to be moved so that the elongate portion can be accessed by a gripper without touching the sterility barrier 220.

In one embodiment of the present invention, a method is provided of analyte measurement by a user using an analyte measurement device. An analyte measurement is provided with a plurality of penetrating members and analyte sensors. Each analyte sensor is positioned in a sample chamber with a volume no greater than 1 µl. Each sample chamber has a working electrode, reference electrode and a counter electrode. The working electrode has a conductor, an enzyme and a mediator. A penetrating member and an unused analyte detecting member are presented into an active position. The following steps are then performed: (a) the penetrating member is fired to prick the skin and bring a fluid sample to the analyte detecting member, (b) the analyte level is measured, and (c) it takes no more than 10 seconds from the step of presenting the penetrating members and unused analyte into the active position through the step of measuring the analyte level.

In other embodiments, steps (b) and (c) occur in less than 7 seconds, are performed without the user directly handling the penetrating member to obtain a fresh penetrating member or load the penetrating member, are performed without the user coding the analyte measurement device, and are performed without a separate step of apply blood to a analyte detection member after lancing. In certain embodiments, step (b) is performed, without milking a wound., using at least one of a penetrating member driver selected from, spring based, electromechanical based, magnetic driver based, and nanomuscle based, and with controlled velocity and depth of penetration. In one embodiment, a time from pressing an on button of the device to lancing and measuring the analyte level is no more than 10 seconds.

The conductor, mediator and enzyme can be in a single layer of the working electrode. Each working electrode can include a layer that has a conductor, a reagent and the mediator. In one embodiment, the working electrode and the counter or reference electrode are coplanar.

The reagent interacts with glucose to produce an electroactive reaction product, and electroactive reaction product is correlated to a concentration of glucose in a blood sample. The glucose level can then be displayed to the user and the value stored. In various embodiments, the detection of glucose occurs by, (i) applying a drop-detect potential across the working and counter or reference electrodes, (ii) applying a drop-detect potential across the working and counter or reference electrodes and recognizing a rise in current as an indication that the blood sample has been applied into the capillary chamber and (iii) reapplying a potential across the working and counter or reference electrodes after a delay period during which no potential is applied.

The application of blood to an analyte detection member during lancing can occur without removal and disposal of penetrating members from the analyte measurement device.

In another embodiment of the present invention, an analyte measurement is provided with a plurality of penetrating members and analyte sensors. Each analyte sensor is positioned in a sample chamber with a volume no greater than 1 µl. Each sample chamber includes a working electrode, reference electrode and a counter electrode. The working electrode has a conductor, an enzyme and a mediator. The following steps are then performed, (a) a decision is made to test, (b) a penetrating member and an unused analyte detecting member are presented into an active position, (c) the penetrating member is fired to prick the skin and bring a fluid sample to the analyte detecting member and (d) the analyte level is measured. Steps (a) through (d) occur in no more than 1 minute. In other embodiments, steps (a) through (d) occur in no more than 30 seconds, and steps (a) through (d) occur in no more than 15 seconds, steps (a) through (d) occur in no more than 10 seconds.

In another embodiment of the present invention, the following steps are performed: (a) a penetrating member and unused analyte detecting member of the analyte measurement device are presented into an active position by rotating the disposable device to align in an active position, seals covering the penetrating member and analyte detecting member are then removed, (b) The penetrating member is fired to prick the skin using a driver to advance and retract from the skin to create a wound from which body fluid expresses, (c) a fluid sample is brought to the analyte detecting member by providing a sample capture structure positioned to contact body fluid expressed from the wound, and (d) the analyte levels are then measured. Steps (a) through (d) are completed in no more than 10 seconds. In one embodiment, the time from pressing an on button of the device to lancing and measuring the analyte level is no more than 10 seconds.

In another embodiment of the present invention, a disposable biosensor test strip includes a plurality of penetrating members. Each penetrating member is associated with a capillary chamber that has a depth suitable for capillary flow of blood and holds a volume of less than about 1.0 .μl of the blood sample. A working electrode and a counter or reference electrode are disposed within the capillary chamber. A reagent is proximal to or in contact with at least the working electrode. The reagent includes an enzyme and a mediator. The reagent reacts with glucose to produce an electroactive reaction product.

A blood sample, containing glucose, is applied into the capillary chamber. The capillary chamber directs capillary flow of the blood sample into contact with the reagent to cause the blood sample to at least partially solubilize or hydrate the reagent. The blood sample is detected in the capillary chamber. The electroactive reaction product is electro-oxidized or electro-reduced at the working electrode. Within 10 seconds after detecting, a determination is made of glucose concentration and a readout of the measurement is provided. The glucose determination is made by correlating the electro-oxidized or electro-reduced electroactive reaction product to the concentration of glucose in the blood sample.

In one embodiment, the test strip has a bottom substrate, a spacing layer, and a top substrate. The spacing layer has an opening corresponding to the capillary chamber. The spacing layer substantially defines the depth of the capillary chamber. In one embodiment, the test strip is a counter electrode and in the reagent is located proximal to or in contact with the working and counter electrodes.

In one embodiment, detection of glucose is achieved by applying a dose-detect potential between the working and counter or reference electrodes. A rise in current indicates that the sample has been supplied to the capillary chamber. In one embodiment, a potential of 100-500 mV is applied across the working electrode and the counter or reference electrodes.

In various embodiments, (i) the reagent is supplied in a sufficiently small amount as to be solubilized or hydrated in a time sufficient to allow said determining and providing a readout of the glucose concentration in the sample within 10 seconds after said detecting, (ii) a mediator is provided in its oxidized form, (iii) the mediator reacts sufficiently rapidly as to allow said determining and providing a readout of the glucose concentration in the sample within 10 seconds after the detecting step and (iv) the reagent is provided in a sufficiently small amount as to be solubilized or hydrated in a time sufficient to allow said determining and providing a readout of the glucose concentration in the sample within 10 seconds after the detecting step.

In various embodiments, the test strip can have, (i) a bottom substrate, a spacing layer, and a top substrate, the spacing layer having an opening corresponding to the capillary chamber, the spacing layer substantially defining the depth of the capillary chamber, (ii) a vent communicating with the capillary chamber to facilitate flow of the sample into the capillary chamber, (iii) a bottom substrate, a spacing layer, and a top substrate, the spacing layer having an opening corresponding to the capillary chamber, the spacing layer substantially defining the depth of the capillary chamber, (iv) an elongated geometry with two opposed sides, the spacing layer comprising spaced-apart first and second portions defining a capillary chamber extending between and opening at the two opposed sides, (v) a vent communicating with the capillary chamber to facilitate flow of the sample into the capillary chamber, (vi) an elongated geometry with two opposed sides, the spacing layer comprising spaced-apart first and second portions defining a capillary chamber extending between and opening at the two opposed sides and (vii) a counter electrode, and in which the reagent is located proximal to or in contact with the working and counter electrodes.

In various embodiments, the capillary chamber holds a volume, (i) of less than about 0.4 μl, (ii) of between about 0.25 μl and about 0.4 μl, (iii) of less than about 0.4 μl (iv) between about 0.25 μl and about 0.4, (v) of about 600 nL, (vi) of between 0.25 μl and 0.4 μl (vii) of about 400 nL and (viii) of about 300 nL. The capillary chamber can have a depth of about 25 to 200 μm.

In various embodiments, a readout of the glucose concentration is made about, (i) 8 seconds after detecting, (ii) 3.5 to about 8 seconds after detecting, (iii) 4 seconds after detecting and (iv) 3 seconds after detecting. In one embodiment, the test strip, timing the reaction and analysis of the blood sample are automatic to, (i) detect the blood sample in the capillary chamber, (ii) electrooxidize the electroactive reaction product, and (iii) determine and provide a readout of the glucose concentration within 10 seconds of said detecting.

In one embodiment, the detection off glucose includes, applying a dose-detect potential between the working and counter or reference electrodes, and then recognizing a rise in current as an indication that the sample has been supplied to the capillary chamber. In another embodiment, the electroactive reaction product is capable of being electrooxidized or electroreduced at the working electrode, and the determining of the glucose measures the amount of electroactive reaction product electrooxidized or electroreduced and then correlates the amount of electrooxidized or electroreduced electroactive reaction product to the concentration of glucose in the blood sample.

In another embodiment of the present invention, a method of determining the concentration of glucose in a blood sample provides a disposable biosensor test strip and a plurality of penetrating members. Each penetrating member is associated with a capillary chamber that has a depth suitable for capillary flow of blood and holds a volume of less than about 1.0 μl of the blood sample. A working electrode, and a counter or reference electrode, are disposed within the capillary chamber. A reagent is proximal to or in contact with at least the working electrode. The reagent includes an enzyme and a mediator. The reagent reacts with glucose to produce an electroactive reaction product.

A blood sample containing glucose is applied into the capillary chamber. The capillary chamber directs capillary flow of the blood sample into contact with the reagent, causing the blood sample to at least partially solubilize or hydrate the reagent. The blood sample is detected in the capillary chamber. The electroactive reaction product is electrooxided at the working electrode. Within 10 seconds after detection, a readout of the glucose concentration in the blood sample is provided. Detection is made by correlating the electrooxidized electroactive reaction product to the concentration of glucose in the blood sample.

In one embodiment, the reagent is dry, and the capillary chamber directs capillary flow of the blood sample into contact with the dry reagent to cause the blood sample to at least partially solubilize or hydrate the dry reagent. The reagent can be a reagent that is applied wet and dried of solvent.

The reagent can be applied in a sufficiently small amount in order to be solubilized or hydrated in a time that is sufficiently fast to allow the determination and readout of the glucose concentration in the blood sample within 10 seconds of the detection. In one embodiment, the mediator reacts sufficiently rapid to provide a determination and readout of glucose concentration in the blood sample within 10 seconds of said detection. The mediator can be readily reversible.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the shield or other punch may be adapted for use with other cartridges disclosed herein or in related applications. With any of the above embodiments, the methods time may be measured from when the user touches the carrying case or touches the housing (if the device is not being stored in a carrying case).

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of determining the concentration of glucose in a blood sample, comprising:
   providing a disposable biosensor test strip including a plurality of penetrating members arranged to extend radially outward from a flat disc cartridge to penetrate skin to collect the blood sample, each of the penetrating members associated with a capillary chamber having a depth suitable for capillary flow of blood and holding a volume of less than 1.0 µl of the blood sample, a working electrode and a counter or reference electrode disposed within the capillary chamber, and a reagent proximal to or in contact with at least the working electrode, the reagent including an enzyme and a mediator, the reagent reacting with glucose to produce an electroactive reaction product;
   storing and using user profiles in a memory;
   applying a blood sample containing glucose into the capillary chamber, the capillary chamber directing capillary flow of the blood sample into contact with the reagent to cause the blood sample to at least partially solubilize or hydrate the reagent;
   detecting the blood sample in the capillary chamber;
   electrooxidizing or electroreducing the electroactive reaction product at the working electrode; and
   within 10 seconds after said detecting, determining and providing a readout of the glucose concentration in the blood sample, said determining comprising correlating the electrooxidized or electroreduced electroactive reaction product to the concentration of glucose in the blood sample.

2. The method of claim 1 in which said detecting comprises applying a dose-detect potential between the working and counter or reference electrodes, and recognizing a rise in current as an indication that the sample has been supplied to the capillary chamber.

3. The method of claim 1 in which the test strip includes a vent communicating with the capillary chamber to facilitate flow of the sample into the capillary chamber.

4. The method of claim 1 in which said providing comprises providing the reagent in a small amount as to be solubilized or hydrated in a time sufficient to allow said determining and providing a readout of the glucose concentration in the sample within 10 seconds after said detecting.

5. The method of claim 1 in which said providing comprises providing a test strip including a bottom substrate, a spacing layer, and a top substrate, the spacing layer having an opening corresponding to the capillary chamber, the spacing layer defining the depth of the capillary chamber.

6. The method of claim 5 in which the test strip is elongated with two opposed sides, the spacing layer comprising spaced-apart first and second portions defining a capillary chamber extending between and opening at the two opposed sides.

7. The method of claim 1 in which said providing comprises providing a mediator in an oxidized form.

8. The method of claim 7 in which the mediator reacts rapidly as to allow said determining and providing a readout of the glucose concentration in the sample within 10 seconds after said detecting.

9. The method of claim 8 in which said providing comprises providing the reagent in a small amount as to be solubilized or hydrated in a time sufficient to allow said determining and providing a readout of the glucose concentration in the sample within 10 seconds after said detecting.

10. The method of claim 9 in which the capillary chamber holds a volume of less than 0.4 µl.

11. The method of claim 10 in which the capillary chamber holds a volume of between 0.25 µl and 0.4 µl.

12. The method of claim 11 in which said detecting comprises applying a dose-detect potential between the working and counter or reference electrodes, and recognizing a rise in current as an indication that the sample has been supplied to the capillary chamber.

13. The method of claim 12 in which the test strip includes a vent communicating with the capillary chamber to facilitate flow of the sample into the capillary chamber.

14. The method of claim 13 in which said providing comprises providing a test strip including a bottom substrate, a spacing layer, and a top substrate, the spacing layer having an opening corresponding to the capillary chamber, the spacing layer defining the depth of the capillary chamber.

15. The method of claim 14 in which the test strip is elongated with two opposed sides, the spacing layer comprising spaced-apart first and second portions defining a capillary chamber extending between and opening at the two opposed sides.

16. The method of claim 1 in which the capillary chamber holds a volume of less than 0.4 µl.

17. The method of claim 16 in which the capillary chamber holds a volume of between 0.25 .µl and 0.4 µl.

18. The method of claim 1 in which said electroactive reaction product is capable of being electrooxidized or electroreduced at the working electrode, said determining comprising measuring the amount of electroactive reaction product electrooxidized or electroreduced, and correlating the amount of electrooxidized or electroreduced electroactive reaction product to the concentration of glucose in the blood sample.

19. The method of claim 1 in which said capillary chamber has a depth of 25-200 μm.

20. The method of claim 1 including automatically operating the test strip and timing the reaction and analysis of the blood sample to detect the blood sample in the capillary chamber, to electrooxidize the electroactive reaction product, and to determine and provide a readout of the glucose concentration within 10 seconds of said detecting.

21. The method of claim 1 in which the test strip comprises a counter electrode, and in which the reagent is located proximal to or in contact with the working and counter electrodes.

* * * * *